(12) United States Patent
Abrams et al.

(10) Patent No.: US 12,063,929 B2
(45) Date of Patent: Aug. 20, 2024

(54) 3'-ALKYNYL ABSCISIC ACID DERIVATIVES AS ABA ANTAGONISTS

(71) Applicant: University of Saskatchewan, Saskatoon (CA)

(72) Inventors: Suzanne R. Abrams, Saskatoon (CA); Leon Lai, Saskatoon (CA); Naveen Diddi, Saskatoon (CA)

(73) Assignee: UNIVERSITY OF SASKATCHEWAN, Saskatoon (CA)

( * ) Notice: Subject to any disclaimer, the term of this patent is extended or adjusted under 35 U.S.C. 154(b) by 548 days.

(21) Appl. No.: 17/309,256

(22) PCT Filed: Nov. 19, 2019

(86) PCT No.: PCT/CA2019/051650
§ 371 (c)(1),
(2) Date: May 12, 2021

(87) PCT Pub. No.: WO2020/102892
PCT Pub. Date: May 28, 2020

(65) Prior Publication Data
US 2021/0392885 A1    Dec. 23, 2021

Related U.S. Application Data

(60) Provisional application No. 62/769,331, filed on Nov. 19, 2018.

(51) Int. Cl.
| | |
|---|---|
| *C07C 59/90* | (2006.01) |
| *A01N 37/42* | (2006.01) |
| *A01P 21/00* | (2006.01) |
| *C07C 69/738* | (2006.01) |

(52) U.S. Cl.
CPC ............. *A01N 37/42* (2013.01); *A01P 21/00* (2021.08); *C07C 59/90* (2013.01); *C07C 69/738* (2013.01)

(58) Field of Classification Search
CPC ....... C07C 59/90; C07C 69/738; A01N 37/42; A01P 21/00
See application file for complete search history.

(56) References Cited

U.S. PATENT DOCUMENTS

| | | | | |
|---|---|---|---|---|
| 8,969,249 B2 * | 3/2015 | Abrams | ............... | C07C 69/738 562/490 |
| 9,447,015 B1 | 9/2016 | Wang et al. | | |
| 2013/0158098 A1 * | 6/2013 | Liang | ................... | A61K 31/122 435/375 |
| 2017/0360037 A1 * | 12/2017 | Wang | .................... | A01N 37/42 |

FOREIGN PATENT DOCUMENTS

| | | |
|---|---|---|
| WO | 2011/163029 A1 | 12/2011 |
| WO | 2016/007587 A2 | 1/2016 |

OTHER PUBLICATIONS

International Search Report and Written Opinion of PCT/CA2019/051650, Mar. 4, 2020.
Arai, Sho et al.,. "Synthesis and Biological Activity of 3'-chloro, -bromo, and -iodoabscisic acids, and biological activity of 3' -fluoro-8'-hydroxyabscisic acid", Phytochemistry 52 (1999), 1185-1193.
Takeuchi, Jun et al., "Structure-Based Chemical Design of Abscisic Acid Antagonists that Block PYL-PP2C Receptor Interactions", ACS Chem. Biol. 2018, 13, 1313-1321.
STN Internationl Search Transcript, Nov. 15, 2018.
Rajagopalan, Nandhakishore et al., "Abscisic Acid Analogues that act as Universal or Selective Antagonists of Phytohormone Receptors", Biochemistry, Aug. 19, 2016, 55, 36, 5155-5164.
Benson, C.L. et al., 2015 Abscisic acid analogs as chemical probes for dissection of abscisic acid responses in *Arabidopsis Thaliana*. Phytochemistry, 113, 96-107.
Boyd, J.; et al., Bioorg. Med. Chem. 2009, 17, 2902-2912.
Hirai, N., Fukui, H., Koshimizu, K. 1978 A novel abscisic acid catabolite from seeds of Robinia pseudoacacia Phytochemistry 17: 1625-7.

(Continued)

*Primary Examiner* — Sikarl A Witherspoon
(74) *Attorney, Agent, or Firm* — Bereskin & Parr LLP/S.E.N.C.R.L., s.r.l.; Sandra Marone

(57) ABSTRACT

The present application relates to novel 3'-unsaturated abscisic acid (ABA) derivatives of Formula (I) as ABA antagonists. For example, the present application relates to methods of using compounds of Formula (I) for reducing adverse effects of an ABA response in plants such as lentil and promoting germination. (I) The present application also relates to methods of using 3'-phenyl abscisic acid (ABA) derivatives of Formula (II) as ABA antagonists, for example, for reducing adverse effects of an ABA response in plants such as lentil and promoting germination. (II)

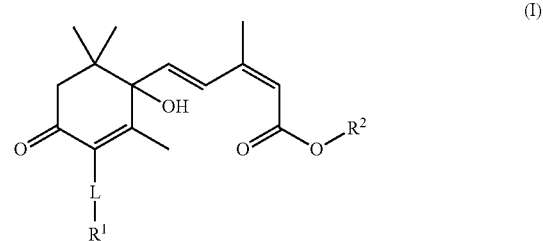

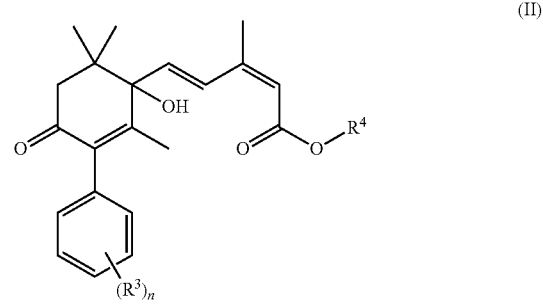

22 Claims, 17 Drawing Sheets

(56) References Cited

OTHER PUBLICATIONS

Nonogaki H. 2014. Seed dormancy and germination-emerging mechanisms and new hypotheses. Front Plant Sci. 5: 233.

Slater et al. 2013 Comprehensive hormone profiling of the developing seeds of four grain legumes, Plant Cell Rep., 32: 1939-1952.

Takeuchi, J., et al., Designed abscisic acid analogs as antagonists of PYL-PP2C receptor interactions. Nat. Chem. Biol. 2014, 10, 477-482.

Walker-Simmons MK, Anderberg RJ, Rose PA, Abrams SR. 1992. Optically pure ABA analogs: Tools for relating germination inhibition and gene expression in wheat embryos. Plant Physiol 99:501-507.

Wilen RW, Hays DB, Mandel RM, Abrams SR, Moloney MM. 1993. Competitive inhibition of abscisic acid-regulated gene expression by stereoisomeric acetylenic analogs of abscisic acid. Plant Physiol 101:469-476.

Stratichuk, H. 2016. Testing the Potential Use of an Abscisic Acid (ABA) Antagonist as a Desiccant in Pulses. Undergraduate Student Thesis Presentation, Soils and Crops, Mar. 15-16, 2016, Saskatoon. (Please see accompanying letter).

Song, D.Y., S. Abrams and B. Tar'an. 2016. Application of abscisic acid (ABA) analogs for Improving pulse crop agronomy and physiology 10th Canadian Pulse Research Workshop, Winnipeg, MB, Oct. 25-28, 2016 (Abstract).

Zhou, J., , Tar'an, B., and Abrams, S., 2017, Promotive effects of ABA antagonists on seed germination of *Brassica napus* under low temperature., North American Pulse Improvement Association meeting, East Lansing MI Nov. 2-3, 2017 (Abstract).

Abrams, S. 2017, Potential of ABA Analogs as Plant Growth Regulators for Pulse Crops, North American Pulse Improvement Association meeting East Lansing MI Nov. 2-3, 2017 (Abstract).

\* cited by examiner (10 µM ABA - 100 µM 1019)

(10 µM ABA - 100 µM 1019)

Figure 4
Figure 4A
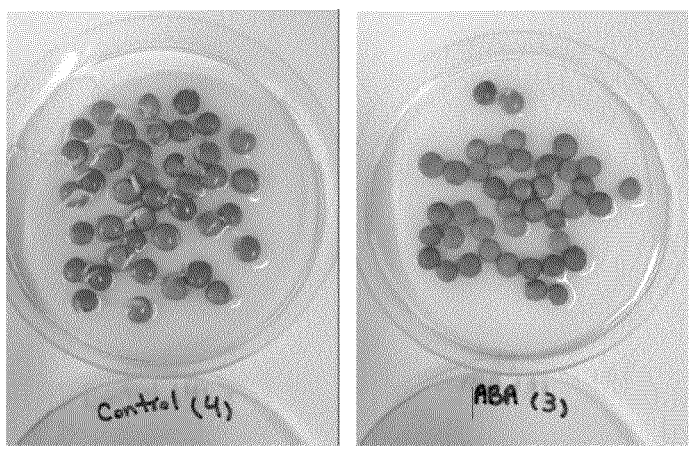
Figure 4B
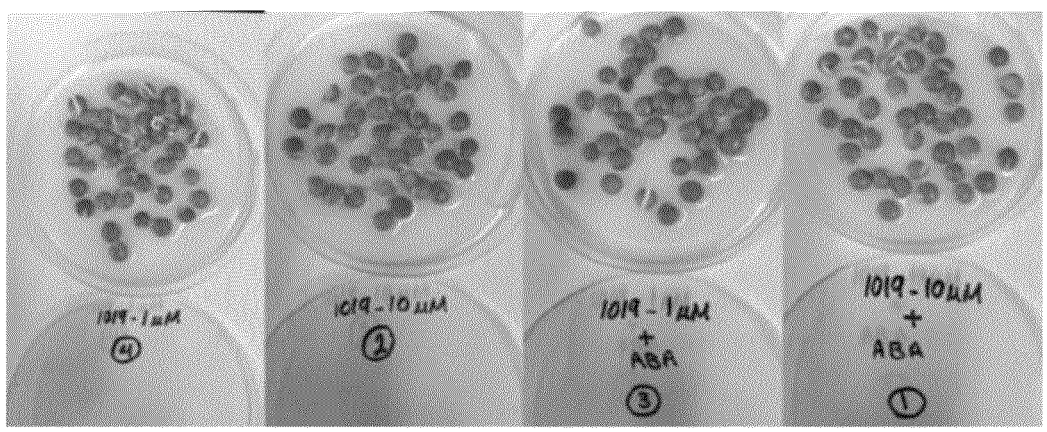
Figure 4C
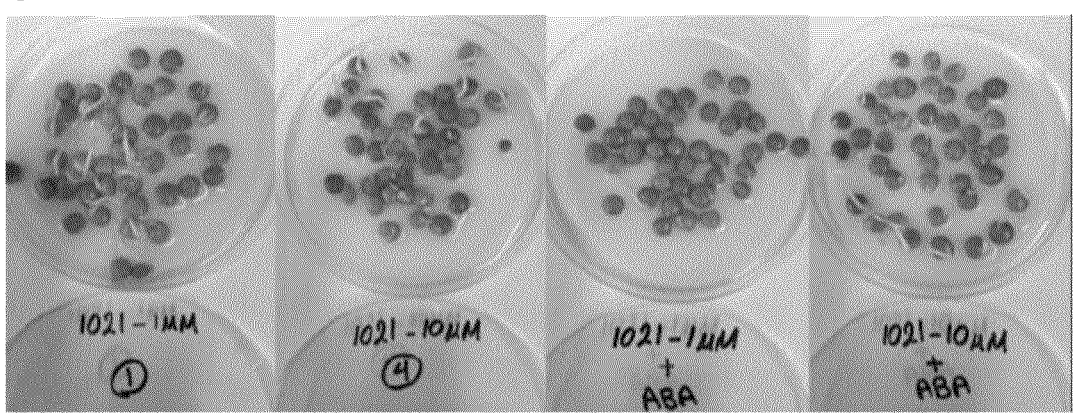

3'-ALKYNYL ABSCISIC ACID DERIVATIVES AS ABA ANTAGONISTS

RELATED APPLICATIONS

This application is a National Stage of co-pending International Application No. PCT/CA2019/051650 filed on Nov. 19, 2019 which claims the benefit of priority from U.S. Provisional Patent Application Ser. No. 62/769,331 filed on Nov. 19, 2018, the contents of both of which are incorporated herein by reference in their entirety.

FIELD

The present application relates to 3'-unsaturated abscisic acid (ABA) derivatives of Formula (I), to processes for their preparation and to their use as ABA antagonists. In particular, the present application relates to methods of using 3'-unsaturated ABA derivatives for reducing adverse affects of an ABA response in plants such as lentil and promoting germination. Also included are methods of using 3'-phenyl-substituted ABA derivatives of Formula II for reducing adverse affects of an ABA response in plants such as lentil and promoting germination.

BACKGROUND

Pulse crop production in Saskatchewan has been rising steadily over the past decades. In 2016, Saskatchewan's farmers seeded nearly 5.3 M acres of lentils, 2.2 M acres of field peas and 170,000 acres of chickpeas, and generated a total production of nearly 5.2 M metric tonnes. One of the main reasons for this increase is that growers have realized significant financial benefits from pulse crops relative to cereal or oilseed options in their crop rotations. To maintain the sustainability of pulse production on the Prairies, problems such as poor germination under cold and wet conditions, non-uniform crop maturity especially faba bean and chickpea, are an issue.

Seed dormancy and germination, to a large extend, is influenced by the levels of the plant hormones gibberellic acid (GA) and abscisic acid (ABA). These hormones have been the subject of extensive research to understand their mechanism to improve germination and ultimately, crop establishment and yield (Nonaka et al 2014).[1] ABA involvement in dormancy maintenance and germination inhibition has been demonstrated in a number of different ways, for example (1) with mutants impaired in ABA signalling (e.g. viviparous corn); (2) through germination experiments at low or high temperature where germination is delayed and ABA levels are observed to increase; (3) in germination experiments in which supplied ABA delays germination in a concentration dependent manner; and (4) in transgenic plants in which ABA levels and signalling are altered. The range of temperatures suitable for seed germination varies with the plant species. In pulse crops, especially the warm season pulses such as soybean and dry bean, low temperature seriously limits germination and early growth, and eventually results in yield loss. There are numerous reports that indicated germination under suboptimal temperatures can lead to increased ABA levels and slower germination in oilseeds and cereals and other species. Recent works have suggested that the use of ABA analogs may be able to overcome these problems. Differences in the plant physiological and molecular responses in response to changes in the structure of the ABA analog molecules being applied have been well documented (Walker-Simmons et al. 1992, Wilen et al. 1993; Benson et al 2015, Abrams and Loewen 2019).[2-5] ABA-related seed dormancy, slow germination and emergence of seedlings are all issues for plant breeders working with wild relatives of cultivated species. These issues result in long generation times that impede progress towards developing improved varieties. ABA antagonist have potential to improve plant breeding methods.

Annual economic losses due to plant pathogens are estimated to amount to 10 to 16% of global crop production (Chakraborty and Newton 2011).[6] Numerous pathogens utilize plant hormone signaling systems to render plants susceptible to diseases. ABA is normally thought of as a plant hormone protecting plants from abiotic stress but recent research is uncovering diverse roles for ABA in plant pathogen interactions and that ABA can act directly or through other hormones such as jasmonate and salicylate (Lievens et al. 2017; Forlani et al. 2019; Cao et al. 2019).[7-9] In wheat an ABC transporter LR34 for which ABA is a substrate, confers resistance to a number of fungal pathogens (Krattinger et al. 2019).[10] In contrast, Xanthomonas translucens acts in wheat by increasing expression of the plant NCED that is the rate limiting enzyme in ABA biosynthesis, leading to increased levels of ABA. Elevated ABA levels enhance the spreading of a bacterial gene which down regulates NPR1 rendering the plant susceptible to infection (Peng et al. 2019).[11] In rice ABA suppresses salicylate-induced resistance to Rice Leaf Blight Pathogen Xanthomonas oryzae (Xi et al. 2013).[12] On the pathogen side, it is known that several phytopathogenic fungi, including Botrytis cinerea which causes grey mold diseases and Cercospera spp. that cause leaf spots on a wide range of crop species, produce ABA as a virulence factor to promote disease development during infection (Takino et al. 2019; Mbengue et al. 2016).[13,14]

Chickpea and faba bean are among the long season pulse crops. Chickpea in particular has a strong indeterminacy. The plants continue to grow after entering the regenerative stage so long as the environmental conditions are conducive. Stress conditions (water, temperature or nitrogen) are needed to cease the growth of chickpea and turn the plants to maturity. To date, desiccation treatment has been a common practice to stop plant growth such as lentil, field pea, faba bean and chickpea and prepare the crops for harvesting by removing moisture from plants and late maturing areas of the field. The use of ABA antagonists is expected to increase water loss by keeping the stomata open and in turn force the crop to die down or to turn maturity.

Various ABA derivatives have been disclosed in the art. For example, Rajagopalan et al. 2016[15] synthesized ABA antagonists using a process requiring eleven separate steps, beginning from commercially available starting materials; Takeuchi et al. 2014[16] synthesized a class of 3'-sulfur ABA derivatives; and WO2016/007587[17] provides a class of 3'-substituted ABA derivatives. Song et al. 2019 reported a series of 3'-alkyl substituted analogs with moderate antagonist properties in overcoming ABA-induced inhibition of germination.[18]

SUMMARY

The present application describes a novel class of 3'-unsaturated ABA derivatives that have been shown to reduce adverse effects of an ABA response in a plant, and that are relatively straightforward and inexpensive to prepare.

Accordingly, the present application includes a compound of Formula (I) or an enantiomer, salt, and/or solvate thereof:

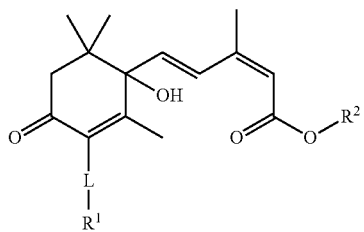

(I)

wherein
L is —C=C— or —C≡C—;
R$^1$ is C$_{1-10}$alkyl, C$_{2-10}$alkenyl, C$_{2-10}$alkynyl, (CH$_2$)$_{0-2}$C$_{3-10}$cycloalkyl, (CH$_2$)$_{0-2}$aryl, (CH$_2$)$_{0-2}$heterocycloalkyl, or (CH$_2$)$_{0-2}$heteroaryl, each being optionally substituted with one or more of halo, CN, OH, NH$_2$, C$_{1-10}$alkyl, C$_{2-10}$alkenyl, C$_{2-10}$alkynyl, NH(C$_{1-6}$alkyl), N(C$_{1-6}$alkyl)(C$_{1-6}$alkyl), OC$_{1-6}$alkyl, OC$_{2-6}$alkenyl, OC$_{2-6}$alkynyl, (CH$_2$)$_{0-2}$C$_{3-10}$ cycloalkyl, (CH$_2$)$_{0-2}$aryl, (CH$_2$)$_{0-2}$heterocycloalkyl, (CH$_2$)$_{0-2}$heteroaryl, O(CH$_2$)$_{0-2}$C$_{3-10}$cycloalkyl, O(CH$_2$)$_{0-2}$aryl, O(CH$_2$)$_{0-2}$heterocycloalkyl, or O(CH$_2$)$_{0-2}$heteroaryl, the latter 16 groups being optionally substituted with one or more of halo, OH, NH$_2$, C$_{1-6}$alkyl, C$_{2-6}$alkenyl, C$_{2-6}$alkynyl, OC$_{1-16}$alkyl, OC$_{2-6}$alkenyl, or OC$_{2-6}$alkynyl; and
R$^2$ is H, C$_{1-10}$alkyl, C$_{2-10}$alkenyl, C$_{2-10}$alkynyl, cycloalkyl, aryl, heterocycloalkyl or heteroaryl, the latter 7 groups being optionally substituted with one or more of halo, OH, NH$_2$, C$_{1-6}$alkyl, C$_{2-6}$alkenyl, C$_{2-6}$alkynyl, OC$_{1-16}$alkyl, OC$_{2-6}$alkenyl, or OC$_{2-6}$alkynyl,
wherein each alkyl, alkenyl, and alkynyl are optionally fluorosubstituted.

In an embodiment, R$^1$ is (CH$_2$)$_{0-2}$aryl optionally substituted with one or more of halo, CN, OH, NH$_2$, C$_{1-10}$alkyl, OC$_{1-6}$alkyl, (CH$_2$)$_{0-2}$C$_{3-10}$cycloalkyl, (CH$_2$)$_{0-2}$aryl, (CH$_2$)$_{0-2}$heterocycloalkyl, (CH$_2$)$_{0-2}$heteroaryl, O(CH$_2$)$_{0-2}$C$_{3-10}$cycloalkyl, O(CH$_2$)$_{0-2}$aryl, O(CH$_2$)$_{0-2}$heterocycloalkyl or O(CH$_2$)$_{0-2}$heteroaryl, the latter 10 groups being optionally substituted with one or more of halo, OH, NH$_2$, C$_{1-6}$alkyl, C$_{2-6}$alkenyl, C$_{2-6}$alkynyl, OC$_{1-16}$alkyl, OC$_{2-6}$alkenyl, or OC$_{2-6}$alkynyl, wherein each alkyl, alkenyl, and alkynyl are optionally fluorosubstituted.

In an embodiment, R$^4$ is C$_{1-10}$alkyl optionally substituted with one or more of halo, CN, OH, NH$_2$, C$_{1-10}$alkyl, C$_{2-10}$alkenyl, C$_{2-10}$alkynyl, NH(C$_{1-6}$alkyl), N(C$_{1-6}$alkyl) (C$_{1-6}$alkyl), OC$_{1-6}$alkyl, OC$_{2-6}$alkenyl, OC$_{2-6}$alkynyl, (CH$_2$)$_{0-2}$C$_{3-10}$ cycloalkyl, (CH$_2$)$_{0-2}$aryl, (CH$_2$)$_{0-2}$heterocycloalkyl, (CH$_2$)$_{0-2}$heteroaryl, O(CH$_2$)$_{0-2}$C$_{3-10}$cycloalkyl, O(CH$_2$)$_{0-2}$aryl, O(CH$_2$)$_{0-2}$heterocycloalkyl, or O(CH$_2$)$_{0-2}$heteroaryl, the latter 16 groups being optionally substituted with one or more of halo, OH, NH$_2$, C$_{1-6}$alkyl, C$_{2-6}$alkenyl, C$_{2-6}$alkynyl, OC$_{1-16}$alkyl, OC$_{2-6}$alkenyl, or OC$_{2-6}$alkynyl, wherein each alkyl, alkenyl, and alkynyl are optionally fluorosubstituted.

The application also includes a method for reducing adverse effects of an ABA response comprising administering an effective amount of one or more compounds of the application to a plant in need thereof.

The present application also includes a method for reducing adverse effects of an ABA response in a plant in need thereof comprising administering an effective amount of one or more compounds of the Formula (II) or an enantiomer, salt, and/or solvate thereof, to the plant,

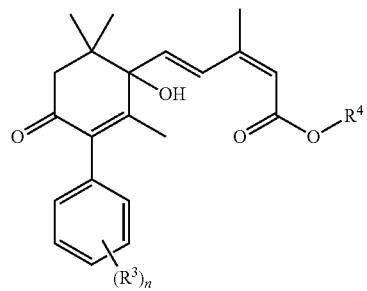

(II)

wherein:
n is 0, 1, 2, or 3;
each R$^3$ is independently selected from OH, halo, C$_{1-10}$alkyl, OC$_{1-6}$alkyl, and O(CH$_2$)$_{0-2}$aryl, the latter 3 groups being optionally substituted with one or more of halo, OH, NH$_2$, C$_{1-6}$alkyl, C$_{2-6}$alkenyl, C$_{2-6}$alkynyl, OC$_{1-16}$alkyl, OC$_{2-6}$alkenyl, or OC$_{2-6}$alkynyl; and
R$^4$ is selected from H or C$_{1-10}$alkyl,
wherein each alkyl, alkenyl, and alkynyl is optionally fluorosubstituted.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole

BRIEF DESCRIPTION OF DRAWINGS

The embodiments of the application will now be described in greater detail with reference to the attached drawings in which:

FIG. 7A is a bar graph showing the percent germination at 48 h. FIG. 7B shows percent germination over time (24 h, 48 h and 72 h post treatment).

FIG. 9A shows the total root growth at 72 h. FIG. 9B shows shoot root growth at 72 h post treatment.

FIG. 11A shows the effects of 5 uM ABA or 5 uM ABA+10 uM 1019 on radical length of rice 4.5 days post treatment. Least Square mean: Ctrl: (A)=1.0666667; 1019: (A)=1.0363636; ABA+1019: (A)=0.8673913; $H_2O$: (A)=0.8568182; ABA: (B)=0.2727273. FIG. 11B shows the effects of 5 uM ABA or 5 uM ABA+10 uM 1019 on radical length of barley 3.0 days post treatment. Least Square mean: $H_2O$: (A)=3.1906250; Ctrl: (A)=3.1000000; ABA+1019: (A)=2.9300000; 1019: (A)=2.8300000; ABA: (B)=1.7181818. FIG. 11C shows the effects of 5 uM ABA or 5 uM ABA+10 uM 1019 on radical length of wheat 3.0 days post treatment. Least Square mean: ABA+1019: (A)=2.5386364; Ctrl: (A)=2.5069767; $H_2O$: (A)=2.4000000; 1019: (A)=2.3860465; ABA: (B)=1.7113636. FIG. 11D shows the effects of 10 uM ABA or 10 uM ABA+20 uM 1019 on radical length of sorghum 3.0 days post treatment. Least Square mean: $H_2O$: (A)=0.29090909; Ctrl: (AB)=0.26976744; ABA+1019: (B)=0.20454545; 1019: (B)=0.20444444; ABA: (C)=0.11707317. Results A, B and C are statistically different from each other.

DETAILED DESCRIPTION

I. Definitions

Figure 1A:
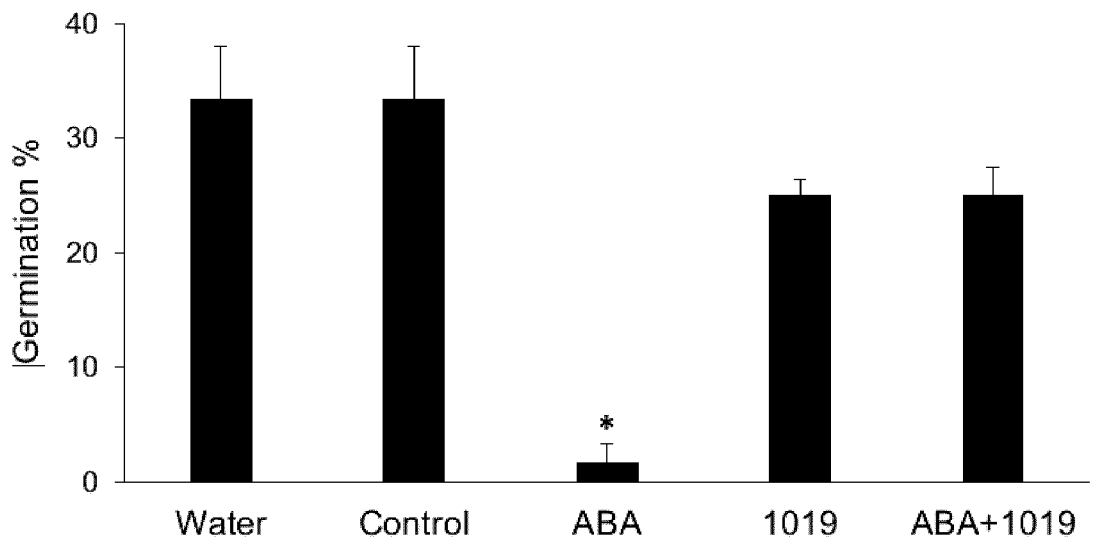
FIG. 1A is a bar graph showing the effect of exemplary compound 1019 used alone or in combination with ABA on percent germination of lentil seed at a dosage of 10 µM ABA and 100 µM compound 1019 on day 1 compared to ABA alone.
Figure 1B:
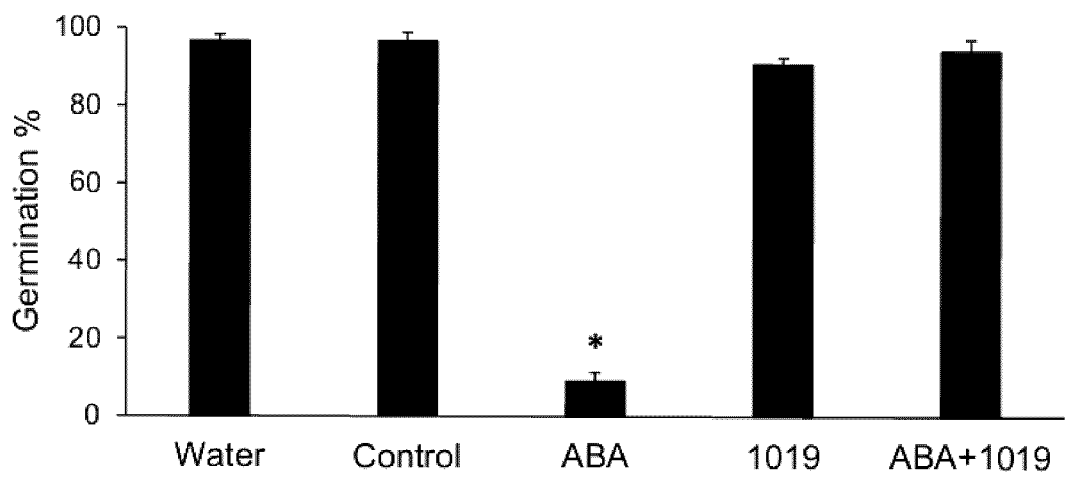
FIG. 1B is a bar graph showing the effect of exemplary compound 1019 used alone or in combination with ABA on percent germination of lentil seed at a dosage of 10 µM ABA and 100 µM compound 1019 on day 2 compared to ABA alone.

Unless otherwise indicated, the definitions and embodiments described in this and other sections are intended to be applicable to all embodiments and aspects of the present application herein described for which they are suitable as would be understood by a person skilled in the art.

The term "compound of the application" or "compound of the present application" and the like as used herein refers to a compound of Formula (I) or enantiomers, salts and/or solvates thereof.

The term "composition of the application" or "composition of the present application" and the like as used herein refers to a composition comprising one or more compounds of the application and/or one or more compounds of Formula (II) or enantiomers, salts and/or solvates thereof.

The term "and/or" as used herein means that the listed items are present, or used, individually or in combination. In effect, this term means that "at least one of" or "one or more" of the listed items is used or present. The term "and/or" with respect to salts and/or solvates thereof means that the compounds of the application exist as individual salts and hydrates, as well as a combination of, for example, a salt of a solvate of a compound of the application.

As used in the present application, the singular forms "a", "an" and "the" include plural references unless the content clearly dictates otherwise. For example, an embodiment including "a negative response" should be understood to present certain aspects with one negative, or two or more additional negative responses.

In embodiments comprising an "additional" or "second" component or effect, such as an additional or second adverse effect, the second effect as used herein is different from the other effects or first effect. A "third" adverse effect is different from the other, first, and second effects, and further enumerated or "additional" adverse effects are similarly different.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements; components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art.

In embodiments of the present application, the compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having an alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form, as well as mixtures thereof, are included within the scope of the present application.

The compounds of the present application may further exist in varying polymorphic forms and it is contemplated that any polymorphs, or mixtures thereof, which form are included within the scope of the present application.

The present description refers to a number of chemical terms and abbreviations used by those skilled in the art. Nevertheless, definitions of selected terms are provided for clarity and consistency.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-10}$alkyl means an alkyl group having 1, 2, 3, 4, 5, 6, 7, 8, 9 or 10 carbon atoms.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{2-6}$alkylene means an alkylene group having 2, 3, 4, 5 or 6 carbon atoms.

The term "alkenyl" as used herein, whether it is used alone or as part of another group, means straight or branched chain, unsaturated alkyl groups containing at least one double bond. The number of carbon atoms that are possible in the referenced alkenyl group are indicated by the prefix "$C_{n1-n2}$". For example, the term $C_{2-6}$alkenyl means an alkenyl group having 2, 3, 4, 5 or 6 carbon atoms and at least one double bond.

The term "alkynyl" as used herein, whether it is used alone or as part of another group, means straight or branched chain, unsaturated alkynyl groups containing at least one triple bond. The number of carbon atoms that are possible in the referenced alkyl group are indicated by the prefix "$C_{n1-n2}$". For example, the term $C_{2-6}$alkynyl means an alkynyl group having 2, 3, 4, 5 or 6 carbon atoms.

The term "cycloalkyl," as used herein, whether it is used alone or as part of another group, means a saturated carbocyclic group containing a number of carbon atoms and one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms. When a cycloalkyl group contains more than one ring, the rings may be fused, bridged, spirofused or linked by a bond.

The term "aryl" as used herein, whether it is used alone or as part of another group, refers to carbocyclic groups containing at least one aromatic ring and contains either 6, 9 or 10 carbon atoms, such as phenyl, indanyl or naphthyl.

The term "heterocycloalkyl" as used herein, whether it is used alone or as part of another group, refers to cyclic groups containing at least one non-aromatic ring containing from 3 to 10 atoms in which one or more of the atoms are a heteroatom selected from O, S and N and the remaining atoms are C. Heterocycloalkyl groups are either saturated or unsaturated (i.e. contain one or more double bonds). When a heterocycloalkyl group contains the prefix $C_{n1-n2}$ this prefix indicates the number of carbon atoms in the corresponding carbocyclic group, in which one or more, suitably 1 to 5, of the ring atoms is replaced with a heteroatom as defined above.

The term "heteroaryl" as used herein, whether it is used alone or as part of another group, refers to cyclic groups containing at least one heteroaromatic ring containing 5, 6, 8, 9 or 10 atoms in which one or more of the atoms are a heteroatom selected from O, S and N and the remaining atoms are C. When a heteroaryl group contains the prefix $C_{n1-n2}$ this prefix indicates the number of carbon atoms in the corresponding carbocyclic group, in which one or more, suitably 1 to 5, of the ring atoms is replaced with a heteroatom as defined above.

All cyclic groups, including aryl and cyclo groups, contain one or more than one ring (i.e. are polycyclic). When a cyclic group contains more than one ring, the rings may be fused, bridged, spirofused or linked by a bond.

The term "fluorosubstituted" refers to the substitution of one or more, including all, available hydrogens in a referenced group with fluorine.

The term "available", as in "available hydrogen atoms" or "available atoms" refers to atoms that would be known to a person skilled in the art to be capable of replacement by a substituent.

The term "salt" means an acid addition salt or a basic addition salt. The term "salts" embraces salts commonly used to form addition salts of free acids or free bases and those compatible with the treatment of plants.

The term "solvate" as used herein means a compound, or a salt or prodrug of a compound, wherein molecules of a suitable solvent are incorporated in the crystal lattice. A suitable solvent is physiologically tolerable at the dosage administered The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas).

The term "abscisic acid" (ABA) refers to a compound having the IUPAC name: (2Z,4E)-5-[(1S)-1-hydroxy-2,6,6-trimethyl-4-oxocyclohex-2-en-1-yl]-3-methylpenta-2,4-dienoic acid and having the chemical formula:

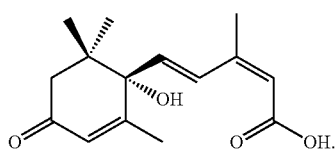

The term "1001" refers to a compound having the IUPAC name: (2Z,4E)-5-((S)-(1-hydroxy-6-(3-hydroxypropoxy)-2,2-dimethyl-4-oxo-1,2,3,4-tetrahydronaphthalen-1-yl)-3-methylpenta-2,4-dienoic acid and having the chemical formula:

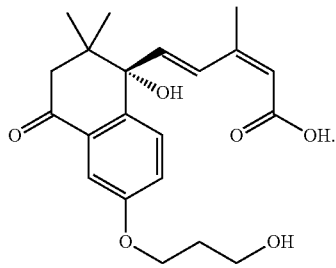 [SMILES: CC(=C/C(=O)O)/C=C/[C@@]1(O)c2ccc(OCCCO)cc2C(=O)CC1(C)C]

The term "1002" refers to a compound having the IUPAC name: (2Z,4E)-5-(S)-(3-(hexylthio)-1-hydroxy-2,6,6-trimethyl-4-oxocyclohex-2-en-1-yl)-3-methylpenta-2,4-dienoic acid and having the chemical formula:

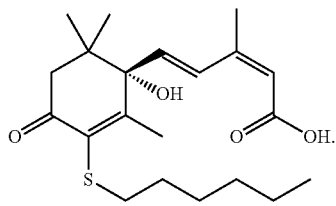 [SMILES: CCCCCCSC1=C(C)[C@](O)(/C=C/C(C)=C\C(=O)O)C(C)(C)CC1=O]

As used herein, the term "effective amount" means an amount effective, at dosages and for periods of time, necessary to achieve a desired result.

The term "desired result" as used herein is any positive effect on plant grown and development.

When used, for example, with respect to the methods of treatment, uses, and compositions of the application, a plant, for example a plant "in need thereof" is a cell, seed, part of a plant or plant in which ABA plays a role in plant growth and development The term "administered" as used herein means administration of a therapeutically effective amount of one or more compounds or compositions of the application and/or one or more compounds of Formula (II) or enantiomers, salts and/or solvates thereof, to a cell, seed or to a plant.

The term "ABA antagonist" as used herein means a compound that inhibits a negative response to ABA signaling in a plant.

The term "ABA response" as used herein means a response that has a negative or undesirable impact on plant growth and development as a result of the presence of ABA in the plant, including endogenously produced ABA or ABA from an external source.

The term "reduce" or "reducing" as used herein with respect to the adverse affects of an ABA response refers to any decrease in adverse affects of an ABA response compared a control, such as otherwise identical conditions except in the absence of one or more compounds of the application and/or one or more compounds of Formula II, or enantiomers, salts and/or solvates thereof.

The term "ABA producing plant pathogen" as used herein means a plant pathogen that elicits an ABA response in a plant, including by inducing ABA production by the plant and providing an external source of ABA.

The term "ABA producing plant pathogen infection" or refers to an invasion of plant cells by a foreign undesirable ABA producing plant pathogen.

The terms "to treat", "treating" and "treatment" as used herein and as is well understood in the art, means an approach for obtaining beneficial or desired results, including clinical results. Beneficial or desired clinical results include, but are not limited to, diminishment of extent of infection, stabilization (i.e. not worsening) of the state of the ABA producing plant pathogen infection, preventing spread of the ABA producing plant pathogen infection, delay or slowing of infection progression, amelioration or palliation of the ABA producing plant pathogen infectious state, diminishment of the reoccurrence of ABA producing plant pathogen infection, diminishment, stabilization, alleviation or amelioration of one or more diseases, disorders or conditions arising from the ABA producing plant pathogen infection, diminishment of the reoccurrence of one or more diseases, disorders or conditions arising from the ABA producing plant pathogen infection, and remission of the ABA producing plant pathogen infection and/or one or more symptoms or conditions arising from the ABA producing plant pathogen infection, whether partial or total, whether detectable or undetectable. "To treat", "treating" and "treatment" can also mean prolonging survival as compared to expected survival if not receiving treatment. "To treat", "treating" and "treatment" as used herein also include prophylactic treatment. For example, a plant with an early ABA producing plant pathogen infection is treated to prevent progression, or alternatively a plant in remission is treated to prevent recurrence.

"Palliating" an infection, disease, disorder and/or condition means that the extent and/or undesirable manifestations of an infection, disease, disorder and/or condition are lessened and/or time course of the progression is slowed or lengthened, as compared to not treating the infection, disease, disorder and/or condition.

The term "prevention" or "prophylaxis" and the like as used herein, refers to a reduction in the risk or probability of a plant becoming afflicted with a ABA producing plant pathogen infection and/or a disease, disorder and/or condition arising from a ABA producing plant pathogen infection or manifesting a symptom associated with a ABA producing plant pathogen infection and/or a disease, disorder and/or condition arising from a ABA producing plant pathogen infection.

The term "composition" as used herein refers to a composition of matter for plant-based use.

The term "plant" as used herein refers to any species or genera of plant in which ABA signaling plays a role in regulating plant development.

II. Compounds and Compositions of the Application

The present application describes a novel class of 3'-unsaturated ABA derivatives that can regulate plant growth, and that are relatively straightforward and inexpensive to prepare.

Accordingly, the present application includes a compound of Formula (I) or an enantiomer, salt, and/or solvate thereof:

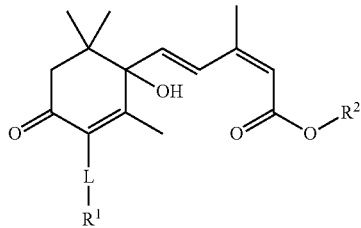

(I)

wherein
L is —C=C— or —C≡C—;
$R^1$ is $C_{1-10}$alkyl, $C_{2-10}$alkenyl, $C_{2-10}$alkynyl, $(CH_2)_{0-2}$ $C_{3-10}$cycloalkyl, $(CH_2)_{0-2}$aryl, $(CH_2)_{0-2}$heterocycloalkyl, or $(CH_2)_{0-2}$heteroaryl, each being optionally substituted with one or more of halo, CN, OH, $NH_2$, $C_{1-10}$alkyl, $C_{2-10}$alkenyl, $C_{2-10}$alkynyl, $NH(C_{1-6}$alkyl), $N(C_{1-6}$alkyl)($C_{1-6}$alkyl), $OC_{1-6}$alkyl, $OC_{2-6}$alkenyl, $OC_{2-6}$alkynyl, $(CH_2)_{0-2}C_{3-10}$ cycloalkyl, $(CH_2)_{0-2}$aryl, $(CH_2)_{0-2}$heterocycloalkyl, $(CH_2)_{0-2}$heteroaryl, O$(CH_2)_{0-2}C_{3-10}$cycloalkyl, $O(CH_2)_{0-2}$aryl, $O(CH_2)_{0-2}$heterocycloalkyl, or $O(CH_2)_{0-2}$heteroaryl, the latter 16 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl; and
$R^2$ is H, $C_{1-10}$alkyl, $C_{2-10}$alkenyl, $C_{2-10}$alkynyl, cycloalkyl, aryl, heterocycloalkyl or heteroaryl, the latter 7 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl,
wherein each alkyl, alkenyl, and alkynyl are optionally fluorosubstituted.

The present application also includes a compound of Formula (I) or an enantiomer, salt, and/or solvate thereof:

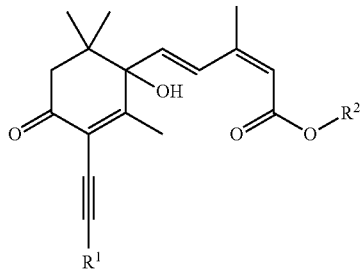

I wherein
$R^1$ is $C_{1-10}$alkyl, $C_{2-10}$alkenyl, $C_{2-10}$alkynyl, $(CH_2)_{0-2}$ $C_{3-10}$cycloalkyl, $(CH_2)_{0-2}$aryl, $(CH_2)_{0-2}$heterocycloalkyl, or $(CH_2)_{0-2}$heteroaryl, each being optionally substituted with one or more of halo, CN, OH, $NH_2$, $C_{1-10}$alkyl, $C_{2-10}$alkenyl, $C_{2-10}$alkynyl, $NH(C_{1-6}$alkyl), $N(C_{1-6}$alkyl)($C_{1-6}$alkyl), $OC_{1-6}$alkyl, $OC_{2-6}$alkenyl, $OC_{2-6}$alkynyl, $(CH_2)_{0-2}C_{3-10}$cycloalkyl, $(CH_2)_{0-2}$aryl, $(CH_2)_{0-2}$heterocycloalkyl, $(CH_2)_{0-2}$heteroaryl, O $(CH_2)_{0-2}C_{3-10}$cycloalkyl, $O(CH_2)_{0-2}$aryl, $O(CH_2)_{0-2}$heterocycloalkyl, or $O(CH_2)_{0-2}$heteroaryl, the latter 16 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl; and
$R^2$ is H, $C_{1-10}$alkyl, $C_{2-10}$alkenyl, $C_{2-10}$alkynyl, cycloalkyl, aryl, heterocycloalkyl or heteroaryl, the latter 7 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl,
wherein each alkyl, alkenyl, and alkynyl are optionally fluorosubstituted.

In an embodiment, $R^1$ is $(CH_2)_{0-2}$aryl optionally substituted with one or more of halo, CN, OH, $NH_2$, $C_{1-10}$alkyl, $C_{2-10}$alkenyl, $C_{2-10}$alkynyl, $NH(C_{1-6}$alkyl), $N(C_{1-6}$alkyl)($C_{1-6}$alkyl), $OC_{1-6}$alkyl, $OC_{2-6}$alkenyl, $OC_{2-6}$alkynyl, $(CH_2)_{0-2}C_{3-10}$cycloalkyl, $(CH_2)_{0-2}$aryl, $(CH_2)_{0-2}$heterocycloalkyl, $(CH_2)_{0-2}$heteroaryl, $O(CH_2)_{0-2}C_{3-10}$ cycloalkyl, $O(CH_2)_{0-2}$aryl, $O(CH_2)_{0-2}$heterocycloalkyl or $O(CH_2)_{0-2}$heteroaryl, the latter 16 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl, wherein each alkyl, alkenyl, and alkynyl are optionally fluorosubstituted.

In an embodiment, $R^1$ is $(CH_2)_{0-2}$aryl optionally substituted with one or more of halo, CN, OH, $NH_2$, $C_{1-10}$alkyl, $OC_{1-6}$alkyl, $(CH_2)_{0-2}C_{3-10}$cycloalkyl, $(CH_2)_{0-2}$aryl, $(CH_2)_{0-2}$heterocycloalkyl, $(CH_2)_{0-2}$heteroaryl, $O(CH_2)_{0-2}$ $C_{3-10}$cycloalkyl, $O(CH_2)_{0-2}$aryl, $O(CH_2)_{0-2}$heterocycloalkyl or $O(CH_2)_{0-2}$heteroaryl, the latter 10 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl, wherein each alkyl, alkenyl, and alkynyl are optionally fluorosubstituted.

In an embodiment, $R^1$ is aryl optionally substituted with one or more of OH, halo, $C_{1-10}$alkyl, $OC_{1-6}$alkyl, or O $(CH_2)_{0-2}$aryl, wherein each alkyl, alkenyl, and alkynyl are optionally fluorosubstituted.

In an embodiment, $R^1$ is aryl optionally substituted with one or more of halo, $C_{1-10}$alkyl, $OC_{1-6}$alkyl, or $O(CH_2)_{0-2}$ aryl, wherein each alkyl, alkenyl, and alkynyl are optionally fluorosubstituted.

In an embodiment, $R^1$ is aryl. In an embodiment, $R^1$ is aryl substituted with one or more OH. In an embodiment, $R^1$ is aryl substituted with $O(CH_2)_{0-2}$aryl. In an embodiment, $R^1$ is aryl substituted with one or more halo. In an embodiment, $R^1$ is aryl substituted with one or more fluoro.

In an embodiment, $R^1$ is aryl substituted with $C_{1-10}$alkyl, wherein alkyl is optionally fluorosubstituted. In an embodiment, $R^1$ is aryl substituted with one or more of methyl, ethyl or $CF_3$.

In an embodiment, $R^1$ is aryl substituted with $OC_{1-6}$alkyl, wherein alkyl is optionally fluorosubstituted. In an embodiment, $R^1$ is aryl substituted with one or more of $OCH_3$ or $OCF_3$.

In an embodiment, $R^1$ is $C_{1-10}$alkyl optionally substituted with one or more of halo, CN, OH, $NH_2$, $C_{1-10}$alkyl, $C_{2-10}$alkenyl, $C_{2-10}$alkynyl, $NH(C_{1-6}$alkyl), $N(C_{1-6}$alkyl)

($C_{1-6}$alkyl), $OC_{1-6}$alkyl, $OC_{2-6}$alkenyl, $OC_{2-6}$alkynyl, $(CH_2)_{0-2}C_{3-10}$ cycloalkyl, $(CH_2)_{0-2}$aryl, $(CH_2)_{0-2}$heterocycloalkyl, $(CH_2)_{0-2}$heteroaryl, $O(CH_2)_{0-2}C_{3-10}$cycloalkyl, $O(CH_2)_{0-2}$aryl, $O(CH_2)_{0-2}$heterocycloalkyl, or $O(CH_2)_{0-2}$heteroaryl, the latter 16 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl, wherein each alkyl, alkenyl, and alkynyl are optionally fluorosubstituted.

In an embodiment, $R^1$ is $C_{1-10}$alkyl optionally substituted with one or more of halo, CN, OH, $NH_2$, $C_{1-10}$alkyl, $C_{2-10}$alkenyl, or $C_{2-10}$alkynyl, wherein each alkyl, alkenyl, and alkynyl are optionally fluorosubstituted.

In an embodiment, $R^1$ is $C_{1-10}$alkyl substituted with one or more of OH and $C_{1-10}$alkyl, wherein alkyl is optionally fluorosubstituted.

In an embodiment, $R^1$ is $C_{2-10}$alkenyl optionally substituted with one or more of halo, CN, OH, $NH_2$, $C_{1-10}$alkyl, $C_{2-10}$alkenyl, $C_{2-10}$alkynyl, $NH(C_{1-6}$alkyl), $N(C_{1-6}$alkyl)($C_1$-6alkyl), $OC_{1-6}$alkyl, $OC_{2-6}$alkenyl, $OC_{2-6}$alkynyl, $(CH_2)_{0-2}C_{3-10}$cycloalkyl, $(CH_2)_{0-2}$aryl, $(CH_2)_{0-2}$heterocycloalkyl, $(CH_2)_{0-2}$heteroaryl, $O(CH_2)_{0-2}C_{3-10}$cycloalkyl, $O(CH_2)_{0-2}$aryl, $O(CH_2)_{0-2}$heterocycloalkyl, or $O(CH_2)_{0-2}$heteroaryl, the latter 16 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl, wherein each alkyl, alkenyl, and alkynyl are optionally fluorosubstituted.

In an embodiment, $R^1$ is $C_{2-10}$alkenyl optionally substituted with one or more of halo, CN, OH, $NH_2$, $C_{1-10}$alkyl, $C_{2-10}$alkenyl, or $C_{2-10}$alkynyl, wherein each alkyl, alkenyl, and alkynyl are optionally fluorosubstituted.

In an embodiment, $R^1$ is $C_{2-6}$alkenyl substituted with one or more of OH and $C_{1-10}$alkyl, wherein alkyl is optionally fluorosubstituted. In an embodiment, $R^1$ is $(CH_2)_{0-2}C_{3-10}$cycloalkyl optionally substituted with one or more of halo, CN, OH, $NH_2$, $C_{1-10}$alkyl, $C_{2-10}$alkenyl, $C_{2-10}$alkynyl, $NH(C_{1-6}$alkyl), $N(C_{1-6}$alkyl)($C_{1-6}$alkyl), $OC_{1-6}$alkyl, $OC_{2-6}$alkenyl, $OC_{2-6}$alkynyl, $(CH_2)_{0-2}C_{3-10}$cycloalkyl, $(CH_2)_{0-2}$aryl, $(CH_2)_{0-2}$heterocycloalkyl, $(CH_2)_{0-2}$heteroaryl, $O(CH_2)_{0-2}C_{3-10}$cycloalkyl, $O(CH_2)_{0-2}$aryl, $O(CH_2)_{0-2}$heterocycloalkyl, or $O(CH_2)_{0-2}$heteroaryl, the latter 16 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl, wherein each alkyl, alkenyl, and alkynyl are optionally fluorosubstituted.

In an embodiment, $R^1$ is $C_{3-10}$cycloalkyl. In an embodiment, $R^1$ is $C_{3-10}$cycloalkyl optionally substituted with one or more of halo, CN, OH, $NH_2$, $C_{1-10}$alkyl, $C_{2-10}$alkenyl, or $C_{2-10}$alkynyl, wherein each alkyl, alkenyl, and alkynyl are optionally fluorosubstituted.

In an embodiment, $R^2$ is H or $C_{1-10}$alkyl. In an embodiment, $R^2$ is H or $CH_3$.

In an embodiment, L is —C═C—. In an embodiment, L is —C≡C—.

In an embodiment, the compounds of Formula (I) have the following stereochemistry:

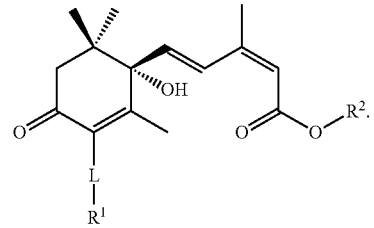

In an embodiment, the compounds of Formula (I) wherein L is —C═C have the following stereochemistry:

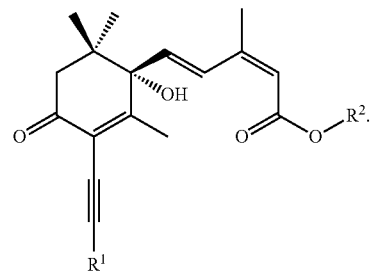

In an embodiment, the compound of Formula (I) is selected from the compounds listed below:

| Compound I.D | Example # | Structures |
|---|---|---|
| 1018 | 1 | 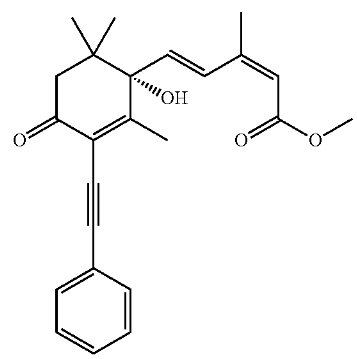 [SMILES: COC(=O)/C=C(C)\C=C\[C@@]1(O)C(C)=C(C#Cc2ccccc2)C(=O)CC1(C)C] |
| 1019 | 2 | 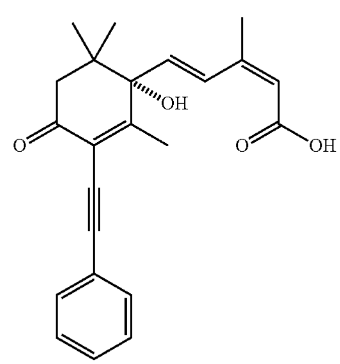 [SMILES: CC1=C(C#Cc2ccccc2)C(=O)CC(C)(C)[C@@]1(O)/C=C/C(C)=C\C(=O)O] |

| Compound I.D | Example # | Structures |
|---|---|---|
| 1021 | 3 | 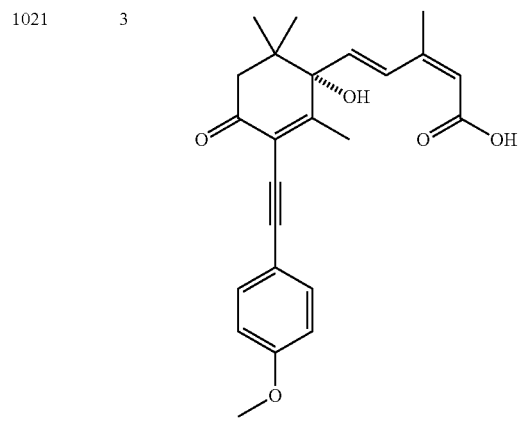 |
| 1022 | 4 | 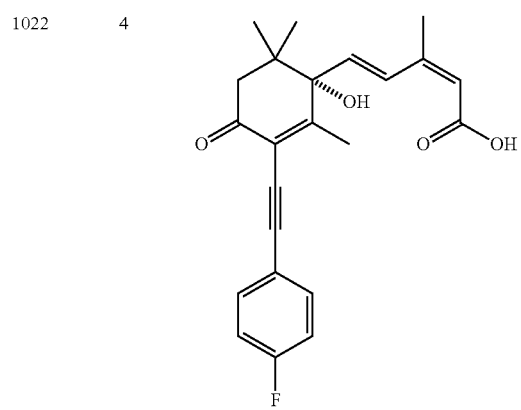 |
| 1023 | 5 | 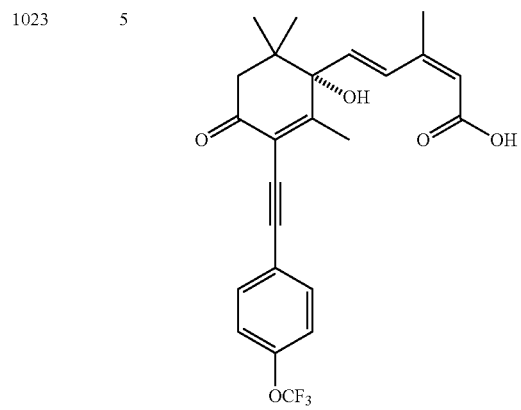 |
| 1024 | 6 | 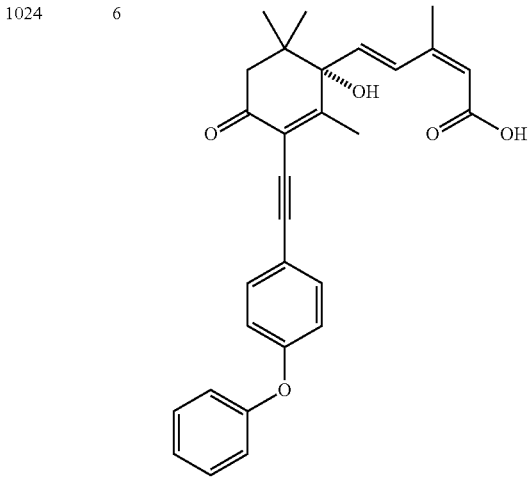 |
| 1025 | 7 | 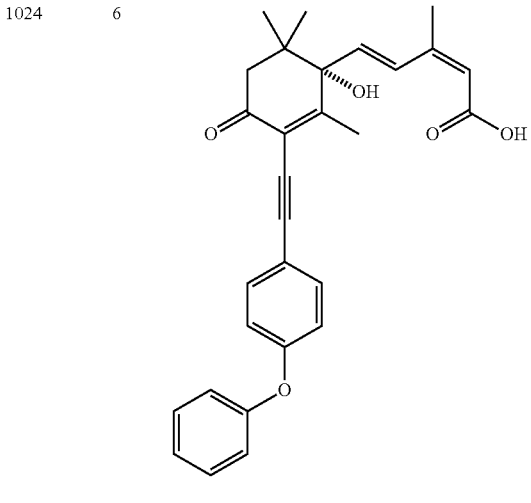 |
| 1059 | 8 | 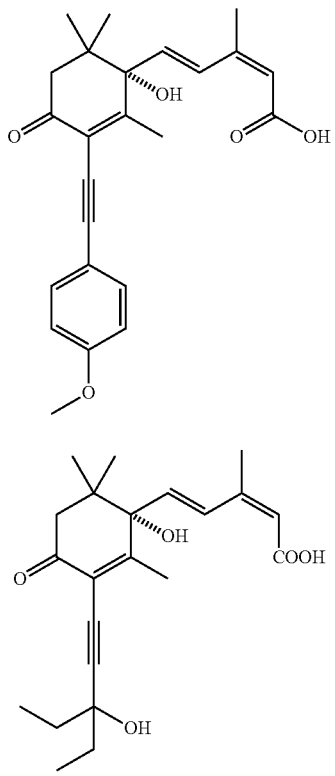 |
| 1063 | 9 | 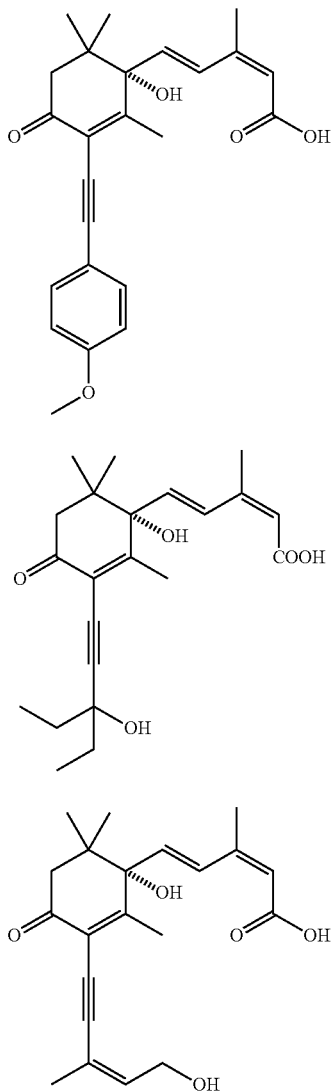 |

-continued

| Compound I.D | Example # | Structures |
|---|---|---|
| 1090 | 10 | 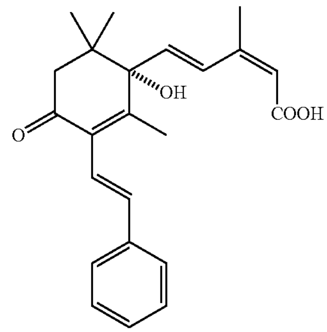 [SMILES: CC1=C(/C=C/c2ccccc2)C(=O)CC(C)(C)[C@@]1(O)/C=C/C(C)=C\C(=O)O] |
| 1091 | 11 | 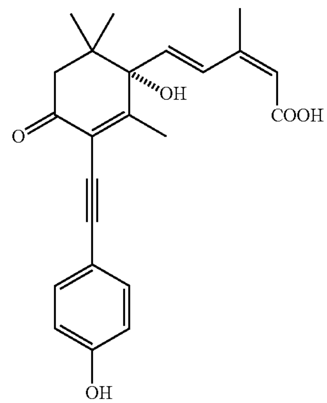 [SMILES: CC1=C(C#Cc2ccc(O)cc2)C(=O)CC(C)(C)[C@@]1(O)/C=C/C(C)=C\C(=O)O] |
| 1100 | 12 | | or a salt, and/or solvate thereof.

In an embodiment the salt is an acid addition salt or a base addition salt.

The selection of a suitable salt may be made by a person skilled in the art (see, for example, S. M. Berge, et al., "Pharmaceutical Salts," J. Pharm. Sci. 1977, 66, 1-19).

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. The selection of the appropriate salt may be useful, for example, so that an ester functionality, if any, elsewhere in a compound is not hydrolyzed. The selection criteria for the appropriate salt will be known to one skilled in the art.

In an embodiment the salt is a base addition salt.

Solvates of compounds of the application include, for example, those made with solvents that are pharmaceutically acceptable. Examples of such solvents include water (resulting solvate is called a hydrate) and ethanol and the like.

The compounds of the present application are suitably formulated in a conventional manner into compositions using one or more carriers. Accordingly, the present application also includes a composition comprising one or more compounds of the application and a carrier. In an embodiment, the carrier is any carrier compatible or suitable for agricultural use, such as water.

A compound of the application including salts and/or solvates thereof is suitably used on their own but will generally be administered in the form of a composition in which the one or more compounds of the application (the active ingredient) is in association with an acceptable carrier. Depending on the mode of administration, the composition will comprise from about 0.05 wt % to about 99 wt % or about 0.10 wt % to about 70 wt %, of the active ingredient, and from about 1 wt % to about 99.95 wt % or about 30 wt % to about 99.90 wt % of an acceptable carrier, all percentages by weight being based on the total composition.

A compound of the application is either used alone or in combination with other known agents useful for regulating plant development. When used in combination with other agents useful for regulating plant development, it is an embodiment that a compound of the application is administered contemporaneously with those agents. As used herein, "contemporaneous administration" of two substances to a subject means providing each of the two substances so that they are both active in the subject at the same time.

In an embodiment, the other agent is a plant growth regulator.

In an embodiment, the other agent is an agricultural product.

In the above, the term "a compound" also includes embodiments wherein one or more compounds are referenced.

III. Methods and Uses of the Application

The compounds of the application have been shown to reduce adverse effects of an ABA response in a plant. In particular, it has surprisingly been shown that the compounds of the application can reduce adverse effects of an ABA response in seeds such as lentil seeds, soybean seeds, canary seed, wheat seed, canola seed, rice seed, barley seed, and sorghum seed and promote germination. It has further been surprisingly shown that the compounds of the application can reduce adverse effects of an ABA response arising from an ABA producing plant pathogen infection, such as an infection from *Botrytis cinerea*. In an embodiment, the compounds of the application act as ABA antagonists.

Accordingly, the present application includes a method for reducing adverse effects of an ABA response in a plant in need thereof comprising administering an effective amount of one or more compounds of the application to the plant. The application also includes a use of one or more compounds of the application for reducing adverse effects of an ABA response in a plant. The application further includes one or more compounds of the application for use to reduce adverse effects of an ABA response in a plant.

In an embodiment, the plant is a canola, soybean, canary, sorghum, lentil, chickpea, *Arabidopsis*, faba bean, soybean, corn, rice, wheat, rye, barley, or fruit plant.

In an embodiment, the plant is a canola, lentil, chickpea, *Arabidopsis*, faba bean, soybean, corn, rice, wheat, rye, barley, or fruit plant.

In an embodiment, the plant is a lentil, soybean, canary, wheat, canola, rice, barley, or sorghum plant.

In an embodiment, the fruit plant is table or wine grapes.

In an embodiment, the fruit plant is a stone fruit plant. In an embodiment, the stone fruit plant is apricot, cherry, peach or plum.

In an embodiment, the fruit plant is strawberry, blueberry, raspberry, or blackberry.

In an embodiment, the fruit plant is pome fruit. In an embodiment, the pome fruit is apple, pear, or cherry.

In an embodiment, fruit plant is eggplant, pepper, or tomato.

In an embodiment, the fruit plant is cucurbit. In an embodiment, the curcubit is cucumber, pumpkin, muskmelon, squash, or zucchini.

In an embodiment, the fruit plant is a tree nut plant. In an embodiment, the tree nut plant is walnut, chestnut, or hickory.

In an embodiment, the plant is leafy vegetable, or pasture and turf grass.

In an embodiment, the plant is oat, flax, mustard, ornamental, or sugar cane.

In an embodiment, the methods and uses of the application comprise contacting the seed of the plant with an effective amount of the compound of the application or salt and/or solvate thereof.

In an embodiment, a reduction in adverse affects of an ABA response includes, but is not limited to, delayed or inhibited seed germination and/or plant dessication, over-ripening of fruit, slow bud breaking and/or slow plant growth, for example, reduced or inhibited seedling growth, delayed or inhibited plant emergence, and/or reduced or inhibited plant flowering. In an embodiment, the reduction in adverse affects of an ABA response occur under stress conditions, such as cold hear or high salt. In an embodiment, the compounds of the application promote germination of seeds under stress conditions, overcoming seed-produced ABA that slows germination. In an embodiment, the compounds delay over ripening of fruit and hasten bud break inhibited by cool conditions, and/or promote growth of plants under stress conditions.

In the context of reducing adverse affects of an ABA response, an effective amount of the compound of the application or a salt and/or solvate thereof, is an amount that, for example, reduces the adverse affects compared to the negative response without administration of the compound of the application, or a salt and/or solvate thereof.

In an embodiment, the ABA response arises from an ABA producing plant pathogen infection.

In an embodiment, the ABA producing plant pathogen is a fungus, bacterium, protist, nematode or virus. In an embodiment, the ABA producing plant pathogen is a fungus. In an embodiment, the fungus is *Botrytis cinerea* or *Cercospera* spp. In an embodiment, the fungus is *Botrytis cinerea*.

In an embodiment, the ABA producing plant pathogen is a bacterium. In an embodiment, the bacterium is *Xanthomonas oryzae* pv *oryzae* or *Xanthomonas translucens*.

It would be appreciated by the skilled person that *Xanthomonas oryzae* pv *oryzae* promotes leaf blight, for example, in rice (Xu et al 2013)[22], and *Xanthomonas translucens* promotes leaf streak, for example in wheat (Peng et al 2019)[11].

In an embodiment, the effective amount of the compound of the application or a salt and/or solvate thereof to be administered to the plant is about 0.1 μM to about 600 μM, about 1 μM to about 500 μM, or about 5 μM to about 250 μM.

It has been shown that compounds of the application can reduce adverse effects of an ABA response arising from an infection of an ABA producing plant pathogen such as *Botrytis cinerea*. Accordingly, the present application also includes a method for treating or preventing an ABA producing plant pathogen infection in a plant in need thereof comprising administering an effective amount of one or more compounds of the application to the plant.

The application also includes a use of one or more compounds of the application for treating or preventing an ABA producing plant pathogen infection in a plant. The application further includes one or more compounds of the application for use for treating or preventing an ABA producing plant pathogen infection in a plant.

The present application also includes a method for treating or preventing a disease, disorder or condition in a plant arising from an ABA producing plant pathogen infection comprising administering an effective amount of one or more compounds of the application to a plant in need thereof.

The application also includes a use of one or more compounds of the application for treating or preventing a disease, disorder or condition arising from an ABA producing plant pathogen infection in a plant. The application further includes one or more compounds of the application for use for treating or preventing a disease, disorder or condition arising from an ABA producing plant pathogen infection in a plant.

It has further been surprisingly shown that compounds of Formula (II) can also reduce adverse effects of an ABA response, for example, in seeds such as lentil seeds. Therefore, in an embodiment, the compounds of Formula (II) also act as ABA antagonists.

Accordingly, the present application also includes a method for reducing adverse effects of an ABA response in a plant in need thereof comprising administering an effective amount of one or more compounds of the Formula (II) or an enantiomer, salt, and/or solvate thereof, to the plant,

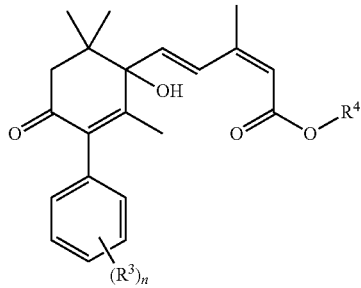

(II)

wherein:

n is 0, 1, 2, or 3;

$R^3$ is selected from OH, halo, $C_{1-10}$alkyl, $OC_{1-6}$alkyl, and $O(CH_2)_{0-2}$aryl, the latter 3 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl; and $R^4$ is selected from H or $C_{1-10}$alkyl, wherein each alkyl, alkenyl, and alkynyl is optionally fluorosubstituted.

The application also includes a use of one or more compounds of Formula (II) for reducing adverse effects of an ABA response in a plant. The application further includes one or more compounds of Formula (II) for use to reduce adverse effects of an ABA response in a plant.

In an embodiment is 0, 1 or 2. In an embodiment n is 0 or 1. In an embodiment n is 0.

In an embodiment, $R^3$ is not present (i.e. n is 0). In an embodiment, $R^3$ is selected from OH, halo, $C_{1-10}$alkyl, and $OC_{1-6}$alkyl, wherein each alkyl is optionally fluorosubstituted.

In an embodiment, $R^3$ is selected from Br, $C_1$ and F. In an embodiment, $R^3$ is F.

In an embodiment, $R^3$ is selected from $CH_3$, $CH_2CH_3$, $OCH_3$, and $OCH_2CH_3$, wherein each alkyl is optionally fluorosubstituted. In an embodiment, $R^3$ is selected from $CH_3$, $OCH_3$, $CHF_2$, $OCHF_2$, $CH_2F$, $OCH_2F$, $CF_3$ and $OCF_3$. In an embodiment, $R^3$ is selected from $OCH_3$ and $OCF_3$.

In an embodiment, $R^3$ is $(CH_2)_{0-2}$aryl optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl, wherein each alkyl, alkenyl, and alkynyl are optionally fluorosubstituted. In an embodiment, $R^3$ is $(CH_2)_{0-2}$aryl optionally substituted with one or more of halo, OH, $NH_2$, $C_{1-6}$alkyl, and $OC_{1-6}$alkyl, wherein each alkyl, alkenyl, and alkynyl are optionally fluorosubstituted. In an embodiment, $R^3$ is $(CH_2)_{0-2}$aryl.

In an embodiment, $R^3$ is in the para position on the phenyl ring.

In an embodiment, $R^4$ is H or $CH_3$.

In an embodiment, the plant is a canola, soybean, canary, sorghum, lentil, chickpea, *Arabidopsis*, faba bean, soybean, corn, rice, wheat, rye, barley, or fruit plant.

In an embodiment, the plant is a canola, lentil, chickpea, *Arabidopsis*, faba bean, soybean, corn, rice, wheat, rye, barley, or fruit plant.

In an embodiment, the plant is a lentil, soybean, canary, wheat, canola, rice, barley, or sorghum plant.

In an embodiment, the fruit plant is table or wine grapes.

In an embodiment, the fruit plant is a stone fruit plant. In an embodiment, the stone fruit plant is apricot, cherry, peach or plum.

In an embodiment, the fruit plant is strawberry, blueberry, raspberry, or blackberry.

In an embodiment, the fruit plant is pome fruit. In an embodiment, the pome fruit is apple, pear, or cherry.

In an embodiment, fruit plant is eggplant, pepper, or tomato.

In an embodiment, the fruit plant is cucurbit. In an embodiment, the curcubit is cucumber, pumpkin, muskmelon, squash, or zucchini.

In an embodiment, the fruit plant is a tree nut plant. In an embodiment, the tree nut plant is walnut, chestnut, or hickory.

In an embodiment, the plant is leafy vegetable, or pasture and turf grass.

In an embodiment, the plant is oat, flax, mustard, ornamental, or sugar cane.

In the context of reducing adverse affects of an ABA response, an effective amount of the compound of Formula II or an enantiomer, salt and/or solvate thereof, is an amount that, for example, reduces the adverse affects compared to the negative response without administration of the compound of Formula II, or an enantiomer, salt and/or solvate thereof.

In an embodiment, the effective amount of the compound of Formula II is about 0.1 μM to about 600 μM, about 1 μM to about 500 μM, or about 5 μM to about 250 μM.

In an embodiment, the ABA response arises from an ABA producing plant pathogen infection.

In an embodiment, the compound of the application or salt and/or solvate thereof and/or compound of Formula (II) or enantiomer, salt and/or solvate thereof, is administered to the plant in a composition that is diluted prior to use. In an embodiment that composition is an aqueous solution. In an embodiment, the composition further comprises other ingredients common to agricultural products, such as, but not limited to, fertilizers, wetting agents, stickers/spreaders and surfactants.

In an embodiment, the compound of the application or salt and/or solvate thereof or compound of Formula (II) or enantiomer, salt and/or solvate thereof, is applied to plants at any suitable rate, the selection of which can be made by a person skilled in the art. Factors to consider include, for example, the identity and/or the age of the plant, the concentration of the composition of the application and/or a combination thereof.

In an embodiment, the seed of the plant is contacted with the composition of the application.

It will also be appreciated that the effective amount of a composition of the application used for the administration or use may increase or decrease over the course of a particular regime. In some instances, chronic administration or use is required. For example, the composition of the application is administered or used in an amount and for a duration sufficient to regulate plant growth.

IV. Methods of Preparing the Compounds of the Application

Compounds of the present application or compounds of Formula (II) or enantiomer, salt and/or solvate thereof, can be prepared by various synthetic processes. The choice of particular structural features and/or substituents may influence the selection of one process over another. The selection of a particular process to prepare a given compound of Formula (I) or Formula (II) is within the purview of the person of skill in the art. Some starting materials for preparing compounds of the present application are available from commercial chemical sources. Other starting materials, for example as described below, are readily prepared from available precursors using straightforward transformations that are well known in the art. In the Schemes below showing the preparation of compounds of the application, all variables are as defined in Formula (I), unless otherwise stated, In an embodiment, the compounds of Formula (I) wherein L is —C≡C— are prepared as shown in Scheme 1. Therefore, an ABA derivative of Formula A in which X is a suitable leaving group such as iodide is coupled with an appropriate alkynyl compound of Formula B in a solvent such as tetrahydrofuran (THF) and in the presence of a catalyst such as tetrakis(triphenylphosphine)palladium(0) and cocatalyst such as copper iodide and a base such as triethylamine. In an embodiment, the reactants and solvent are combined at room temperature (rt) and then reacted at a higher temperature such as at about 95° C. or at about 100° C. In an embodiment, the reaction is carried out under an inert atmosphere, such as under argon.

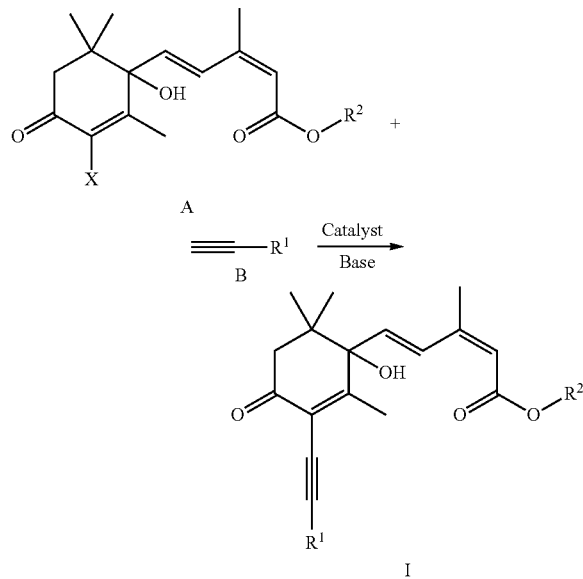

In an embodiment, the compounds of Formula (I)I wherein L is —C≡C— or compounds of Formula (II) or enantiomer, salt and/or solvate thereof, are prepared as shown in Scheme 2. Therefore, an ABA derivative of Formula A in which X is a suitable leaving group such as iodide is coupled with a suitable aryl-boronic acid compound of Formula C in a solvent such as a 9:1 mixture of tetrahydrofuran (THF) and water (H$_2$O) and in the presence of a catalyst such as tetrakis(triphenylphosphine)palladium (0) and a base such as potassium carbonate. In an embodiment, the reactants and solvent are combined at room temperature (rt) and then reacted at a higher temperature such as at about 90° C. In an embodiment, the reaction is carried out under an inert atmosphere, such as under argon.

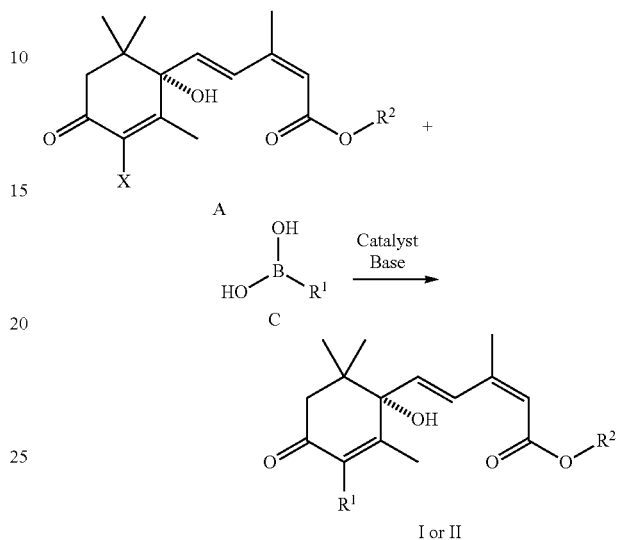

A person of skill in the art would appreciate that a stereoisomer of a compound of Formula (I) or Formula (II), can also be prepared as shown in Scheme 1 or Scheme II starting with a compound of Formula A with the appropriate stereospecificity to provide the desired stereoisomer of the compound of Formula (I) or Formula (II).

The ABA derivative of formula A can be synthesized through known methods, for example, using the synthetic procedures found in Arai, S. et al. 1999.

The alkynyl derivatives of Formula B or salts and/or solvates thereof, useful in the present application are available from commercial sources or can be prepared using methods known in the art.

The aryl-boronic acid compound of Formula C or salts and/or solvates thereof, useful in the present application are available from commercial sources or can be prepared using methods known in the art.

The ABA antagonist 1001 can be synthesized through known methods, for example, using the synthetic procedures found in Rajagopalan et al. 2016.

The ABA antagonist 1002 can be synthesized through known methods, for example, using the synthetic procedures found in Takeuchi et al 2014.

The formation of a desired compound salt is achieved using standard techniques. For example, the neutral compound is treated with an acid or base in a suitable solvent and the formed salt is isolated by filtration, extraction or any other suitable method.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art. Examples of suitable solvents are ethanol, water and the like. When water is the solvent, the molecule is referred to as a "hydrate". The formation of solvates of the compounds of the application or compounds of Formula (II) will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Throughout the processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

EXAMPLES

The following non-limiting examples are illustrative of the present application.

Example 1: Methyl (2Z,4E)-5-((S)-1-Hydroxy-2,6,6-trimethyl-4-oxo-3-(phenylethynyl)cyclohex-2-en-1-yl)-3-methylpenta-2,4-dienoate (1018)

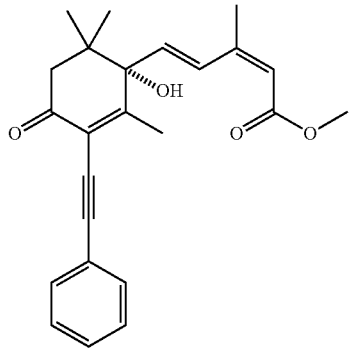 [SMILES: COC(=O)/C=C(C)\C=C\[C@@]1(O)C(C)=C(C#Cc2ccccc2)C(=O)CC1(C)C]

Under argon, 3'-iodo-(S)-ABA methyl ester (Arai et al. 1999) (193.5 mg, 0.48 mmol), tetrakis(triphenylphosphine)palladium (0) (273.5 mg, 0.24 mmol) and copper (1) iodide (46 mg, 0.24 mmol) were transferred into a RBF and sequentially were added THF (5.0 mL), triethylamine (5.0 mL) and ethynylbenzene (0.080 mL, 0.73 mmol) at rt. The flask was placed in an oil bath at 100° C. After stirring for 2 hours, the reaction was allowed to come to ambient temperature and diluted with ethyl acetate. The organic phase was washed with 1.2 M HCl twice, water once, brine once, dried over $Na_2SO_4$ and concentrated. The crude was fractionated by FCC (10% of ethyl acetate in toluene) to give the title compound (74 mg, 41%).

$^1$H NMR (600 MHz, $CDCl_3$) δ 7.90 (1H, d, J=16.0 Hz), 7.46-7.55 (2H, m), 7.28-7.33 (3H, m), 6.16 (1H, d, J=16.0 Hz), 5.75 (1H, s), 3.70 (3H, s), 2.56 (1H, d, J=17.0 Hz), 2.45 (1H, d, J=17.0 Hz), 2.22 (3H, s), 2.00 (3H, d, J=1.0 Hz), 1.13 (3H, s), 1.03 (3H, s).

Example 2: (2Z,4E)-5-((S)-1-Hydroxy-2,6,6-trimethyl-4-oxo-3-(phenylethynyl)cyclohex-2-en-1-yl)-3-methylpenta-2,4-dienoic acid (1019)

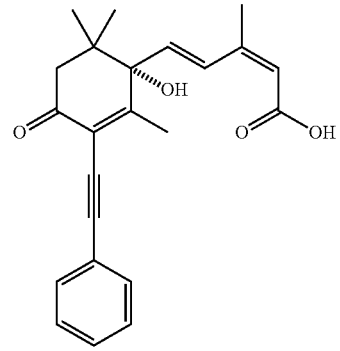 [SMILES: CC1=C(C#Cc2ccccc2)C(=O)CC(C)(C)[C@@]1(O)/C=C/C(C)=C\C(=O)O]

Under argon, 3'-iodo-(S)-ABA (1.00 g, 2.56 mmol), tetrakis(triphenylphosphine)palladium (0) (890 mg, 0.770 mmol) and copper (1) iodide (147 mg, 0.772 mmol) were transferred into a round bottom flask and THF (25 mL), triethylamine (5 mL) and ethynylbenzene (0.42 mL, 3.8 mmol) at room temperature were added sequentially. The flask was lowered into an oil bath set to 95° C. After stirring for 1 hour, the reaction was allowed to come to ambient temperature and diluted with ethyl acetate. The organic phase was washed with 1.2 M HCl twice, brine once, dried over $Na_2SO_4$ and concentrated. The crude was fractionated by FCC (20% to 40% of acetone in hexanes with 0.1% of acetic acid) to give the title compound (720 mg, 77%).

$^1$H NMR (500 MHz, $CDCl_3$) δ 7.88 (1H, d, J=16.0 Hz, HC-4), 7.50-7.54 (2H, m, HC-13' x2), 7.29-7.34 (3H, m, HC-14' x2, HC-15'), 6.18 (1H, d, J=16.0 Hz, HC-5), 5.76 (1H, s, HC-2), 2.58 (1H, d, J=17.0 Hz, HC-5'), 2.46 (1H, d, J=17.0 Hz, HC-5'), 2.21 (3H, s, $H_3$C-7'), 2.04 (3H, d, J=1.0 Hz, $H_3$C-6), 1.14 (3H, s), 1.04 (3H, s).

$^{13}$C NMR (125 MHz, $CDCl_3$) δ 194.0 (s, C-4'), 170.5 (s, C-1), 165.2 (s, C-2'), 151.7 (s, C-3), 136.3 (d, C-5), 132.0 (d, C-13' x2), 128.9 (d, C-4), 128.7 (d, C-15'), 128.4 (d, C-14' x2), 123.2 (s, C-12'), 122.6 (s, C-3'), 118.2 (d, C-2), 97.6 (s, C-11'), 83.0 (s, C-10'), 80.2 (s, C-1'), 49.6 (t, C-5'), 41.1 (s, C-6'), 24.5 (q), 23.3 (q), 21.6 (q, C-6), 18.4 (q, C-7').

HRMS m/z calcd. for $C_{23}H_{24}O_4$+$Na^+$ 387.1567, found 387.1586 (ESI).

Example 3: (2Z,4E)-5-((S)-1-Hydroxy-3-((4-methoxyphenyl)ethynyl)-2,6,6-trimethyl-4-oxocyclohex-2-en-1-yl)-3-methylpenta-2,4-dienoic acid (1021)

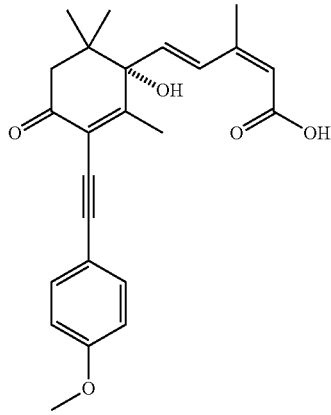 [SMILES: COc1ccc(C#CC2=C(C)[C@](O)(/C=C/C(C)=C\C(=O)O)C(C)(C)CC2=O)cc1]

Under argon, 3'-iodo-(S)-ABA (108 mg, 0.277 mmol), tetrakis(triphenylphosphine)palladium (0) (160 mg, 0.138 mmol) and copper (I) iodide (27 mg, 0.14 mmol) were transferred to a RBF and sequentially was added THF (2.7 mL), triethylamine (2.7 mL) and 1-ethynyl-4-methoxybenzene (54 mg, 0.41 mmol) at room temperature. The suspension was placed in an oil bath at 100° C. After stirring for 2 hours, the reaction was allowed to come to ambient temperature and diluted with ethyl acetate. The organic phase was washed with 1.2 M HCl twice, brine once, dried over $Na_2SO_4$ and concentrated. The crude was fractionated by FCC (20% to 40% of acetone in hexanes with 0.1% of acetic acid) to give the title compound (67 mg, 61%).

$^1$H NMR (500 MHz, $CDCl_3$) δ 7.89 (1H, d, J=16.0 Hz, HC-4), 7.46 (2H, ap d, J=9.0 Hz, HC-13' x2), 6.84 (2H, ap d, J=9.0 Hz, HC-14' x2), 6.18 (1H, d, J=16.0 Hz, HC-5), 5.77 (1H, s, HC-2), 3.81 (3H, s, $H_3CO$), 2.57 (1H, d, J=17.0 Hz, HC-5'), 2.46 (1H, d, J=17.0 Hz, HC-5'), 2.20 (3H, s, $H_3C-7'$), 2.04 (3H, d, J=1.0 Hz, $H_3C-6$), 1.13 (3H, s), 1.04 (3H, s).

$^{13}$C NMR (125 MHz, $CDCl_3$) δ 194.1 (s, C-4'), 170.1 (s, C-1), 164.4 (s, C-2'), 160.0, (s, C-15'), 151.7 (s, C-3), 136.4 (d, C-5), 133.5 (d, C-13' x2), 128.7 (d, C-4), 122.7 (s, C-3'), 118.1 (d, C-2), 115.3 (s, C-12'), 114.1 (d, C-14' x2), 97.7 (s, C-11'), 81.8 (s, C-10'), 80.2 (s, C-1'), 55.5 (q, C-16'), 49.6 (t, C-5'), 41.1 (s, C-6'), 24.5 (q), 23.3 (q), 21.6 (q, C-6), 18.3 (q, C-7').

HRMS m/z calcd. for $C_{24}H_{26}O_5+Na^+$ 417.1672, found 417.1686 (ESI).

Example 4: (2Z,4E)-5-((S)-3-((4-Fluorophenyl)ethynyl)-1-hydroxy-2,6,6-trimethyl-4-oxocyclohex-2-en-1-yl)-3-methylpenta-2,4-dienoic acid (1022)

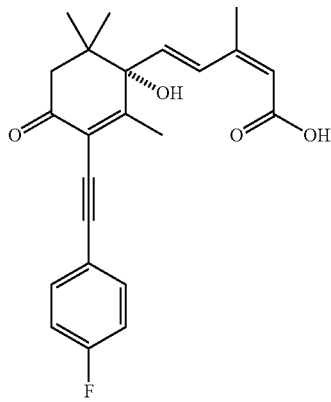 [SMILES: CC1=C(C#Cc2ccc(F)cc2)C(=O)CC(C)(C)[C@@]1(O)/C=C/C(C)=C\C(=O)O]

Under argon, 3'-iodo-(S)-ABA (97 mg, 0.25 mmol), tetrakis(triphenylphosphine)palladium (0) (144 mg, 0.124 mmol) and copper (I) iodide (24 mg, 0.13 mmol) were transferred to a RBF and sequentially were added THF (2.5 mL), triethylamine (2.5 mL) and 1-ethynyl-4-fluorobenzene (44 mg, 0.37 mmol) at rt. The suspension was placed in an oil bath at 95° C. After stirring for 1 hour, the reaction was allowed to come to ambient temperature and diluted with ethyl acetate. The organic phase was washed with 1.2 M HCl twice, brine once, dried over $Na_2SO_4$ and concentrated. The crude was fractionated by FCC (40% of diethyl ether in toluene with 0.1% of acetic acid) to give the title compound (46 mg, 48%).

$^1$H NMR (500 MHz, $CDCl_3$) δ 7.87 (1H, d, J=16.0 Hz, HC-4), 7.47-7.53 (2H, m, HC-13' x2), 6.97-7.05 (2H, m, HC-14' x2), 6.17 (1H, d, J=16.0 Hz, HC-5), 5.76 (1H, s, HC-2), 2.57 (1H, d, J=17.0 Hz, HC-5'), 2.45 (1H, d, J=17.0 Hz, HC-5'), 2.19 (3H, s, $H_3C-7'$), 2.04 (3H, d, J=1.0 Hz, $H_3C-6$), 1.14 (3H, s), 1.04 (3H, s).

$^{13}$C NMR (125 MHz, $CDCl_3$) δ 194.1 (s, C-4'), 170.3 (s, C-1), 165.3 (s, C-2'), 162.9 (s, C-15', $^1J_{CF}$=249.8 Hz), 151.7 (s, C-3), 136.3 (d, C-5), 133.9 (d, C-13' x2, $^3J_{CF}$=8.4 Hz), 128.9 (d, C-4), 122.4 (s, C-3'), 119.3 (s, C-12', $^4J_{CF}$=3.5 Hz), 118.2 (d, C-2), 115.8 (d, C-14' x2, $^2J_{CF}$=22.1 Hz), 97.5 (s, C-11'), 82.7 (s, C-10'), 80.2 (s, C-1'), 49.6 (t, C-5'), 41.2 (s, C-6'), 24.5 (q), 23.3 (q), 21.6 (q, C-6), 18.4 (q, C-7').

HRMS m/z calcd. for $C_{23}H_{23}FO_4+Na^+$405.1473, found 405.1456 (ESI).

Example 5: (2Z,4E)-5-((S)-1-Hydroxy-2,6,6-trimethyl-4-oxo-3-((4-(trifluoromethoxy)phenyl)ethynyl)cyclohex-2-en-1-yl)-3-methylpenta-2,4-dienoic acid (1023)

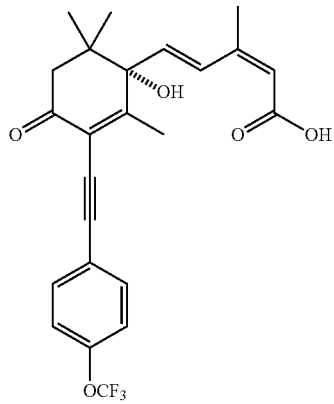 [SMILES: CC1=C(C#Cc2ccc(OC(F)(F)F)cc2)C(=O)CC(C)(C)[C@@]1(O)/C=C/C(C)=C\C(=O)O]

Under argon, 3'-iodo-(S)-ABA (100 mg, 0.256 mmol), tetrakis(triphenylphosphine)palladium (0) (149 mg, 0.129 mmol) and copper (I) iodide (25 mg, 0.13 mmol) were transferred to a RBF and sequentially was added THF (2.6 mL), triethylamine (2.6 mL) and 1-ethynyl-4-(trifluoromethoxy)benzene (0.07 mL, 0.5 mmol) at room temperature. The suspension was placed in an oil bath at 95° C. After stirring for 1 hour, the reaction was allowed to come to ambient temperature and diluted with ethyl acetate. The organic phase was washed with 1.2 M HCl twice, brine once, dried over $Na_2SO_4$ and concentrated. The crude was fractionated by FCC (40% of diethyl ether in toluene with 0.1% of acetic acid) to give the title compound (71 mg, 61%).

¹H NMR (500 MHz, CDCl₃) δ 7.87 (1H, d, J=16.0 Hz, HC-4), 7.54 (2H, ap d, J=8.5 Hz, HC-13' x2), 7.16 (2H, ap d, J=8.5 Hz, HC-14' x2), 6.17 (1H, d, J=16.0 Hz, HC-5), 5.76 (1H, s, HC-2), 2.57 (1H, d, J=17.0 Hz, HC-5'), 2.46 (1H, d, J=17.0 Hz, HC-5'), 2.19 (3H, s, H₃C-7'), 2.04 (3H, d, J=1.0 Hz, H₃C-6), 1.14 (3H, s), 1.04 (3H, s).

¹³C NMR (125 MHz, CDCl₃) δ 194.0 (s, C-4'), 170.3 (s, C-1), 165.9 (s, C-2'), 151.7 (s, C-3), 149.3 (s, C-15', ³$J_{CF}$=1.9 Hz), 136.3 (d, C-5), 133.5 (d, C-13' x2), 129.0 (d, C-4), 122.3 (s, C-3'), 121.9 (s, C-12'), 120.9 (d, C-14' x2, ⁴$J_{CF}$=1.1 Hz), 120.6 (s, C-16', ¹$J_{CF}$=257.9 Hz), 118.2 (d, C-2), 96.0 (s, C-11'), 83.8 (s, C-10'), 80.2 (s, C-1'), 49.5 (t, C-5'), 41.2 (s, C-6'), 24.5 (q), 23.3 (q), 21.6 (q, C-6), 18.5 (q, C-7').

HRMS m/z calcd. for $C_{24}H_{23}F_3O_4$+Na⁺ 471.1395, found 471.1409 (ESI).

Example 6: (2Z,4E)-5-((S)-1-Hydroxy-2,6,6-trimethyl-4-oxo-3-((4-phenoxyphenyl)ethynyl)cyclohex-2-en-1-yl)-3-methylpenta-2,4-dienoic acid (1024)

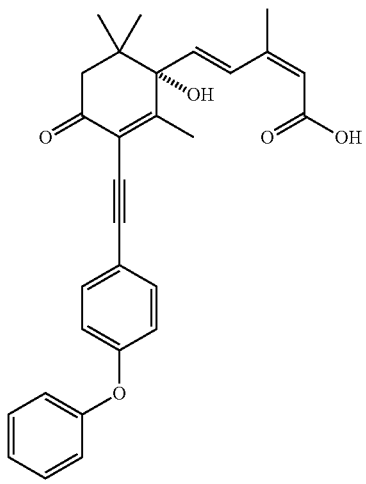 [SMILES: CC1=C(C#Cc2ccc(Oc3ccccc3)cc2)C(=O)CC(C)(C)[C@@]1(O)/C=C/C(C)=C\C(=O)O]

Under argon, 3'-iodo-(S)-ABA (100 mg, 0.256 mmol), tetrakis(triphenylphosphine)palladium (0) (148 mg, 0.128 mmol) and copper (1) iodide (26 mg, 0.14 mmol) were transferred to a RBF and sequentially were added THF (2.6 mL), triethylamine (2.6 mL) and 1-ethynyl-4-phenoxybenzene (0.07 mL, 0.4 mmol) at rt. The suspension was placed in an oil bath at 95° C. After stirring for 1 hour, the reaction was allowed to come to ambient temperature and diluted with ethyl acetate. The organic phase was washed with 1.2 M HCl twice, brine once, dried over Na₂SO₄ and concentrated. The crude was fractionated by FCC (30% of acetone in hexanes with 0.1% of acetic acid) to give the title compound (77 mg, 65%).

¹H NMR (500 MHz, CDCl₃) δ 7.88 (1H, bd, J=16.0 Hz, HC-4), 7.48 (2H, d, J=8.5 Hz, HC-13' x2), 7.35 (2H, dd, J=7.5, 8.5 Hz, HC-18' x2), 7.14 (1H, t, J=7.5 Hz, HC-19'), 7.02 (2H, d, J=8.5 Hz, HC-17' x2), 6.92 (2H, d, J=8.5 Hz, HC-14' x2), 6.17 (1H, d, J=16.0 Hz, HC-5), 5.78 (1H, bs, HC-2), 2.57 (1H, d, J=17.0 Hz, HC-5'), 2.46 (1H, d, J=17.0 Hz, HC-5'), 2.20 (3H, s, H₃C-7'), 2.04 (3H, s, H₃C-6), 1.14 (3H, s), 1.04 (3H, s).

¹³C NMR (125 MHz, CDCl₃) δ 194.2 (s, C-4'), 170.1 (s, C-1), 165.0 (s, C-2'), 158.0 (s, C-15'), 156.5 (s, C-16'), 151.7 (s, C-3), 136.4 (d, C-5), 133.6 (d, C-13' x2), 130.1 (d, C-18' x2), 128.8 (d, C-4), 124.1, (d, C-19'), 122.6 (s, C-3'), 119.7 (d, C-17' x2), 118.4 (d, C-14' x2), 118.2 (d, C-2), 117.6 (s, C-12'), 97.2 (s, C-11'), 82.4 (s, C-10'), 80.2 (s, C-1'), 49.6 (t, C-5'), 41.1 (s, C-6'), 24.5 (q), 23.3 (q), 21.6 (q, C-6), 18.4 (q, C-7').

HRMS m/z calcd. for $C_{29}H_{28}O_5$+Na⁺ 479.1829, found 479.1849 (ESI).

Example 7: (2Z,4E)-5-((S)-3-((4-Ethylphenyl)ethynyl)-1-hydroxy-2,6,6-trimethyl-4-oxocyclohex-2-en-1-yl)-3-methylpenta-2,4-dienoic acid (1025)

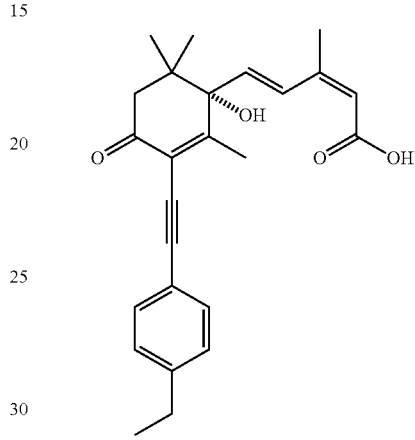

Under argon, 3'-iodo-(S)-ABA (101 mg, 0.259 mmol), tetrakis(triphenylphosphine)palladium (0) (149 mg, 0.129 mmol) and copper (1) iodide (25 mg, 0.13 mmol) were transferred to a RBF and sequentially were added THF (2.6 mL), triethylamine (2.6 mL) and 1-ethyl-4-ethynylbenzene (0.06 mL, 0.4 mmol) at rt. The flask was placed in an oil bath at 95° C. After stirring for 1 hour, the reaction was allowed to come to ambient temperature and diluted with ethyl acetate. The organic phase was washed with 1.2 M HCl twice, brine once, dried over Na₂SO₄ and concentrated. The crude was fractionated by FCC (30% of diethyl ether in toluene with 0.1% of acetic acid) to give the title compound (61 mg, 59%).

¹H NMR (500 MHz, CDCl₃) δ 7.87 (1H, d, J=16.0 Hz, HC-4), 7.43 (2H, d, J=8.0 Hz, HC-13' x2), 7.14 (2H, d, J=8.0 Hz, HC-14' x2), 6.17 (1H, d, J=16.0 Hz, HC-5), 5.77 (1H, s, HC-2), 2.64 (2H, q, J=7.5 Hz, H₂C-16'), 2.57 (1H, d, J=17.0 Hz, HC-5'), 2.46 (1H, d, J=17.0 Hz, HC-5'), 2.19 (3H, s, H₃C-7'), 2.04 (3H, d, J=1.0 Hz, H₃C-6), 1.22 (3H, t, J=7.5 Hz, H₃C-17'), 1.13 (3H, s), 1.03 (3H, s).

¹³C NMR (125 MHz, CDCl₃) δ 194.2 (s, C-4'), 170.3 (s, C-1), 165.0 (s, C-2'), 151.7 (s, C-3), 145.2 (s, C-15'), 136.4 (d, C-5), 132.0 (d, C-13' x2), 128.8 (d, C-4), 128.0 (d, C-14' x2), 122.6 (s, C-3'), 120.3 (s, C-12'), 118.2 (d, C-2), 97.8 (s, C-11'), 82.3 (s, C-10'), 80.2 (s, C-1'), 49.6 (t, C-5'), 41.1 (s, C-6'), 29.0 (t, C-16'), 24.5 (q), 23.3 (q), 21.6 (q, C-6), 18.3 (q, C-7'), 15.5 (q, C-17').

HRMS m/z calcd. for $C_{25}H_{28}O_4$+Na⁺415.1885, found 415.1881 (ESI).

Example 8: (2Z,4E)-5-((S)-3-(3-ethyl-3-hydroxy-pent-1-yn-1-yl)-1-hydroxy-2,6,6-trimethyl-4-oxocyclohex-2-en-1-yl)-3-methylpenta-2,4-dienoic acid (1059)

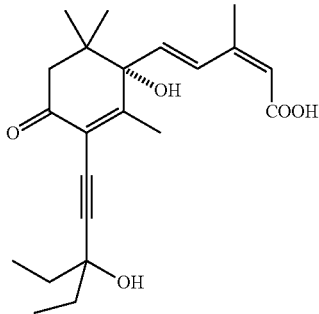 [SMILES: CCC(O)(C#CC1=C(C)[C@](O)(/C=C/C(C)=C\C(=O)O)C(C)(C)CC1=O)CC]

Under argon, 3'-iodo-(S)-ABA (105 mg, 0.27 mmol), tetrakis(triphenylphosphine)palladium (0) (94 mg, 0.081 mmol) and copper (1) iodide (16 mg, 0.084 mmol) were transferred to a RBF and sequentially were added THF (2.7 mL), triethylamine (0.54 mL) and 3-ethyl-1-pentyn-3-ol (0.05 mL, 0.4 mmol) at rt. The flask was placed in an oil bath at 95° C. After stirring for 1 hour, the reaction was allowed to come to ambient temperature and diluted with ethyl acetate. The organic phase was washed with 1.2 M HCl twice, brine once, dried over $Na_2SO_4$ and concentrated. The crude was fractionated by FCC (30% of acetone in hexanes with 0.1% of acetic acid) to give the title compound (56 mg, 55%).

$^1$H NMR (500 MHz, $CDCl_3$) δ 7.77 (1H, d, J=16.0 Hz, HC-4), 6.13 (1H, d, J=16.0 Hz, HC-5), 5.77 (1H, bs, HC-2), 2.50 (1H, d, J=17.0 Hz, HC-5'), 2.37 (1H, d, J=17.0 Hz, HC-5'), 2.13 (3H, s, $H_3$C-7'), 2.04 (3H, s, $H_3$C-6), 1.67-1.81 (4H, m, $H_2$C-13' x2), 1.10 (3H, s), 1.08 (6H, dt, J=1.5, 7.5 Hz, $H_3$C-14' x2), 1.03 (3H, s).

$^{13}$C NMR (125 MHz, $CDCl_3$) δ 194.5 (s, C-4'), 170.5 (s, C-1), 165.3 (s, C-2'), 151.5 (s, C-3), 136.3 (d, C-5), 129.1 (d, C-4), 122.3 (s, C-3'), 118.6 (d, C-2), 100.5 (s, C-11'), 80.4 (s, C-10'), 77.8 (s, C-1'), 72.8 (s, C-12'), 49.5 (t, C-5'), 41.2 (s, C-6'), 34.50 (t, C-13'), 34.45 (t, C-13'), 24.4 (q), 23.3 (q), 21.6 (q, C-6), 18.6 (q, C-7'), 8.93 (q, C-14'), 8.91 (q, C-14').

HRMS m/z calcd. for $C_{22}H_{30}O_5$+$Na^+$ 397.1985, found 397.1973 (ESI).

Example 9: (2Z,4E)-5-((S)-1-hydroxy-3-((Z)-5-hydroxy-3-methylpent-3-en-1-yn-1-yl)-2,6,6-trimethyl-4-oxocyclohex-2-en-1-yl)-3-methylpenta-2,4-dienoic acid (1063)

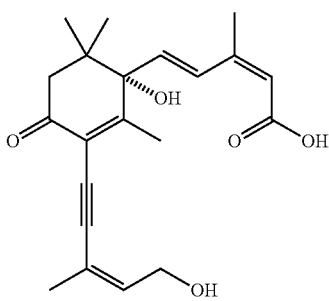 [SMILES: CC1=C(C#C/C(C)=C\CO)C(=O)CC(C)(C)[C@@]1(O)/C=C/C(C)=C\C(=O)O]

Under argon, 3'-iodo-(S)-ABA (205 mg, 0.526 mmol), tetrakis(triphenylphosphine)palladium (0) (184 mg, 0.16 mmol) and copper (1) iodide 29.5 mg, 0.15 mmol) were weighted into a RBF and sequentially added THF (5.4 mL), triethylamine (1.1 mL) and (Z)-3-methylpent-2-en-4-yn-1-ol (81.5 mg, 0.85 mmol) at rt. The flask was placed in an oil bath at 95° C. After stirring for 1 hour, the reaction was allowed to come to ambient temperature and diluted with ethyl acetate. The organic phase was washed with 1.2 M HCl twice, brine once, dried over $Na_2SO_4$ and concentrated. The crude was fractionated by FCC (40% of acetone in hexanes with 0.1% of acetic acid) to give the title compound (95.5 mg, 51%).

$^1$H NMR (500 MHz, $CDCl_3$) δ 7.76 (1H, d, J=16.0 Hz, HC-4), 6.13 (1H, d, J=16.0 Hz, HC-5), 5.99 (1H, dt, J=1.0, 6.5 Hz, HC-13'), 5.76 (1H, s, HC-2), 4.35 (2H, dd, J=6.5, 6.5 Hz, $H_2$C-14'), 2.52 (1H, d, J=17.0 Hz, HC-5'), 2.40 (1H, d, J=17.0 Hz, HC-5'), 2.15 (3H, s, $H_3$C-7'), 2.03 (3H, d, J=1.0 Hz, $H_3$C-6), 1.94 (3H, d, J=1.0 Hz, $H_3$C-15'), 1.10 (3H, s), 1.04 (3H, s).

$^{13}$C NMR (125 MHz, $CDCl_3$) δ 194.7 (s, C-4'), 169.7 (s, C-1), 165.3 (s, C-2'), 151.0 (s, C-3), 136.8 (d, C-13'), 136.1 (d, C-5), 129.1 (d, C-4), 122.5 (s, C-3'), 121.7 (s, C-12'), 118.2 (d, C-2), 96.1 (s, C-11'), 87.8 (s, C-10'), 80.3 (s, C-1'), 60.9 (t, C-14'), 49.5 (t, C-5'), 41.2 (s, C-6'), 24.4 (q), 23.3 (q), 23.0 (q, C-15'), 21.5 (q, C-6), 18.7 (q, C-7').

HRMS m/z calcd. for $C_{21}H_{26}O_5$+$Na^+$381.1672, found 381.1681 (ESI).

Example 10: (2Z,4E)-5-((S)-1-hydroxy-2,6,6-trimethyl-4-oxo-3-((E)-styryl)cyclohex-2-en-1-yl)-3-methylpenta-2,4-dienoic acid (1090)

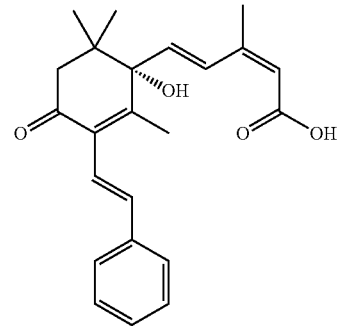 [SMILES: CC1=C(/C=C/c2ccccc2)C(=O)CC(C)(C)[C@@]1(O)/C=C/C(C)=C\C(=O)O]

Under argon, 3'-iodo-(S)-ABA (140 mg, 0.36 mmol), tetrakis(triphenylphosphine)palladium (0) (21 mg, 0.018 mmol), trans-2-phenylvinylboronic acid (108 mg, 0.72 mmol) and potassium carbonate (201 mg, 1.44 mmol) were transferred to a RBF and were added a 9:1 mixture of THF, $H_2O$ (7.2 mL). The flask was placed in an oil bath at 90° C. After stirring for 24 hours, the reaction was allowed to come to ambient temperature, cooled to 0° C. and quenched with 1N HCl. The mixture was diluted with ethyl acetate, separated the layers and the organic phase was washed with brine once, dried over $Na_2SO_4$ and concentrated. The crude was fractionated by FCC (40% of ethyl acetate in hexanes with 0.1% of acetic acid) to give the title compound (30 mg, 23%).

$^1$H NMR (500 MHz, $CDCl_3$) δ 7.86 (1H, d, J=16.0 Hz, HC-4), 7.46 (2H, d, J=7.4 Hz, HC-13'), 7.32 (2H, t, J=7.4 Hz, HC-14'), 7.25 (1H, t, J=7.4 Hz, HC-15'), 7.0 (1H, d, J=16.5 Hz, HC-11'), 6.84 (1H, d, J=16.5 Hz, HC-10'), 6.21

(1H, d, J=16.1 Hz, HC-5) 5.75 (1H, s, HC-2), 2.58 (1H, d, J=16.9 Hz, HC-5'), 2.42 (1H, d, J=16.9 Hz, HC-5'), 2.09 (1H, s, OH), 2.05 (6H, s, $H_3$C-6, $H_3$C-7'), 1.14 (3H, s, $H_3$C-8' or $H_3$C-9'), 1.04 (3H, s, $H_3$C-8' or $H_3$C-9').

$^{13}$C NMR (125 MHz, CDCl$_3$) δ 197.1 (s, C-4'), 171.1 (s, C-1), 156.3 (s, C-2'), 152.0 (s, C-3), 137.7 (s, C-12'), 137.3 (d, C-5), 135.9 (d, C-11'), 133.4 (s, C-3'), 128.7 (d, C-14'), 128.6 (d, C-4), 128.0 (d, C-15'), 126.8 (d, C-13'), 121.6 (d, C-10'), 118.0 (d, C-2), 80.7 (s, C-1'), 50.2 (t, C-5'), 40.8 (s, C-6'), 24.7 (q, C-8' or C-9'), 23.4 (q, C-8' or C-9'), 21.7 (q, C-6), 16.7 (q, C-7').

HRMS m/z calcd for $C_{23}H_{25}O_4$ (M-1) 365.1758, found 365.1744 (ESI).

Example 11: (2Z,4E)-5-((S)-1-hydroxy-3-((4-hydroxyphenyl)ethynyl)-2,6,6-trimethyl-4-oxocyclohex-2-en-1-yl)-3-methylpenta-2,4-dienoic acid (1091)

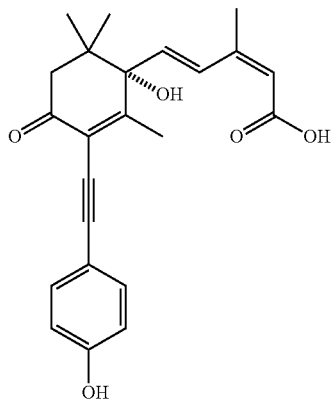 [SMILES: CC1=C(C#Cc2ccc(O)cc2)C(=O)CC(C)(C)[C@@]1(O)/C=C/C(C)=C\C(=O)O]

Under argon, 3'-iodo-(S)-ABA (157 mg, 0.40 mmol), 4-ethynylphenol[20] (94 mg, 0.80 mmol), copper (1) iodide (39 mg, 0.20 mmol), triethylamine (0.8 mL) and THF (4.0 mL) were transferred to a RBF and the mixture was degassed with argon for 10 minutes. Tetrakis(triphenylphosphine)palladium (0) (233 mg, 0.20 mmol) was added to the reaction mixture and the flask was placed in an oil bath at 90° C. After stirring for 1.5 hours, the reaction was allowed to come to ambient temperature, cooled to 0° C. and quenched with 1N HCl. The mixture was diluted with ethyl acetate, separated the layers and the organic phase was washed with brine once, dried over $Na_2SO_4$ and concentrated. The crude was fractionated by FCC (30% to 100% of ethyl acetate in hexanes with 0.2% of acetic acid) to give a semi pure compound that was further purified through PTLC (15% of isopropanol in hexanes with 0.2% of acetic acid) to give the title compound (21 mg, 14%).

$^1$H NMR (500 MHz, CD$_3$OD) δ 7.81 (1H, d, J=16.1 Hz, HC-4), 7.35 (2H, d, J=8.7 Hz, HC-13'), 6.76 (2H, d, J=8.7 Hz, HC-14'), 6.27 (1H, d, J=16.1 Hz, HC-5) 5.75 (1H, s, HC-2), 2.64 (1H, d, J=16.9 Hz, HC-5'), 2.34 (1H, d, J=16.9 Hz, HC-5'), 2.20 (3H, s, $H_3$C-7'), 2.05 (3H, d, J=1.0 Hz, $H_3$C-6), 1.07 (3H, s, $H_3$C-8' or $H_3$C-9'), 1.04 (3H, s, $H_3$C-8' or $H_3$C-9').

$^{13}$C NMR (125 MHz, CD$_3$OD) δ 197.2 (s, C-4'), 169.5 (s, C-1), 167.3 (s, C-2'), 159.3 (s, C-15'), 151.0 (s, C-3), 137.5 (s, C-5), 134.2 (d, C-13'), 129.8 (d, C-4), 123.4 (s, C-3'), 119.7 (d, C-2), 116.4 (d, C-14'), 115.1 (s, C-12'), 98.7 (s, C-11'), 81.8 (s, C-10'), 80.7 (s, C-1'), 50.4 (t, C-5'), 42.2 (s, C-6'), 24.7 (q, C-8' or C-9'), 23.6 (q, C-8' or C-9'), 21.3 (q, C-6), 18.8 (q, C-7').

HRMS m/z calcd for $C_{23}H_{25}O_5Na^+$ 403.1515, found 403.1530 (ESI).

Example 12: (2Z,4E)-5-((S)-3-(cyclohexylethynyl)-1-hydroxy-2,6,6-trimethyl-4-oxocyclohex-2-en-1-yl)-3-methylpenta-2,4-dienoic acid (1100)

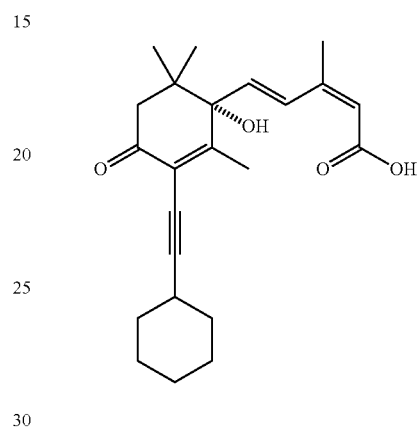

Under argon, 3'-iodo-(S)-ABA (157 mg, 0.40 mmol), ethynylcyclohexane (87 mg, 105 μL, 0.80 mmol), copper (1) iodide (39 mg, 0.20 mmol), triethylamine (0.8 mL) and THF (4.0 mL) were transferred to a RBF and the mixture was degassed with argon for 10 minutes. Tetrakis(triphenylphosphine)palladium (0) (137 mg, 0.12 mmol) was added to the reaction mixture and the flask was placed in an oil bath at 90° C. After stirring for 1.5 hours, the reaction was allowed to come to ambient temperature, cooled to 0° C. and quenched with 1N HCl. The mixture was diluted with ethyl acetate, separated the layers and the organic phase was washed with brine once, dried over $Na_2SO_4$ and concentrated. The crude was fractionated by FCC (20% to 40% of ethyl acetate in hexanes with 0.2% of acetic acid) to give the title compound (71 mg, 47%).

$^1$H NMR (500 MHz, CDCl$_3$) δ 7.86 (1H, d, J=15.9 Hz, HC-4), 6.16 (1H, d, J=16.0 Hz, HC-5) 5.77 (1H, s, HC-2), 2.66-2.61 (1H, m, HC-12'), 2.51 (1H, d, J=17.2 Hz, HC-5'), 2.41 (1H, d, J=17.2 Hz, HC-5'), 2.11 (3H, s, $H_3$C-7'), 2.04 (3H, d, J=1.1 Hz, $H_3$C-6), 1.89-1.83 (2H, m, HC-13'), 1.76-1.69 (2H, m, HC-14'), 1.56-1.49 (3H, m, HC-13', HC-15'), 1.36-1.31 (3H, m, HC-14', HC-15'), 1.1 (3H, s, $H_3$C-8' or $H_3$C-9'), 1.0 (3H, s, $H_3$C-8' or $H_3$C-9').

$^{13}$C NMR (125 MHz, CDCl$_3$) δ 194.7 (s, C-4'), 170.9 (s, C-1), 164.1 (s, C-2'), 151.8 (s, C-3), 136.6 (s, C-5), 128.5 (d, C-4), 122.7 (s, C-3'), 118.1 (d, C-2), 103.2 (s, C-11'), 80.0 (s, C-1'), 74.0 (s, C-10'), 49.5 (t, C-5'), 41.0 (s, C-6'), 32.7 (t, C-13'), 30.0 (d, C-12'), 26.1 (t, C-15'), 25.0 (d, C-14'), 24.5 (q, C-8' or C-9'), 23.3 (q, C-8' or C-9'), 21.6 (q, C-6), 18.1 (q, C-7').

HRMS m/z calcd for $C_{23}H_{30}O_4Na^+$ 393.2036, found 393.2055 (ESI).

Example 13: (2Z,4E)-5-((S)-3-hydroxy-2,4,4-trimethyl-6-oxo-3,4,5,6-tetrahydro-'[1,1'-biphenyl]-3-yl)-3-methylpenta-2,4-dienoic acid (1080).[17]

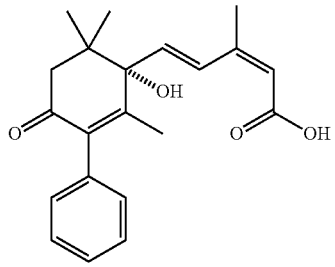 [SMILES: CC1=C(c2ccccc2)C(=O)CC(C)(C)[C@@]1(O)/C=C/C(C)=C\C(=O)O]

Under argon, 3'-iodo-(S)-ABA (45 mg, 0.11 mmol), tetrakis(triphenylphosphine)palladium (0) (13 mg, 0.011 mmol), phenylboronic acid (17 mg, 0.14 mmol) and potassium carbonate (77 mg, 0.55 mmol) were transferred to a RBF and were added a 9:1 mixture of THF, $H_2O$ (2.0 mL). The flask was placed in an oil bath at 90° C. After stirring for 21 hours, the reaction was allowed to come to ambient temperature, cooled to 0° C. and quenched with 1N HCl. The mixture was diluted with ethyl acetate, separated the layers and the organic phase was washed with brine once, dried over $Na_2SO_4$ and concentrated. The crude was fractionated by PTLC (10% of methanol in dichloromethane) to give the title compound (16 mg, 41%).

$^1$H NMR (500 MHz, $CDCl_3$) δ 7.86 (1H, d, J=16.2 Hz, HC-4), 7.36 (2H, t, J=7.2 Hz, HC-12'), 7.29 (1H, t, J=7.4 Hz, HC-13'), 7.07 (2H, d, J=7.0 Hz, HC-11'), 6.26 (1H, d, J=16.2 Hz, HC-5) 5.79 (1H, s, HC-2), 2.60 (1H, d, J=17.0 Hz, HC-5'), 2.43 (1H, d, J=17.0 Hz, HC-5'), 2.08 (3H, s, $H_3C$-6), 1.70 (3H, s, $H_3C$-7'), 1.21 (3H, s, $H_3C$-8' or $H_3C$-9'), 1.08 (3H, s, $H_3C$-8' or $H_3C$-9').

$^{13}$C NMR (125 MHz, $CDCl_3$) δ 196.7 (s, C-4'), 171.1 (s, C-1), 157.2 (s, C-2'), 151.5 (s, C-3), 138.8 (s, C-3'), 137.5 (d, C-5), 135.8 (s, C-10'), 129.9 (d, C-11'), 128.6 (d, C-4), 128.4 (d, C-12'), 127.6 (d, C-13'), 118.5 (d, C-2), 80.4 (s, C-1'), 49.8 (t, C-5'), 41.3 (s, C-6'), 24.6 (q, C-8' or C-9'), 23.3 (q, C-8' or C-9'), 21.6 (q, C-6), 17.4 (q, C-7').

HRMS m/z calcd for $C_{21}H_{23}O_4$ (M-1) 339.1601, found 339.1591 (ESI).

Example 14: Studying the Effect of Exemplary Compounds of the Application and Exemplary Compounds of Formula (II) on Lentil (CDC Maxim) Germination Methodology 40 seeds were counted for each 100×15 mm petri dishes. Each petri dish contained two filter papers and 10 mL of test solutions. Then, they were wrapped with aluminium foil to cut off light. Wrapped plates were kept on lab bench at room temperature. Germinated seeds were counted everyday until one treatment reaches 100% germination (two days). Only light exposure was during plate counting.

The following dosages were used when studying the effect of different exemplary compounds on lentil:
1 μM Compound
10 μM Compound
1 μM Compound+10 μM ABA
10 μM Compound+10 μM ABA All seeds from this experiment have been rinsed first with tap water and then with $dH_2O$, frozen in liquid nitrogen and stored at −80° C. freezer.

Results

Figure 2:
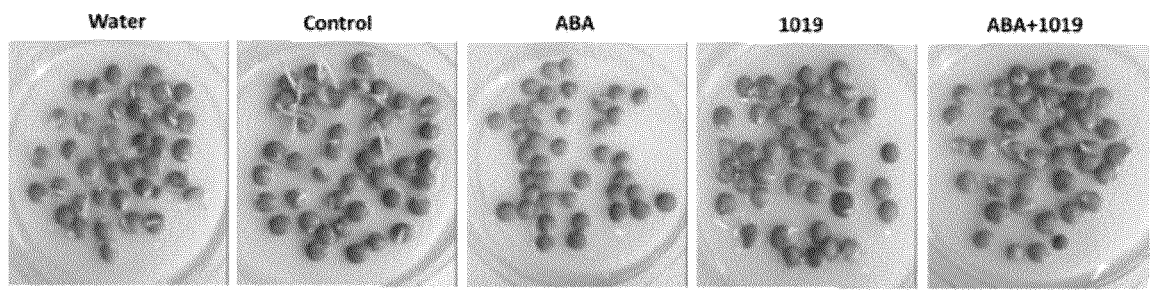
FIG. 2 shows lentil seeds on day two when treated with exemplary compound 1019 used alone or in combination with ABA at a dosage of 10 µM ABA and 100 µM compound 1019 on day 2 compared to ABA alone.
Figure 3A:
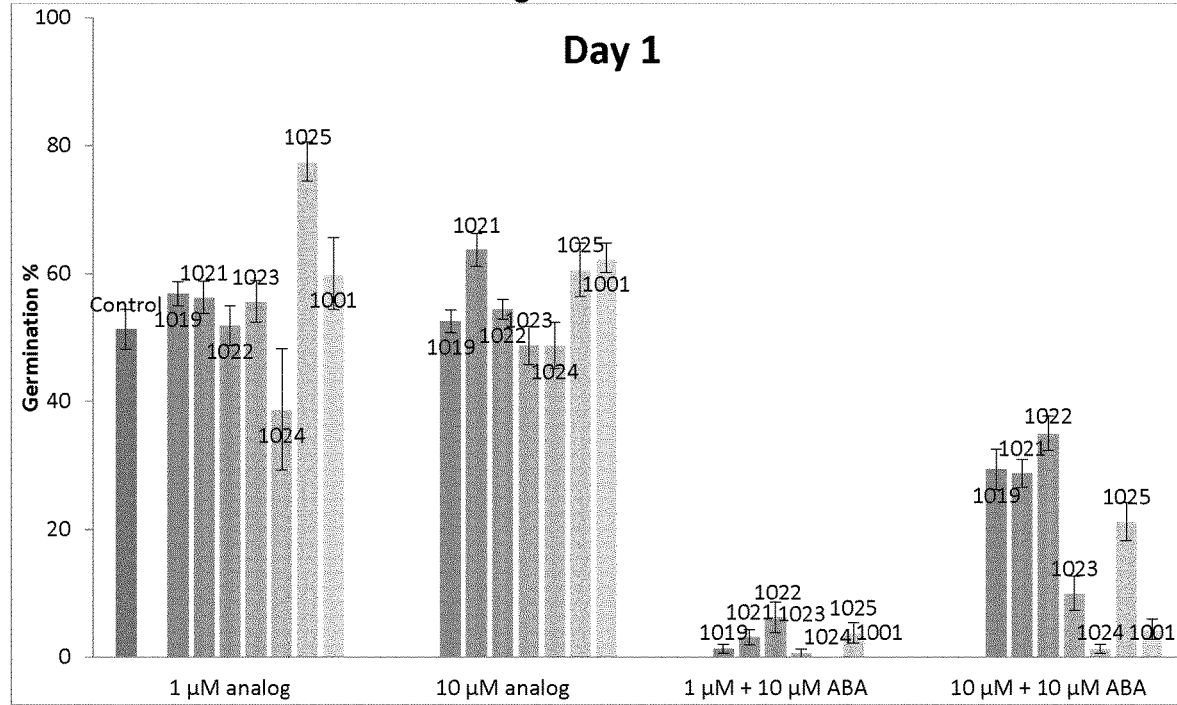
FIG. 3A shows the effect of exemplary compounds of the application and comparative compounds on percent germination of lentil seed on day one. Exemplary compounds of the application at 10 uM promoted germination in the presence of 10 uM ABA.
Figure 3B:
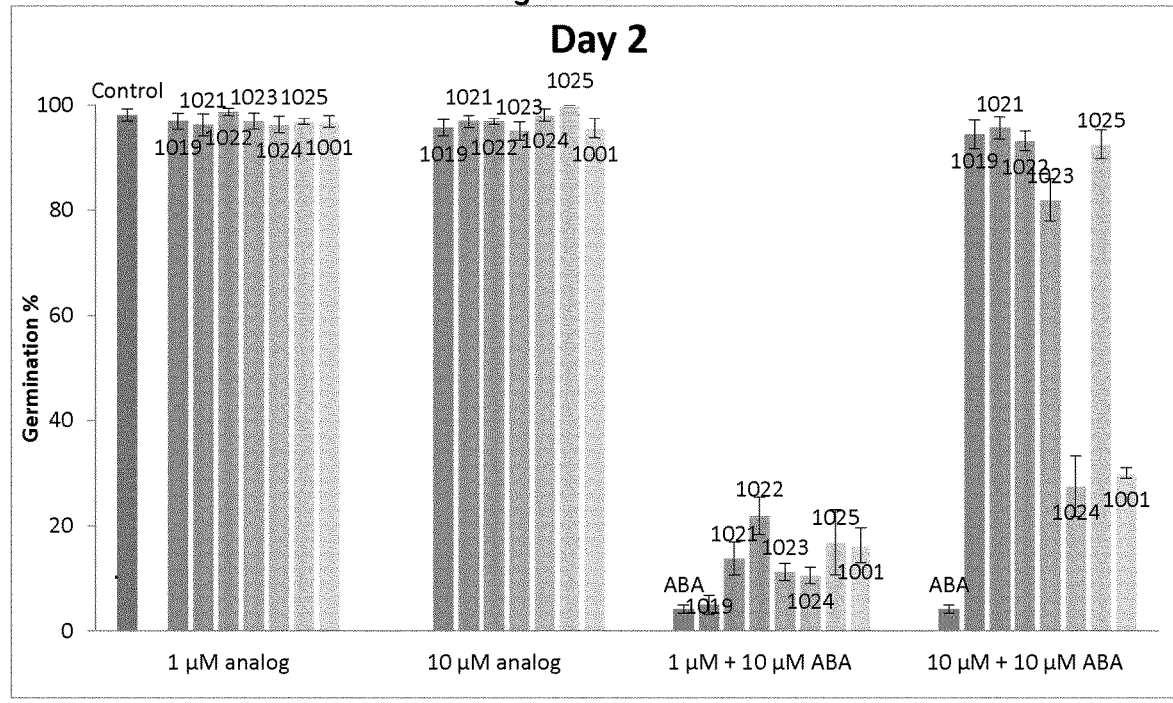
FIG. 3B shows the effect of exemplary compounds of the application and comparative compounds on percent germination of lentil seed on day two. Exemplary compounds of the application overcame ABA-inhibition at 1:1 ratio of compound to ABA.
Figure 4D:
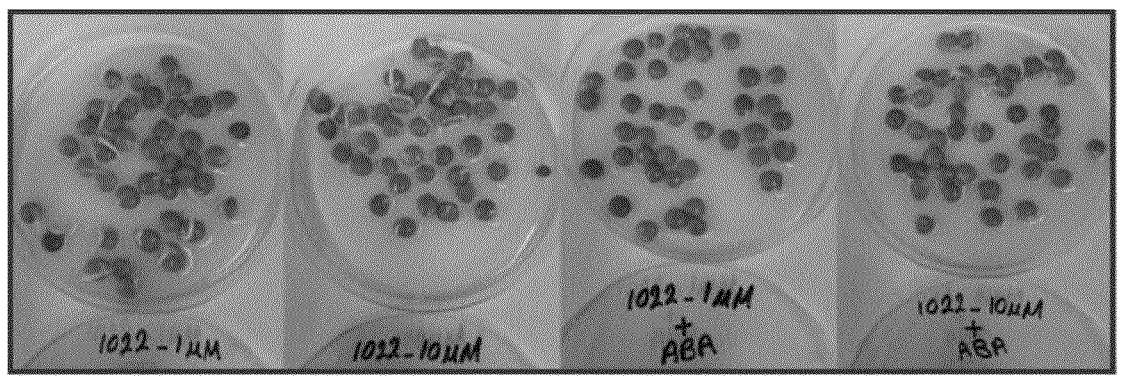
FIG. 4 A to H show lentil seeds treated with exemplary compounds of the application and comparative compounds. (A) Control and 10 µM ABA; and (B-H) Lentils have been treated with from left: 1 µM Exemplary Compound, 10 µM Exemplary Compound, 1 µM Exemplary Compound+10 µM ABA and 10 μM Exemplary Compound+10 μM ABA. Exemplary compounds used were as follows: 1019 (B), 1021 (C), 1022 (D), 1023 (E), 1024 (F), 1025 (G) and comparative compound 1001 (H).
Figure 4E:
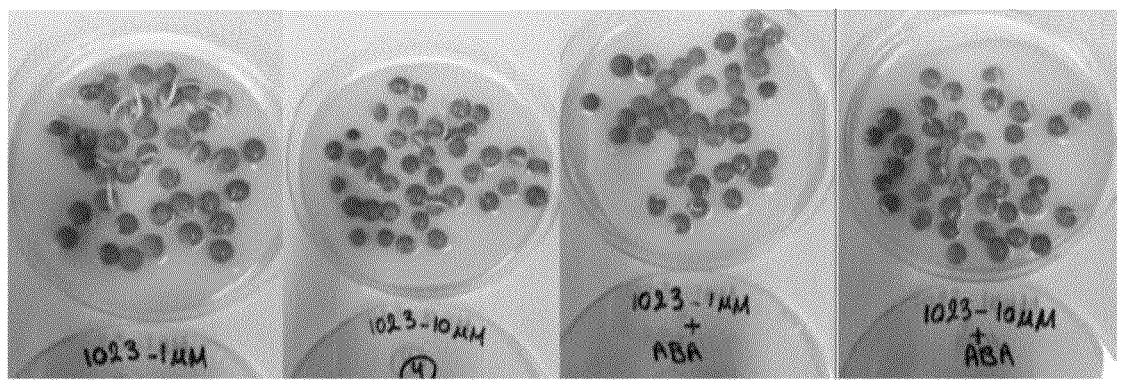
Figure 4F:
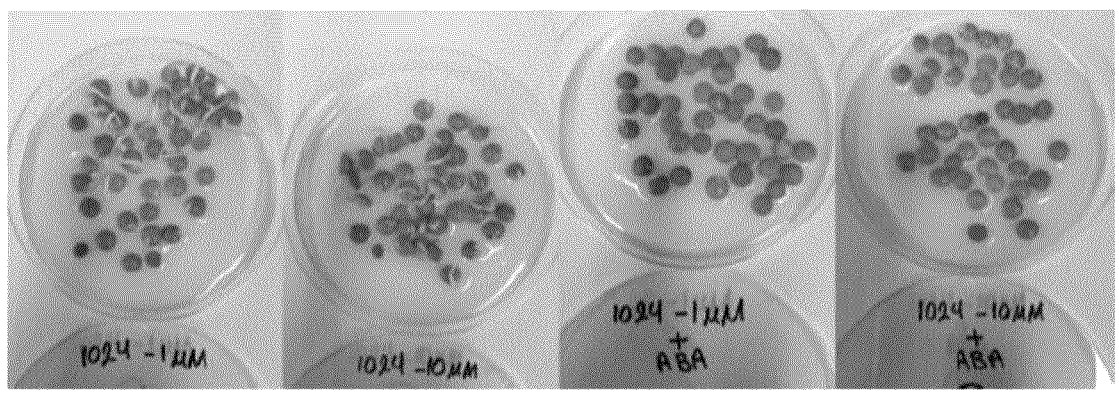
Figure 4G:
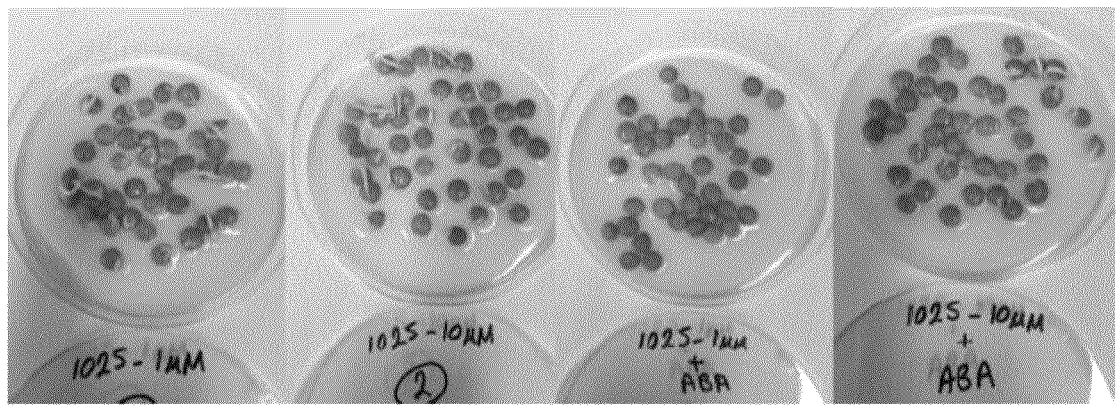
Figure 4H:
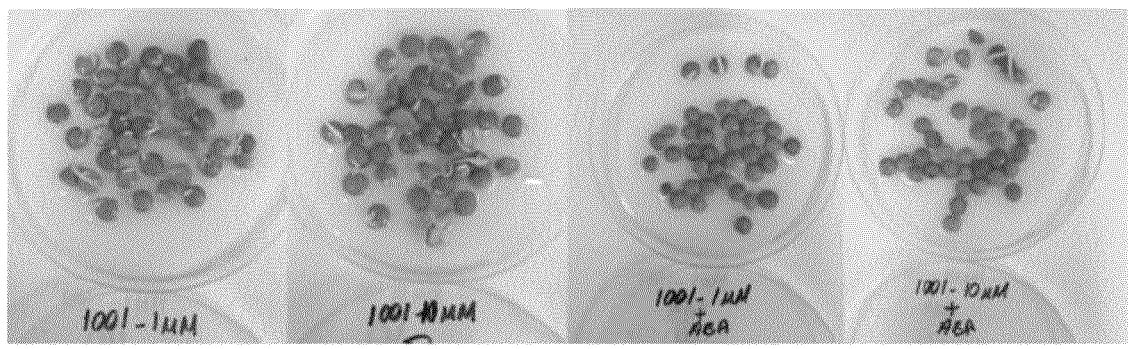

The effect of exemplary compound 1019 used alone or in combination with ABA on percent lentil seed germination at dosage of 10:100 μM on day 1 and 2 compared to ABA alone is shown in FIG. 1A/B and FIG. 2. The effect of exemplary compounds of the application (1019, 1021-1025) and comparative compounds (ABA, 1001) on percent lentil seed germination on day 1 and day 2 after having been treated with 1 μM Compound alone, 10 μM Compound alone, 1 μM Compound+10 μM ABA or 10 μM Compound+10 μM ABA is shown in FIG. 3A and FIG. 3B, respectively. Seed germination was most highly promoted by exemplary compound 1025 at 1 uM. 10 uM ABA alone completely inhibited seed germination (FIG. 3A). Exemplary compounds of the application at 10 uM promoted germination in the presence of 10 uM ABA (FIG. 3A). Seed germination was not affected by exemplary compounds of the application alone at 1 or 10 uM (FIG. 3B). Exemplary compound of the application overcame ABA-inhibition at 1:1 ratio of exemplary compound to ABA (FIG. 3B). FIG. 4 shows images of the lentil seeds after similar treatment.

Figure 5A:
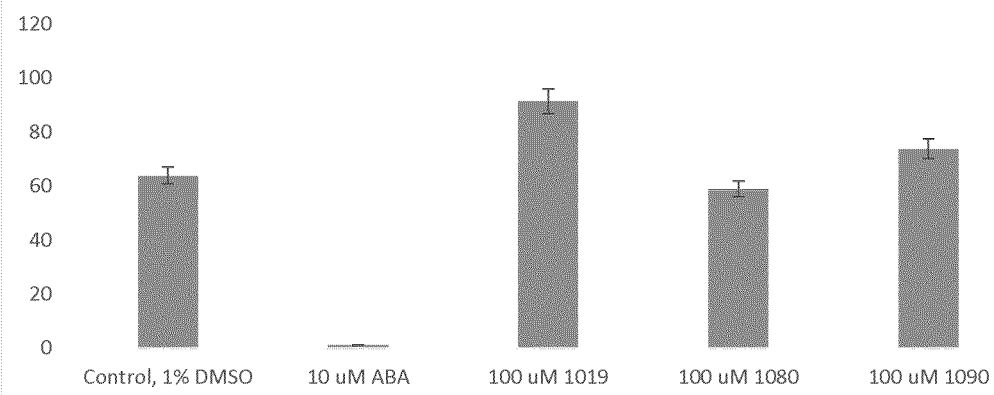
FIG. 5A and FIG. 5B are bar graphs showing lentil seed germination assays with exemplary compound 1080 and exemplary compound 1090.
Figure 5B:
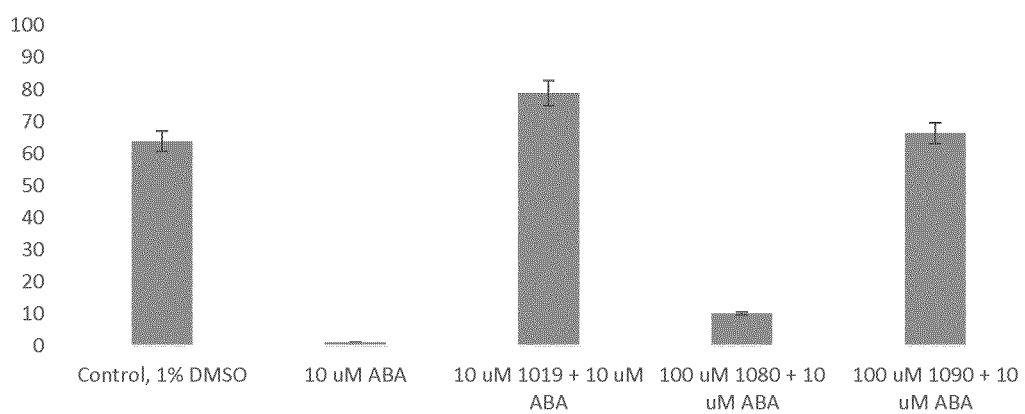
Figure 6A:
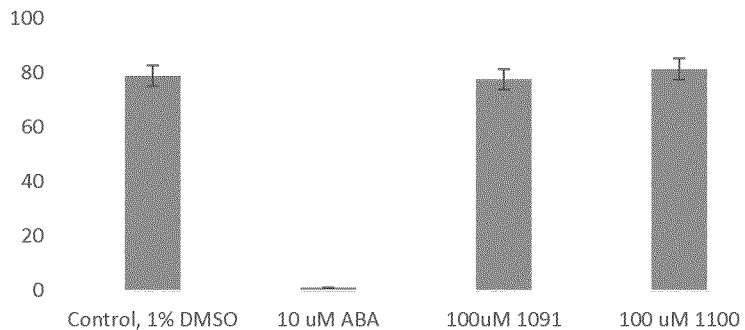
FIG. 6A, FIG. 6B and FIG. 6C are bar graphs showing lentil seed germination assays with exemplary compounds 1091 and 1100.
Figure 6B:
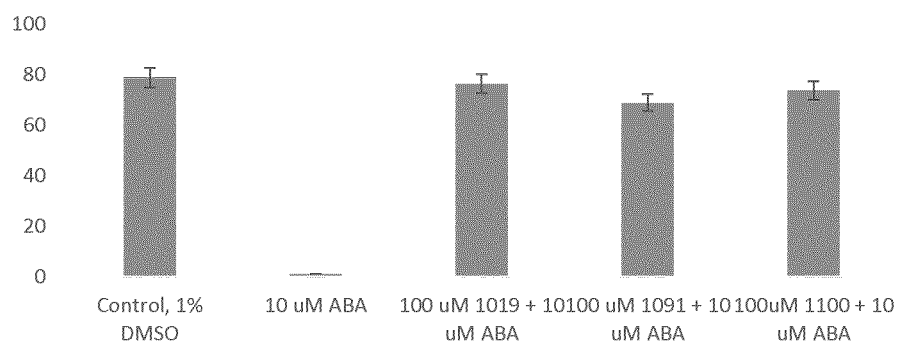
Figure 6C:
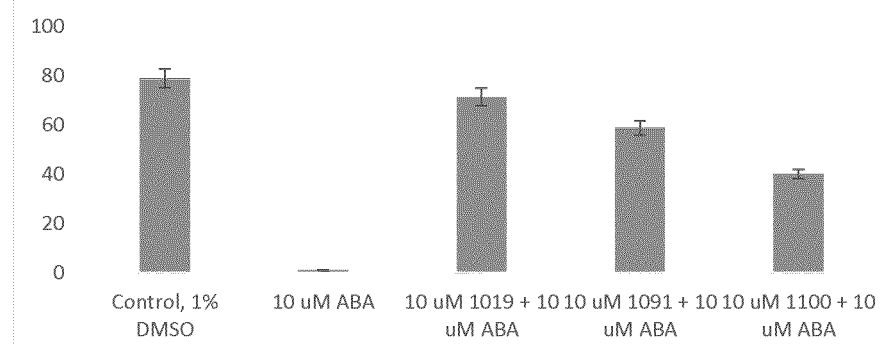
Figure 7A:
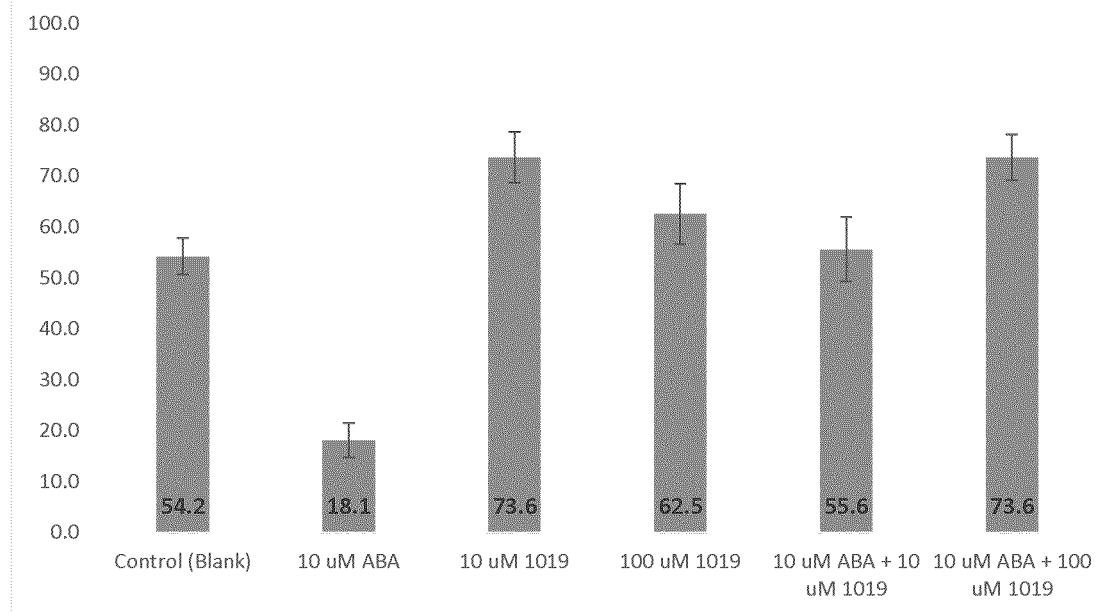
FIG. 7A and FIG. 7B are graphs showing soybean germination assays withexemplary compound 1019.
Figure 7B:
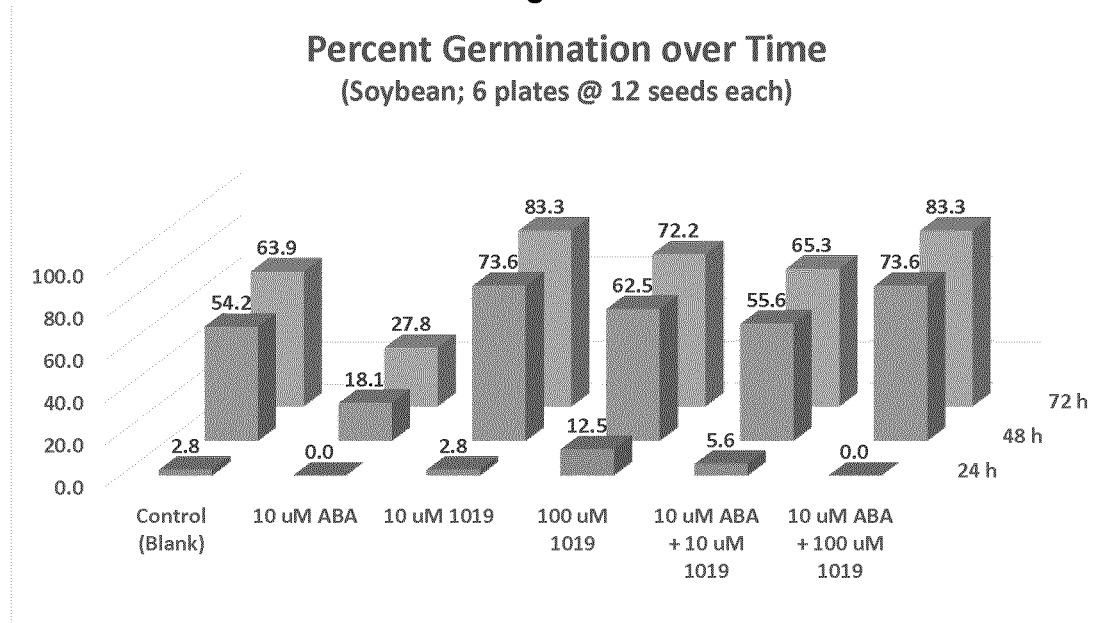
Figure 8:
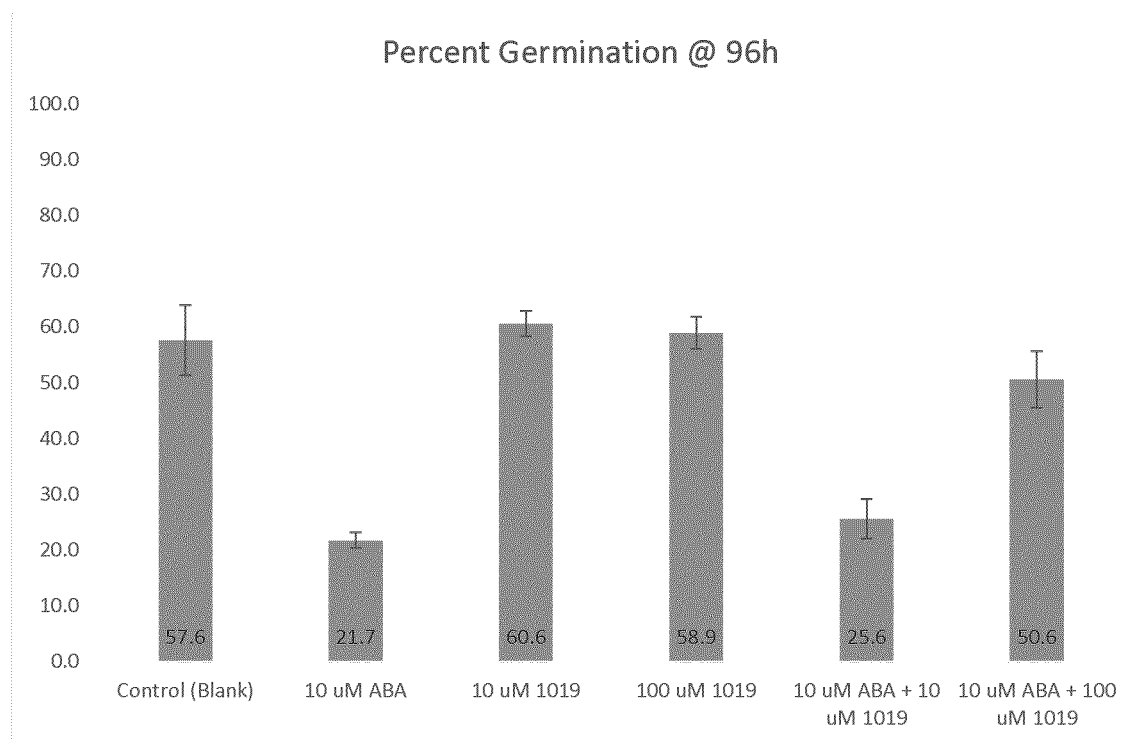
FIG. 8 is a bar graph showing canary seed germination assays with exemplary compound 1019 and shows effects of ABA and/or exemplary compound 1019.

As shown in FIG. 5, lentil seed germination in the presence of 10 μM ABA was promoted by 10 μM exemplary compound 1019 and 10 μM exemplary compound 1019 plus 10 μM ABA and by 100 μM exemplary compound 1090 and 100 μM exemplary compound 1090 plus 10 μM ABA and both compound treatments were comparable or higher in germination percentage than control. Lentil seed germination was found to be weakly promoted by 100 μM exemplary compound of Formula (II) 1080 in the presence of 10 μM ABA compared to control. In FIG. 6 A-C, data is presented comparing the effects of exemplary compound 1019 with exemplary compounds 1091 and 1100. The exemplary compounds 1091 and 1100 at 100 μM had no effect on seed germination compared to control. In FIG. 6B 100 μM solutions of exemplary compounds 1019, 1091 and 1100 overcame the effect of added 10 μM ABA. In FIG. 6C, the results of comparison of 10 μM ABA plus 10 μM of either exemplary compounds 1019, 1091 or 1100 are displayed. All three were found to be effective antagonists, with the strongest antagonist in this assay being exemplary compound 1019, followed by exemplary compound 1091 and exemplary compound 1100. Exemplary compound 1059 and 1063 were found to have no agonist activity and weak antagonist activity when tested at 10 uM versus 10 uM ABA (data not shown).

Example 15: Studying the Effect of Exemplary Compounds of the Application on Soybean (AAC Edward; 2018) Germination Methodology For each treatment 6 replicates of 10 seeds were plated into petri dishes lined with two filter papers and 10 mL of test solution. The covered dishes were stored at room temperature in the dark. Germinated seeds were counted over 24 hours. The following dosages were used when studying the effect of exemplary compounds of the application on soybean germination: control 1% DMSO. 10 μM ABA, 10 μM exemplary compound 1019, 100 um exemplary compound 1019, 10 μM exemplary compound 1019 plus 10 μM ABA and 100 uM exemplary compound 1019 plus 10 μM ABA.

Results

The results are very similar to those found in lentil seed germination studies. Both were carried out with the exemplary compound 1019 and the exemplary compound alone at 10 or 100 µM concentration did not affect seed germination. However in the presence of 10 µM ABA both 10 and 100 µM exemplary compound 1019 overcame the inhibition caused by ABA.

Example 16: Studying the Effect of Exemplary Compounds of the Application on Canary Seed Germination (CDC Bastia; 2018; CANYT1 rep1; Kernen)

Methodology

For each treatment 6 replicates of 30 seeds were plated into petri dishes lined with two filter papers and 10 mL of test solution. The covered dishes were stored at room temperature in the dark. Germinated seeds were counted over 24 hours. The following dosages were used when studying the effect of exemplary compounds on soybean germination: control 1% DMSO. 10 µM ABA, 10 µM exemplary compound 1019, 100 µM exemplary compound 1019, 10 µM exemplary compound 1019 plus 10 µM ABA and 100 µM exemplary compound 1019 plus 10 µM ABA.

Results

Neither concentration of exemplary compound 1019 affected germination of canary seed. 100 µM of exemplary compound 1019 overcame inhibition by 10 µM ABA on day 4 while 10 µM exemplary compound 1019 did not.

Example 17: Studying the Effects of Exemplary Compounds of the Application on Hard Red Spring Wheat Seedling Growth Methodology For each treatment 3 replicates of 10 seeds were plated into petri dishes lined with two filter papers and 10 mL of test solution. The covered dishes were stored at room temperature in the dark. At 72 hours, germinated seeds were scored for root length and shoot length. The following dosages were used when studying the effect of the exemplary ABA analogues of the application on wheat shoot and root growth: control 1% DMSO. 10 µM ABA, 10 µM 1019, 100 µM exemplary compound 1019, 10 µM exemplary compound 1019 plus 10 µM ABA (10:1) and 100 µM exemplary compound 1019 plus 10 µM ABA (1:1).

Results

Figure 9A:
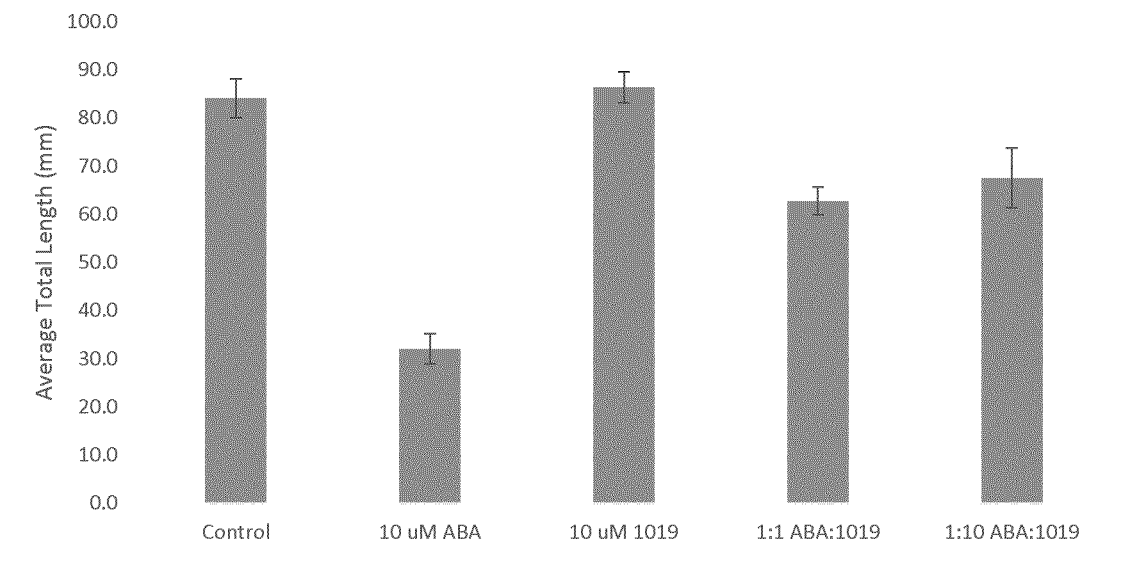
FIG. 9A and FIG. 9B are bar graphs showing the results of Hard Red Spring wheat seedling growth studies with exemplary compound 1019.
Figure 9B:
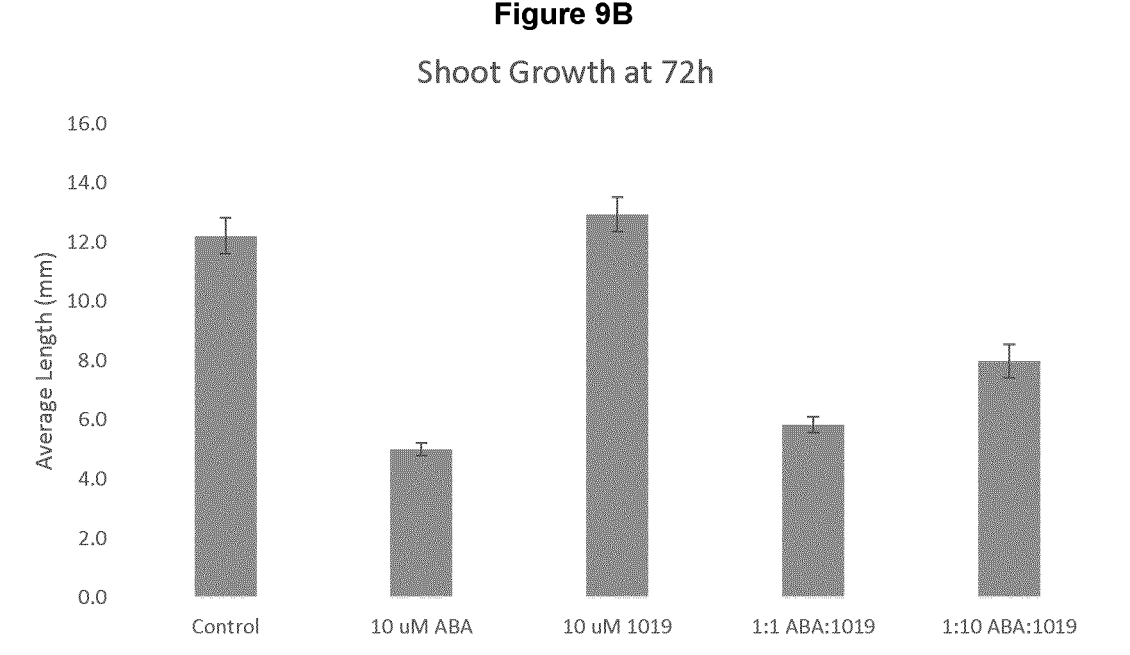

Root growth was not affected by 100 µM exemplary compound 1019 alone, but was by 10 µM ABA. 100 µM exemplary compound 1019 plus 10 µM ABA and 10 µM exemplary compound 1019 and 10 µM (FIG. 9 A) ABA both restored root growth to close to control length. Shoot growth was not inhibited by 100 µM exemplary compound 1019 and was inhibited by 10 µM ABA. Growth of shoots was restored with exemplary compound 1019, but to a lesser extent than root growth (FIG. 9 B).

Example 18: Studying the Effect of Exemplary Compounds of the Application on Canola Seed (Nutrien PV200) Germination Methodology For each treatment 6 replicates of 40 seeds were plated into petri dishes lined with two filter papers and 10 mL of test solution. The covered dishes were stored at room temperature in the dark. Germinated seeds were counted every 2 days for 8 days. The following dosages were used when studying the effect of exemplary compounds on canola germination: control 1% DMSO. 10 µM ABA, 100 µM 1019, and 100 µM 1019 plus 10 µM ABA.

Results

Figure 10:
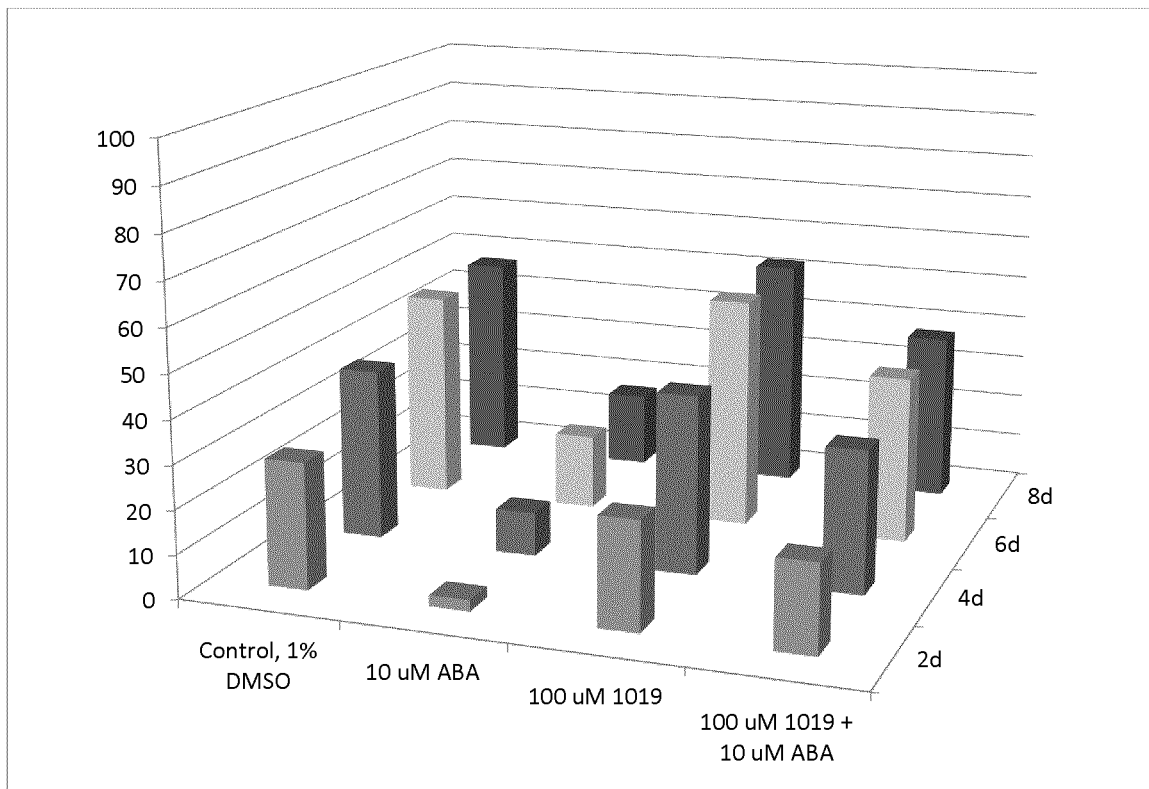
FIG. 10 is a graph showing canola seed germination assay with exemplary compound 1019 and shows effects of ABA and/or exemplary compound 1019 at 2 days, 4 days, 6 days and 8 days post treatment.

As shown in FIG. 10, 10 µM ABA inhibited seed germination throughout the 8 day study. The exemplary compound 1019 at 100 µM did not significantly affect germination compared to the control treatment. With the 100 µM exemplary compound 1019 plus 10 µM ABA treatment, the extent of germination was restored to near control levels.

Example 19: Studying the Effect of Exemplary Compound 1019 on Rice, Barely, Wheat and Sorghum Seed Germination/Radical Elongation Methodology Seeds were surface sterilized by incubation in 10% bleach for 20 min with shaking, then rinsed four times with sterile water. Four ml of test solutions were pipetted into petri dishes (100×15 mm) that contain a single filter paper. Fifteen seeds were added to each dish. For rice, barely, and wheat, the experiment involved five treatments (5 µM ABA; 5 µM ABA+10 µM 1019; 10 µM 1019; water control; water+EtOH+NaOH control), with three replications per treatment. For sorghum, treatments were 10 µM ABA; 10 µM ABA+20 µM 1019; 20 µM 1019; water control; water+EtOH+NaOH control. Dishes were sealed with Parafilm, and incubated in the dark at room temperature. Radical length was measured daily post emergence using ImageJ software; shown are 3 days post treatment for barley, wheat and sorghum and 4.5 days post treatment for rice.

Results

Figure 11A:
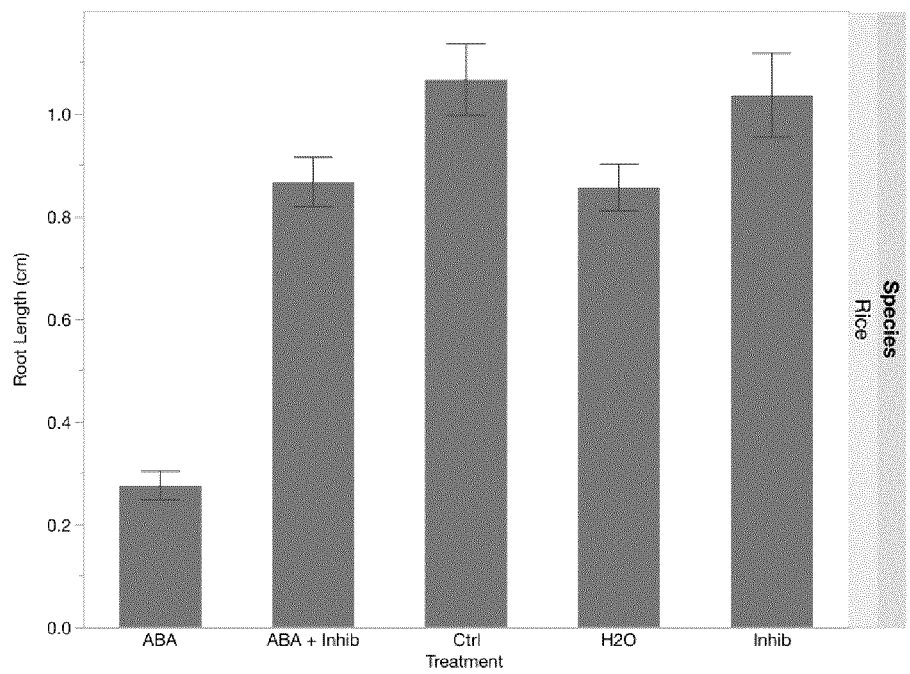
FIG. 11A, FIG. 11B, FIG. 11C and FIG. 11D are bar graphs showing the impact of ABA and exemplary compound 1019 on rice (FIG. 11A), barley (FIG. 11B), wheat (FIG. 11A), and Sorghum (FIG. 11D) radical elongation.
Figure 11B:
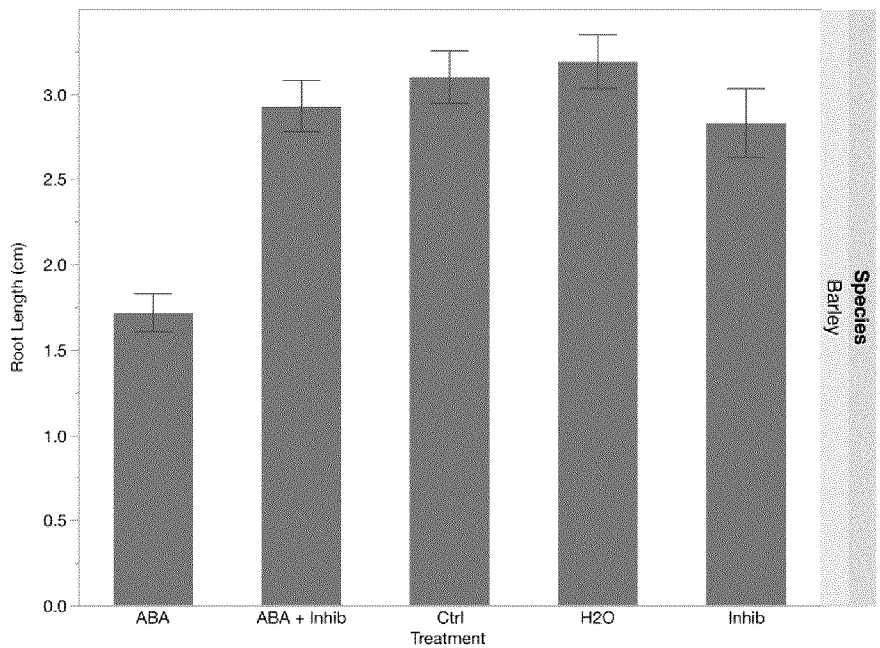
Figure 11C:
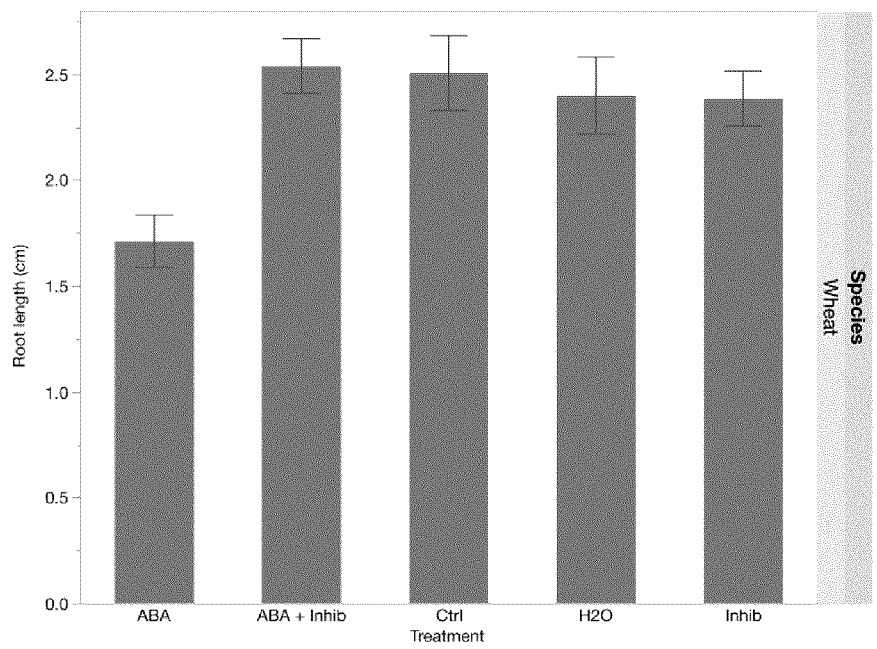
Figure 11D:
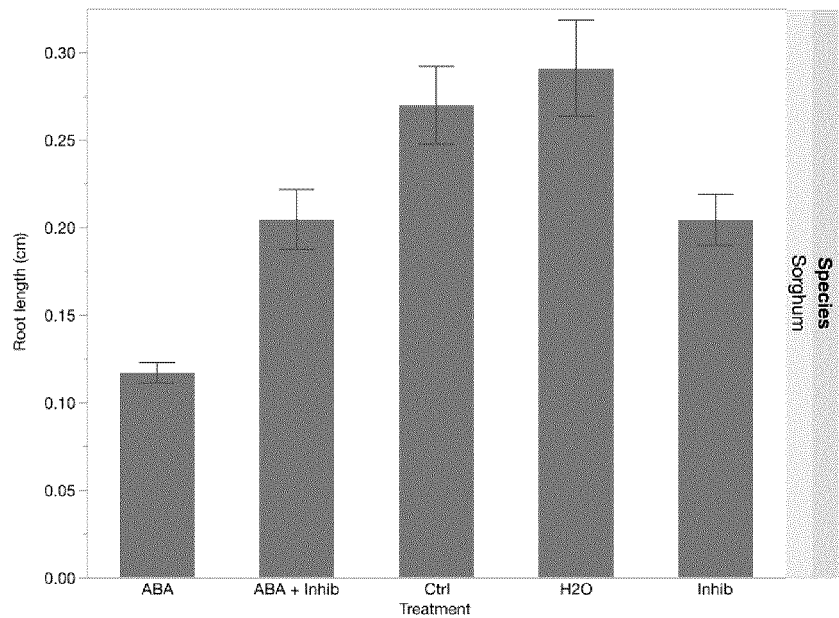

Using the concentrations and conditions described here, ABA did not inhibit seed germination, but did inhibit radical elongation. ABA inhibition of radical elongation was observed in assays with rice, barley and wheat at 5 µM ABA (FIGS. 11A-C), and for sorghum at 10 µM ABA (FIG. 11D). The higher rate of ABA application was used for sorghum because inconsistent results were observed at the lower rates. Addition of 10 µM exemplary compound 1019 blocked the effects of exogenously added ABA on rice, barley and wheat radical elongation (FIGS. 11A-C). The effects of exemplary compound 1019 on sorghum are not clear because the exemplary compound itself significantly reduces radical elongation (FIG. 11D).

Example 20: Studying the Effect of Exemplary Compound 1019 on Seed Germination in Wild and RIL Populations of Lentil Genotypes; and in Faba Bean Methodology Fifty four lentil genotypes were selected for the experiment based on the existing data on the number of days it takes them to emerge and days to flowering. The seeds of each genotype were scarified before sowing and subjected to 3 treatments. VWR 415 9 cm filter papers were placed inside VWR 100 mm plastic petri dishes. Each petri dish was labeled on both the top and the bottom. Ten seed from each line was place in a labelled petri dish. Each lentil or faba bean genotype was replicated 3 times and subjected to 3 treatments (total number of experimental petri dishes=531). Thus:

1. ABA exemplary compound solution [10 µM exemplary ABA analog compound 1019 in 1% DMSO, 99% H$_2$O (LL10.1014.1) NaSaH (SL-1-16-1-53)]
2. No exemplary ABA analogue solution (1% DMSO, 99% H$_2$O)
3. Distilled water—control Seven milliliters of either exemplary ABA analogue solution, solution with no exemplary ABA analogue or distill water (control) was added into the corresponding labelled petri dishes containing the 10 scarified lentil seeds. For faba, bean, 10 ml because of their large seed size. The petri dishes were placed in a dark cupboard. Two digital temperature and humidity loggers (Tinytag) were placed inside the cupboards to monitor environmental conditions.

Germination was considered for a seed when a tiny radicle at least 5 mm or greater had emerged from the seed. The number of seeds that germinated was counted and recorded at 48 and 96 hours; and at 7 days. Some of the genotypes of interest were photographed (AF-S Micro NIK-KOR 60 mm 1:2.8G camera) for comparison purpose. However, an excel sheet showing all results is available. At 48 hours, a total of 22 genotypes and their replicates were selected from the petri dishes treated with exemplary compound and distilled water were transplanted into pots (for faba bean) and trays (for lentils) in order to assess the length of time they took to flower while the rest of the petri dishes were kept till the end of the experiment that lasted a week.

The average temperature in the cupboards was 22.5° C. (±0.3) while the relative humidity ranged from 52.4 to 80.7 percent for the duration of the experiment. Studies carried out by Linda Gorim and Devini De. Silva, University of Saskatchewan Results Of the 54 lentil genotypes screened for response to exemplary compound 101-9 in improving germination rate over 4 days, 18 responded positively. Of the responsive genotypes four were *L. orientalis*, and six were *L. nigricans* and the remaining belonged either to the other wild lentil genotypes or RIL lines. For example, the genotype *L. nigricans* IG-72551 seeds had 100% germination at 2 days when exemplary compound 1019 was utilized while the water and solvent control had no seeds germinated at 4 days. Also, *L. orientalis* IG72770 treated with exemplary compound 1019 had 40% germination at day 2, 75% at day 3 and 100% at day 4 while both controls had zero germination in the same time period.

Overall, for all genotypes that responded to exemplary compound 1019, the treatment with the exemplary compound eliminated the variable germination rates that were observed between replicates in the controls and during emergence especially in wild germplasm. Therefore, exemplary compound 1019 does not only speed up germination rates but also resulted in germination uniformity. This significant reduction in germination time can have a significant impact on the number of crossing block that are carried per year in the lentil breeding program; i.e. many more crossed carried out per year. However, there was no significant effect of the exemplary compound 1019 on germination rates in faba bean nor did it significantly affect the days to flowering in either legume.

Example 21: Studying the Effect of Exemplary Compound 1019 on Lentil Germination, Emergence & Time to Flowering Methodology
Abbreviations:
DSTG=Days from seeding to germination
DSTE=Days from seeding to Emergence
DSTF=Days from seeding to flowering
DSTH=Days from seeding to harvesting of first seed (F7 was not included because the purpose of this generation was to harvest as many seeds as possible)
$GA_3$=gibberellic acid
DMSO=solvent required for dissolving 1019-ABA F7 Experiment Objective: Testing the effect of soaking seeds of the F7 generation in four solutions listed below.

Treatments: water, DMSO, 1019-ABA, and 1019-ABA for 1 day followed by 100 µM $GA_3$ Plant material: Seeds derived from a cross between *L. culinaris* var Redberry and *L. culinaris* ssp. *orientalis* IG72595

Experimental set up: 207 RIL-lines in total; 4 seeds (repetitions) per line; 4 treatments Data collection: Days from seeding to germination (DSTG), days from seeding to emergence (DSTE), and Days from seeding to first flower were counted. Days from seeding to first harvest was not determined because we needed as many seeds as possible in this generation.

Results

Figure 12:
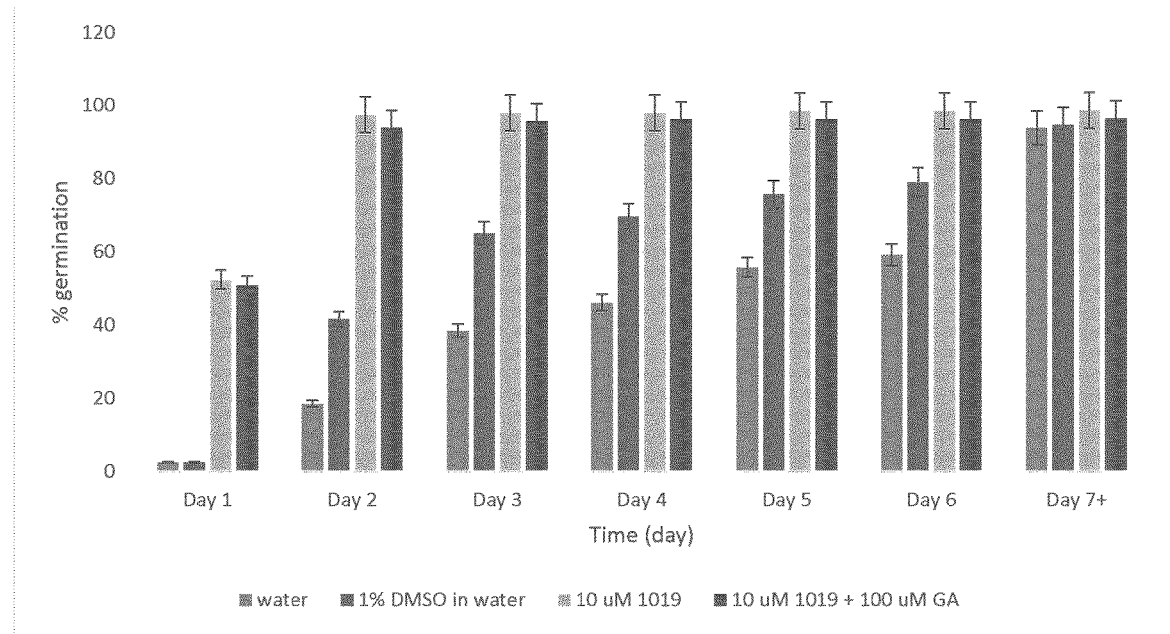
FIG. 12A is a bar graph showing the results of the lentil germination assays with exemplary compound 1019 and GA, and showing the effect of water (first bar), 1% DMSO in water (second bar), 10 uM 1019 (third bar) and 10 uM 1019+100 uM GA (fourth bar) on lentil germination at day 1 to day 7 post treatment.
FIG. 12B is a bar graph showing the results of the lentil emergence assays with exemplary compound 1019 and GA, and showing the effect of water (first bar), 1% DMSO in water (second bar), 10 uM 1019 (third bar) and 10 uM 1019+100 uM GA (fourth bar) on lentil germination at day 3 to day 9 post treatment.

Days to germination (DSTG), emergence (DSTE), time to flowering (DSTF) and first harvest (DSTH) were determined during the development of a recombinant inbred line (RIL) developed from a cross between *L. culinaris* var Redberry and *L. culinaris* ssp. *orientalis* IG72595. The aim of the project was to find and incorporate *Aphanomyces* root rot resistance into the cultivated lentil, and the *L. orientalis* accession was identified with improved resistance. During the development of this RIL line speed breeding techniques were applied i.e. warmer temperatures, longer day length, higher light intensity, restricted pot volume etc. In generation F5, the exemplary compound became available and was tested on germination and emergence. It was noted that not only did seeds germinate and emerge faster but that days to flowering was also reduced. This resulted in a shorter generation length i.e. days from seeding to harvest of first seed. The F7 generation was set up as a proper experiment with four treatments i.e. 1019, water, DMSO (solvent needed for dissolving exemplary compound 1019), and exemplary compound 1019 for one day followed by 100 µM $GA_3$ (FIG. 12).

TABLE 1

Number of lines seeded per generation (F2-F7), number of seeds germinated & emerged, as well as number of days from seeding to germination, emergence, flowering & harvest.

| Generation | Seeded | Germ. | Emerged | DSTG | DSTE | DSTF | DSTH | |
|---|---|---|---|---|---|---|---|---|
| F2 | 282 | 282 | 282 | N.D. | N.D. | 37.58 | 58.07 | |
| F3 | 282 | 282 | 282 | N.D. | N.D. | 39.20 | 69.16 | |
| F4 | 261 | 257 | 248 | 2.70 | 6.33 | 36.51 | 54.84 | |
| F5 | 231 | 230 | 225 | 2.18 | 4.93 | 28.22 | 45.41 | (Compound 1019) |

TABLE 1-continued

Number of lines seeded per generation (F2-F7), number of seeds germinated & emerged, as well as number of days from seeding to germination, emergence, flowering & harvest.

| Generation | Seeded | Germ. | Emerged | DSTG | DSTE | DSTF | DSTH | |
|---|---|---|---|---|---|---|---|---|
| CVF6 | 226 | 226 | 226 | 1.12 | 4.03 | 26.14 | 44.02 | (Compound 1019) |
| F7 | 819 | 816 | 791 | 1.49 | 4.31 | 24.94 | N.D | (Compound 1019) |

Table 2 shows that 99% of seeds germinated in the exemplary compound 1019 treatment compared to only 96% when seeds were germinated in water. Table 2 below shows that 99% of seeds germinated within 2 days in the exemplary compound 1019 treatment. In contrast, seeds soaked in water germinated much slower over a longer time period i.e. only 20% germinated within 2 days. Surprisingly, DMSO alone also speeded up germination but was slower by one day and the germination rate was lower as well.

TABLE 2

Overview of seeding and germination data

| Treatment | Line # | Seed # | Lost | % Lost | Seeds | Germ. | % Germ. |
|---|---|---|---|---|---|---|---|
| Water | 207 | 822 | 16 | 2.0 | 806 | 770 | 96.4 |
| DMSO | 207 | 817 | 12 | 1.5 | 805 | 779 | 96.8 |
| 1019&GA | 207 | 821 | 7 | 0.9 | 814 | 791 | 97.2 |
| 1019-ABA | 207 | 819 | 3 | 0.4 | 816 | 807 | 98.9 |
| Total | | 2460 | 35 | 4.3 | 2425 | 2340 | |
| Average | | 615.0 | 8.75 | 1.1 | 606.3 | 585.0 | 96.5 |

Figure 12B:
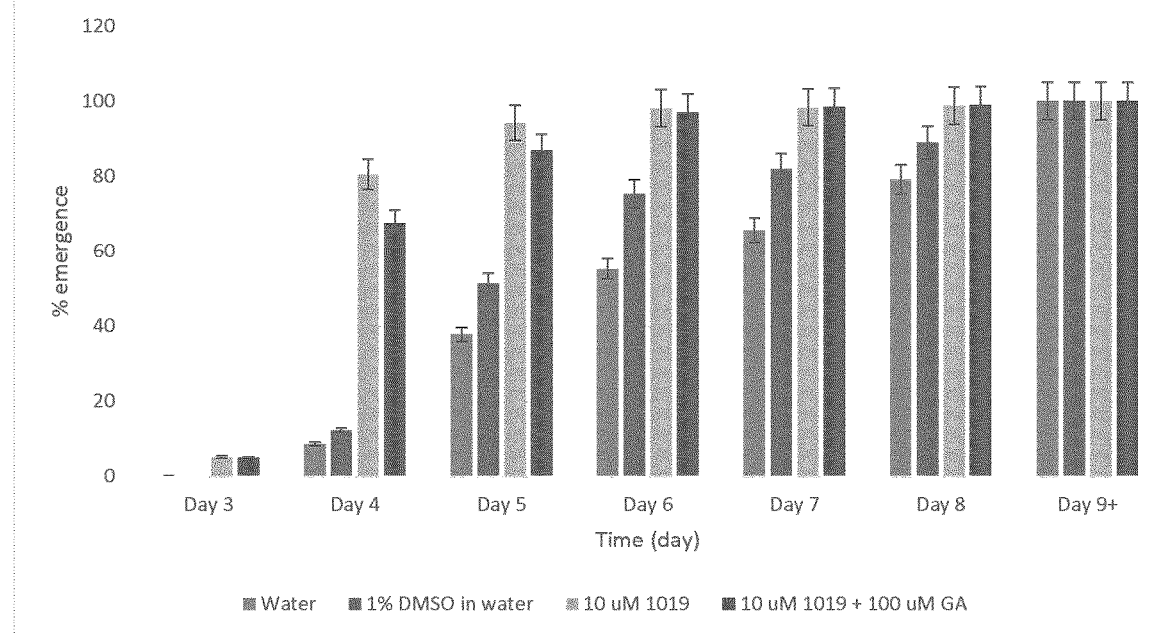

Four days after seeding 81% of the exemplary compound 1019-treated seeds had already emerged compared to 11% in the DMSO and 7% in the water treatments (FIG. 12B). Therefore, seeds treated with exemplary compound 1019 not only germinated faster and over a shorter time period but also emerged faster and at a rate of 100% compared to 89% and 84%, respectively. It should be noted that DMSO had little effect on emergence.

Next, we analyzed the number of days from seeding to flowering for each treatment. Exemplary compound 1019 treated seeds flowered 4 days earlier on average than plants from the water treatment (Table 3).

TABLE 3

| Treatment | DSTF |
|---|---|
| Water | 29.4 |
| DMSO | 27.6 |
| GA&1019 | 25.6 |
| 1019 | 24.9 |

In conclusion, exemplary compound 1019 significantly reduced the number of days from seeing to germination (root growth) compared to the controls (water and 1% DMSO in water). Seeds needed 1.5 days to germinate with exemplary compound 1019 and 4.5 days with water. Exemplary compound 1019 did not improve emergence (shoot growth) compared to the controls. It took 5.3 days seedlings emerged faster after using DMSO (5.1 days) or 1019+GA$_3$ (5.1 days) but differences were small. Using exemplary compound 1019 for germination resulted in faster flowering compared to the controls. It took 1019 plants 25 days to develop the first flower. It took 28 (1% DMSO in water) and 29 (water) days for plants to flower. Exemplary compound 1019 treatment resulted in plants flowering 4 days earlier. Using exemplary compound 1019 treatment resulted in seeds germinating (ca. 99%) within 2 days. Compared to seeds imbibed in water in which case germination was slow and took place over 9 days. The synchronizing of germination improves the process significantly.

Example 22: Studying the Effect of Exemplary Compound of the Application on ABA-Inducible Gene Expression in *Arabidopsis*

Methodology

Transgenic MKKK18GUS *Arabidopsis* plants harbor an α-glucuronidase (GUS) reporter gene fused to an ABA-inducible promoter of the MKKK18 gene (Okamoto et al. 2013). Six-day-old MKKK18GUS plants were treated with ABA1019 alone or both ABA1019 and ABA for 6 hours. Plants were then stained with 5-bromo-4-chloro-3-indolyl-beta-D-glucuronic acid cyclohexyl ammonium salt (X-Glc) for 14 hours, and destained with 70% ethanol.

Results

Figure 13:
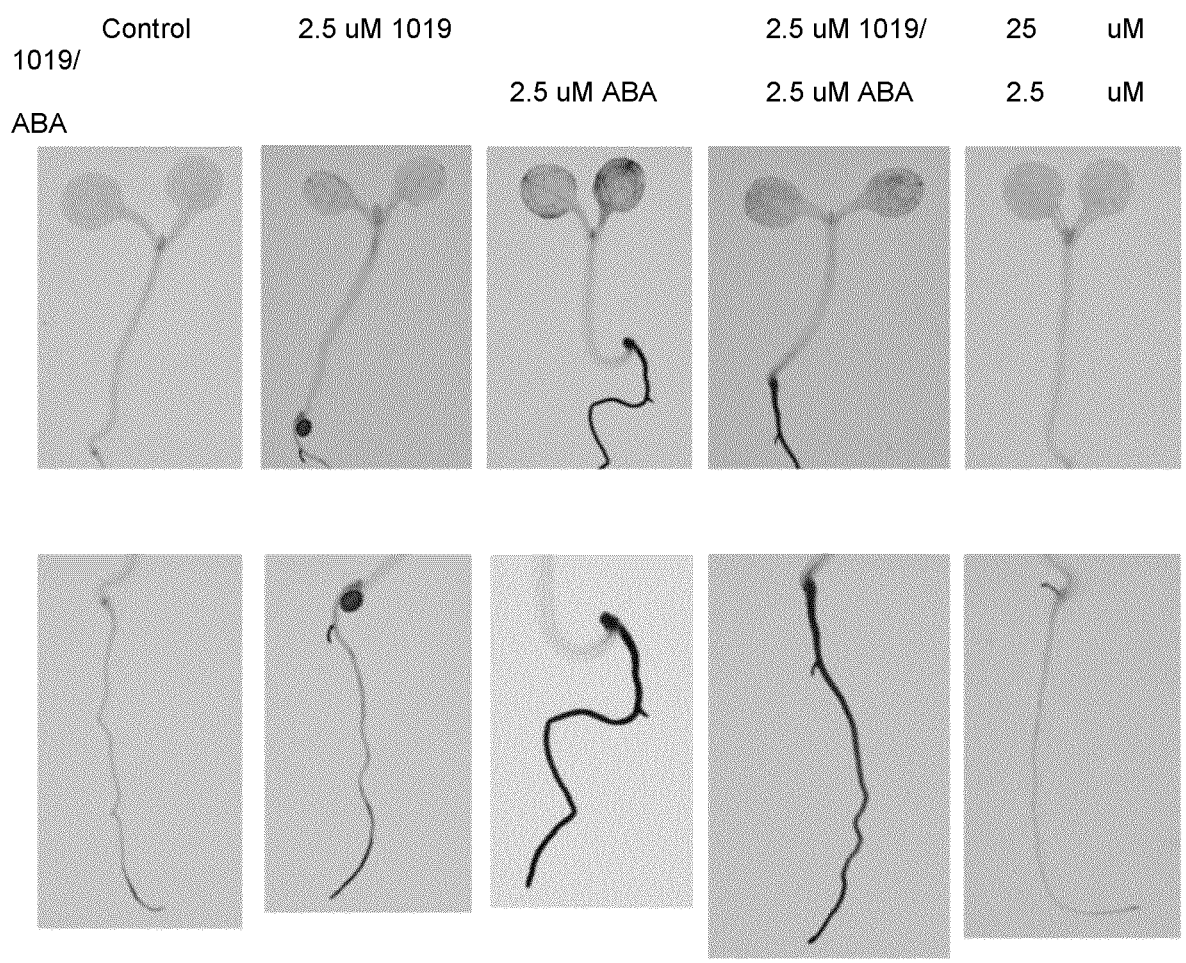
FIG. 13 shows the effect of exemplary compound 1019 on ABA inducible gene expression.

As shown in FIG. 13 exemplary compound 1019 at 2.5 μM has a weak agonist activity when applied alone, while it showed a potent antagonist effect in a dose dependent manner when co-applied with 2.5 M ABA. When applied at 1:1 ratio with ABA, a reduction in the GUS staining was observed when compared to application of ABA alone. Increasing the ratio of exemplary compound 1019 to ABA to 10:1 resulted in abolition of the ABA GUS stain showing clear antagonism of ABA by exemplary compound 1019.

Example 23: Studying the Effect of Exemplary Compound 1019 on the Plant Pathogen *Botrytis Cinerea*

Methodology

Figure 14:
FIG. 14 shows the antimicrobial activity of exemplary compound 1019. *Arabidopsis* plants were sprayed twice with Mock and a solution of exemplary compound 1019 (100 μM), and leaves were detached for inoculation. Inoculated leaves were incubated under light for 24 h before photographs were taken.

Analogs of ABA that antagonize ABA have the potential to overcome negative effects of ABA in plant pathogen interactions. To test this hypothesis, we conducted a pathogenicity test on leaves of *Arabidopsis thaliana* plants against a virulent *Botrytis cinerea* strain of *Arabidopsis* (Mathys et al., 2012).[21] Col-0 plants were sprayed with exemplary compound 1019 (100 μM) or mock control. After 24 h, leaves were detached and inoculated with mycelium blocks of *Botrytis cinerea* grown on PDA medium plates. Results Pathogenicity assays revealed that symptom development was slower on leaves treated with the exemplary compound 1019 than that of mock control. At 24 hours post inoculation, disease lesions surrounding the inoculated sites were observed in control leaves, but smaller lesions appeared on the leaves treated with the exemplary compound (FIG. 14). These preliminary results indicate that the treatment with exemplary compound 1019 partially inhibits the disease development caused by ABA-producing fungal pathogen, *B.* cinerea. The delay of disease development could be caused by either a direct inhibitory impact on *B. cinerea* development or activation of host defenses.

FULL CITATIONS FOR DOCUMENTS REFERRED TO IN THE APPLICATION

A. Benson, C. L., Michal Kepka, M., Wunschel, C., Rajagopalan, N., Nelson, K. N., Christmann, A., Abrams, S. R., Grill, E., Loewen, M. C. 2015 Abscisic acid analogs as chemical probes for dissection of abscisic acid responses in *Arabidopsis Thaliana*. Phytochemistry, 113 96-107. doi.org/10.1016/j.phytochem.2014.03.017

B. Boyd, J.; Gai, Y.; Nelson, K. M.; Lukiwski, E.; Talbot, J.; Loewen, M. K.; Owen, S.; Zaharia, L. I.; Cutler, A. J.; Abrams S. R.; Loewen, M. C. Bioorg. Med. Chem. 2009, 17, 2902-2912.

C. Hirai, N., Fukui, H., Koshimizu, K. 1978 A novel abscisic acid catabolite from seeds of *Robinia pseudoacacia* Phytochemistry 17: 1625-7.

D. Nonogaki H. 2014. Seed dormancy and germination-emerging mechanisms and new hypotheses. Front Plant Sci. 5: 233.

E. Nyangulu, J. M.; Galka, M. M.; Jadhav, A.; Gai, Y.; Graham, C. M.; Nelson, K. M.; Cutler, A. J.; Taylor, D. C.; Banowetz, G. M.; Abrams, S. R. J. Am. Chem. Soc. 2005, 127, 1662-1664.

F. Rajagopalan, N., Nelson, K, N., Douglas, A. F., Jheengut, V., Alarcon, I. Q., McKenna S., Surpin, M., Loewen, M. C., Abrams, S. R. 2016 Abscisic Acid Analogues That Act as Universal or Selective Antagonists of Phytohormone Receptors. Biochemistry 55, 5155-5164 doi/abs/10.1021/acs.biochem.6b00605

G. Slater, M. H., Yuan, H. Y., Lulsdorf, M. M., Vandenberg, A. L., Zaharia, I., Han, X., Abrams, S. R. 2013 Comprehensihormone profiling of the developing seeds of four grain legumes Plant Cell Rep in press DOI 10.1007/s00299-013-1505-3

H. Takeuchi, J.; Okamoto, M.; Akiyama, T.; Muto, T.; Yajima, S.; Sue, M.; Seo, M.; Kanno, Y.; Kamo, T.; Endo, A.; Nambara E.; Hirai, N.; Ohnishi, T.; Cutler, S. R.; Todoroki, Y. Nat. Chem. Biol. 2014, 10, 477-482.

I. Walker-Simmons M K, Anderberg R J, Rose P A, Abrams S R. 1992. Optically pure ABA analogs: Tools for relating germination inhibition and gene expression in wheat embryos. Plant Physiol 99:501-507.

J. Wilen R W, Hays D B, Mandel R M, Abrams S R, Moloney M M. 1993. Competitive inhibition of abscisic acid-regulated gene expression by stereoisomeric acetylenic analogs of abscisic acid. Plant Physiol 101:469-476.

(1) Nonogaki, H. Seed Dormancy and Germination-Emerging Mechanisms and New Hypotheses. Front. Plant Sci. 2014, 5, 233.

(2) Walker-Simmons, M. K.; Anderberg, R. J.; Rose, P. A.; Abrams, S. R. Optically Pure Abscisic Acid Analogs-Tools for Relating Germination Inhibition and Gene Expression in Wheat Embryos. Plant Physiol. 1992, 99 (2), 501-507.

(3) Wilen, R. W.; Hays, D. B.; Mandel, R. M.; Abrams, S. R.; Moloney, M. M. Competitive Inhibition of Abscisic Acid-Regulated Gene Expression by Stereoisomeric Acetylenic Analogs of Abscisic Acid. Plant Physiol. 1993, 101 (2), 469-476.

(4) Benson, C. L.; Kepka, M.; Wunschel, C.; Rajagopalan, N.; Nelson, K. M.; Christmann, A.; Abrams, S. R.; Grill, E.; Loewen, M. C. Abscisic Acid Analogs as Chemical Probes for Dissection of Abscisic Acid Responses in *Arabidopsis Thaliana*. Phytochemistry 2015, 113, 96-107.

(5) Abrams, S. R.; Loewen, M. C. Chemistry and Chemical Biology of ABA; Elsevier Ltd, 2019; Vol. 92.

(6) Chakraborty, S.; Newton, A. C. Climate Change, Plant Diseases and Food Security: An Overview. Plant Pathol. 2011, 60 (1), 2-14.

(7) Lievens, L.; Pollier, J.; Goossens, A.; Beyaert, R.; Staal, J. Abscisic Acid as Pathogen Effector and Immune Regulator. Front. Plant Sci. 2017, 8 (April), 1-15.

(8) Forlani, S.; Masiero, S.; Mizzotti, C. Fruit Ripening: The Role of Hormones, Cell Wall Modifications, and Their Relationship with Pathogens. J. Exp. Bot. 2019, 70 (11), 2993-3006.

(9) Cao, F. Y.; Khan, M.; Taniguchi, M.; Mirmiran, A.; Moeder, W.; Lumba, S.; Yoshioka, K.; Desveaux, D. A Host-Pathogen Interactome Uncovers Phytopathogenic Strategies to Manipulate Plant ABA Responses. Plant J. 2019, 187-198.

(10) Krattinger, S. G.; Kang, J.; Brsunlich, S.; Boni, R.; Chauhan, H.; Selter, L. L.; Robinson, M. D.; Schmid, M. W.; Wiederhold, E.; Hensel, G.; et al. Abscisic Acid Is a Substrate of the ABC Transporter Encoded by the Durable Wheat Disease Resistance Gene Lr34. New Phytol. 2019, 223 (2), 853-866.

(11) Peng, Z.; Hu, Y.; Zhang, J.; Huguet-Tapia, J. C.; Block, A. K.; Park, S.; Sapkota, S.; Liu, Z.; Liu, S.; White, F. F. *Xanthomonas Translucens* Commandeers the Host Rate-Limiting Step in ABA Biosynthesis for Disease Susceptibility. Proc. Natl. Acad. Sci. 2019, 201911660.

(12) Slater, S. M. H.; Yuan, H. Y.; Lulsdorf, M. M.; Vandenberg, A.; Zaharia, L. I.; Han, X.; Abrams, S. R. Comprehensive Hormone Profiling of the Developing Seeds of Four Grain Legumes. Plant Cell Rep. 2013, 32 (12), 1939-1952.

(13) Takino, J.; Kozaki, T.; Ozaki, T.; Liu, C.; Minami, A.; Oikawa, H. Elucidation of Biosynthetic Pathway of a Plant Hormone Abscisic Acid in Phytopathogenic Fungi. Biosci. Biotechnol. Biochem. 2019, 83 (9), 1642-1649.

(14) Mbengue, M.; Navaud, O.; Peyraud, R.; Barascud, M.; Badet, T.; Vincent, R.; Barbacci, A.; Raffaele, S. Emerging Trends in Molecular Interactions between Plants and the Broad Host Range Fungal Pathogens *Botrytis Cinerea* and *Sclerotinia Sclerotiorum*. Front. Plant Sci. 2016, 7 (MAR2016), 1-9.

(15) Rajagopalan, N.; Nelson, K. M.; Douglas, A. F.; Jheengut, V.; Alarcon, I. Q.; McKenna, S. A.; Surpin, M.; Loewen, M. C.; Abrams, S. R. Abscisic Acid Analogues That Act as Universal or Selective Antagonists of Phytohormone Receptors. Biochemistry 2016, 55 (36), 5155-5164.

(16) Takeuchi, J.; Okamoto, M.; Akiyama, T.; Muto, T.; Yajima, S.; Sue, M.; Seo, M.; Kanno, Y.; Kamo, T.; Endo, A.; et al. Designed Abscisic Acid Analogs as Antagonists of PYL-PP2C Receptor Interactions. Nat. Chem. Biol. 2014, 10 (6), 477-482.

(17) Wang, G, T.; Heiman, D.; Venburg, G; Nagano, E; Surpin, M; Lustig, J, H. Wo 2016/007587, 2016.

(18) Song, D.; Zhou, J.; Lai, L.; Alarcon, I.; Tar'an, B.; Abrams, S. Development of ABA Antagonists to Overcome ABA- and Low Temperature-Induced Inhibition of Seed Germination in Canola, Lentil, and Soybean. J. Plant Growth Regul. 2019.

(19) Arai, S.; Todoroki, Y.; Ibaraki, S.; Naoe, Y.; Hirai, N.; Ohigashi, H. Synthesis and Biological Activity of 3'-Chloro, -Bromo, and—Iodoabscisic Acids, and Biological Activity of 3'-Fluoro-8'-Hydroxyabscisic Acid. Phytochemistry 1999, 52 (7), 1185-1193.

(20) Cloutier, M.; Roudias, M.; Paquin, J.-F. Regioselective Gold-Catalyzed Hydration of CF3- and SF5-Alkynes. Org. Lett. 2019, 21 (10), 3866-3870.

(21) Mathys, J.; De Cremer, K.; Timmermans, P.; Van Kerkhove, S.; Lievens, B.; Vanhaecke, M.; Cammue, B.; De Coninck, B. Genome-Wide Characterization of ISR Induced in *Arabidopsis Thaliana* by *Trichoderma Hamatum* T382 Against *Botrytis Cinerea* Infection. Front. Plant Sci. 2012, 3, 108.

(22) Xu, J., Audenaert, K., Monica Hoft, M., De Vleesschauwer, D. Abscisic Acid Promotes Susceptibility to the Rice Leaf Blight Pathogen *Xanthomonas oryzae* pv *oryzae* by Suppressing Salicylic Acid-Mediated Defenses 2013 PLoS ONE 8(6): e67413. doi:10.1371/journal.pone.0067413.

The invention claimed is:

1. A compound of Formula (I) or an enantiomer, salt, and/or solvate thereof:

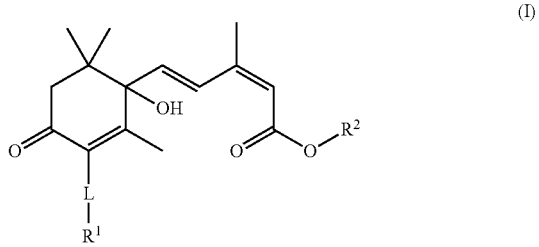

(I)

wherein

L is —C=C— or —C≡C—;

$R^1$ is $C_{1-10}$alkyl, $C_{2-10}$alkenyl, $C_{2-10}$alkynyl, $(CH_2)_{0-2}C_{3-10}$cycloalkyl, $(CH_2)_{0-2}$aryl, $(CH_2)_{0-2}$heterocycloalkyl, or $(CH_2)_{0-2}$heteroaryl, each being optionally substituted with one or more of halo, CN, OH, $NH_2$, $C_{1-10}$alkyl, $C_{2-10}$alkenyl, $C_{2-10}$alkynyl, $NH(C_{1-6}$alkyl), $N(C_{1-6}$ alkyl)$(C_{1-6}$alkyl), $OC_{1-6}$alkyl, $OC_{2-6}$alkenyl, $OC_{2-6}$alkynyl, $(CH_2)_{0-2}C_{3-10}$cycloalkyl, $(CH_2)_{0-2}$aryl, $(CH_2)_{0-2}$heterocycloalkyl, $(CH_2)_{0-2}$heteroaryl, $O(CH_2)_{0-2}C_{3-10}$cycloalkyl, $O(CH_2)_{0-2}$aryl, $O(CH_2)_{0-2}$heterocycloalkyl, or $O(CH_2)_{0-2}$heteroaryl, the latter 16 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl; and $R^2$ is H, $C_{1-10}$alkyl, $C_{2-10}$alkenyl, $C_{2-10}$alkynyl, cycloalkyl, aryl, heterocycloalkyl or heteroaryl, the latter 7 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl, wherein each alkyl, alkenyl, and alkynyl are optionally fluorosubstituted.

2. The compound of claim 1, wherein $R^1$ is $(CH_2)_{0-2}$aryl optionally substituted with one or more of halo, CN, OH, $NH_2$, $C_{1-10}$alkyl, $C_{2-10}$alkenyl, $C_{2-10}$alkynyl, $NH(C_{1-6}$alkyl), $N(C_{1-6}$alkyl)$(C_{1-6}$alkyl), $OC_{1-6}$alkyl, $OC_{2-6}$alkenyl, $OC_{2-6}$alkynyl, $(CH_2)_{0-2}C_{3-10}$ cycloalkyl, $(CH_2)_{0-2}$aryl, $(CH_2)_{0-2}$heterocycloalkyl, $(CH_2)_{0-2}$heteroaryl, $O(CH_2)_{0-2}C_{3-10}$cycloalkyl, $O(CH_2)_{0-2}$aryl, $O(CH_2)_{0-2}$heterocycloalkyl or $O(CH_2)_{0-2}$heteroaryl, the latter 16 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl, wherein each alkyl, alkenyl, and alkynyl are optionally fluorosubstituted.

3. The compound of claim 1, wherein $R^1$ is aryl optionally substituted with one or more of OH, halo, $C_{1-10}$alkyl, $OC_{1-6}$alkyl, or $O(CH_2)_{0-2}$aryl, wherein each alkyl, alkenyl, and alkynyl are optionally fluorosubstituted.

4. The compound of claim 1, wherein $R^1$ is $C_{1-10}$alkyl optionally substituted with one or more of halo, CN, OH, $NH_2$, $C_{1-10}$alkyl, $C_{2-10}$alkenyl, $C_{2-10}$alkynyl, $NH(C_{1-6}$alkyl), $N(C_{1-6}$alkyl)$(C_{1-6}$alkyl), $OC_{1-6}$alkyl, $OC_{2-6}$alkenyl, $OC_{2-6}$alkynyl, $(CH_2)_{0-2}C_{3-10}$cycloalkyl, $(CH_2)_{0-2}$aryl, $(CH_2)_{0-2}$heterocycloalkyl, $(CH_2)_{0-2}$heteroaryl, $O(CH_2)_{0-2}C_{3-10}$cycloalkyl, $O(CH_2)_{0-2}$aryl, $O(CH_2)_{0-2}$heterocycloalkyl, or $O(CH_2)_{0-2}$heteroaryl, the latter 16 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl, wherein each alkyl, alkenyl, and alkynyl are optionally fluorosubstituted.

5. The compound of claim 4, wherein $R^1$ is $C_{1-10}$alkyl optionally substituted with one or more of halo, CN, OH, $NH_2$, $C_{1-10}$alkyl, $C_{2-10}$alkenyl, or $C_{2-10}$alkynyl, wherein each alkyl, alkenyl, and alkynyl are optionally fluorosubstituted.

6. The compound of claim 1, wherein $R^1$ is $C_{2-10}$alkenyl optionally substituted with one or more of halo, CN, OH, $NH_2$, $C_{1-10}$alkyl, $C_{2-10}$alkenyl, or $C_{2-10}$alkynyl, wherein each alkyl, alkenyl, and alkynyl are optionally fluorosubstituted.

7. The compound of claim 1, wherein $R^1$ is $(CH_2)_{0-2}C_{3-10}$cycloalkyl optionally substituted with one or more of halo, CN, OH, $NH_2$, $C_{1-10}$alkyl, $C_{2-10}$alkenyl, $C_{2-10}$alkynyl, $NH(C_{1-6}$alkyl), $N(C_{1-6}$alkyl)$(C_{1-6}$alkyl), $OC_{1-6}$alkyl, $OC_{2-6}$alkenyl, $OC_{2-6}$alkynyl, $(CH_2)_{0-2}C_{3-10}$cycloalkyl, $(CH_2)_{0-2}$aryl, $(CH_2)_{0-2}$heterocycloalkyl, $(CH_2)_{0-2}$heteroaryl, $O(CH_2)_{0-2}C_{3-10}$cycloalkyl, $O(CH_2)_{0-2}$aryl, $O(CH_2)_{0-2}$heterocycloalkyl, or $O(CH_2)_{0-2}$heteroaryl, the latter 16 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl, wherein each alkyl, alkenyl, and alkynyl are optionally fluorosubstituted.

8. The compound of claim 7, wherein $R^1$ is $C_{3-10}$cycloalkyl optionally substituted with one or more of halo, CN, OH, $NH_2$, $C_{1-10}$alkyl, $C_{2-10}$alkenyl, or $C_{2-10}$alkynyl, wherein each alkyl, alkenyl, and alkynyl are optionally fluorosubstituted.

9. The compound of claim 1, wherein $R^2$ is H or $C_{1-10}$alkyl.

10. The compound of claim 1, wherein L is —C=C—.

11. The compound of claim 1, wherein L is —C≡C—.

12. The compound of Formula (I) or a salt, and/or solvate thereof of claim 1, wherein the compound has the following stereochemistry:

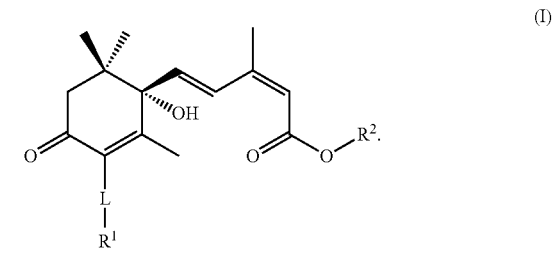

(I)

13. The compound of Formula (I) of claim 1 selected from the compounds listed below:
| Compound I.D | Structures |
|---|---|
| 1018 | 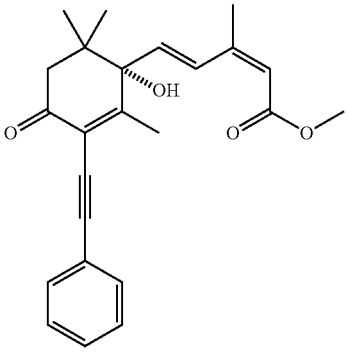 [SMILES: COC(=O)/C=C(C)\C=C\[C@@]1(O)C(C)=C(C#Cc2ccccc2)C(=O)CC1(C)C] |
| 1019 | 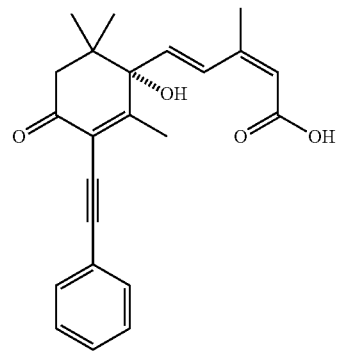 [SMILES: CC1=C(C#Cc2ccccc2)C(=O)CC(C)(C)[C@@]1(O)/C=C/C(C)=C\C(=O)O] |
| 1021 | 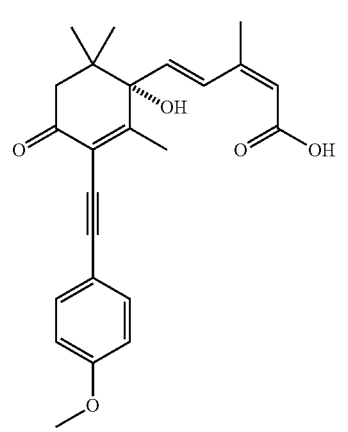 [SMILES: COc1ccc(C#CC2=C(C)[C@](O)(/C=C/C(C)=C\C(=O)O)C(C)(C)CC2=O)cc1] |
| 1022 | 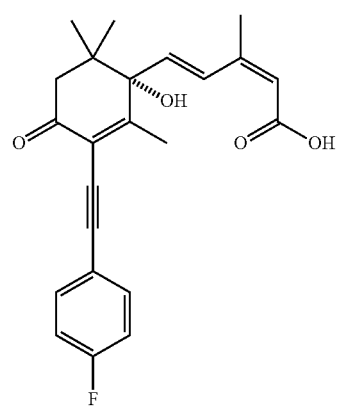 [SMILES: CC1=C(C#Cc2ccc(F)cc2)C(=O)CC(C)(C)[C@@]1(O)/C=C/C(C)=C\C(=O)O] |
| 1023 | 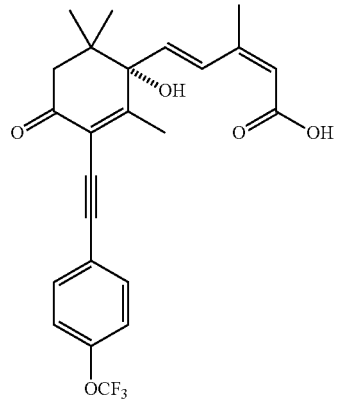 [SMILES: CC1=C(C#Cc2ccc(OC(F)(F)F)cc2)C(=O)CC(C)(C)[C@@]1(O)/C=C/C(C)=C\C(=O)O] |
| 1024 | 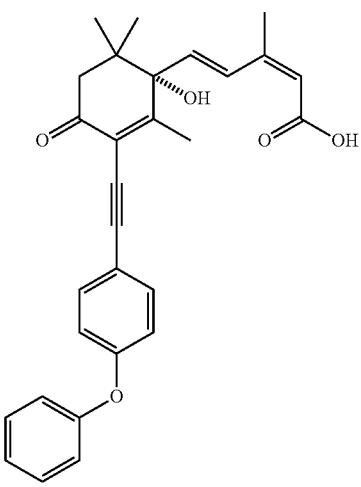 [SMILES: CC1=C(C#Cc2ccc(Oc3ccccc3)cc2)C(=O)CC(C)(C)[C@@]1(O)/C=C/C(C)=C\C(=O)O] |
| 1025 | 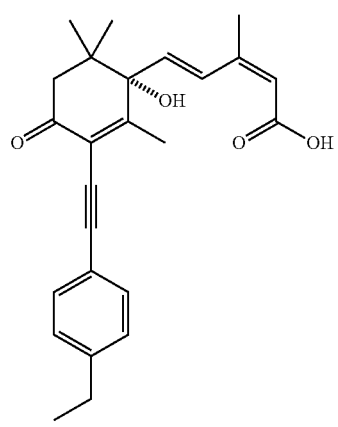 [SMILES: CCc1ccc(C#CC2=C(C)[C@](O)(/C=C/C(C)=C\C(=O)O)C(C)(C)CC2=O)cc1] |

| Compound I.D | Structures |
|---|---|
| 1059 | 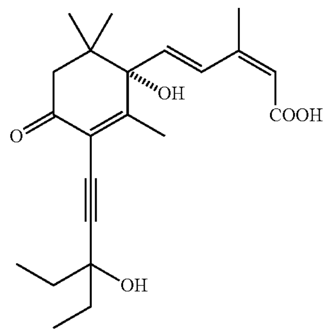 [SMILES: CCC(O)(C#CC1=C(C)[C@](O)(/C=C/C(C)=C\C(=O)O)C(C)(C)CC1=O)CC] |
| 1063 | 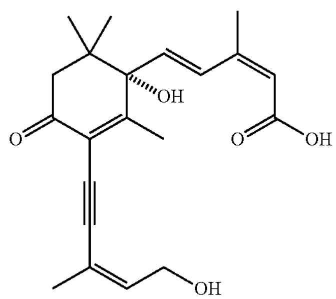 [SMILES: CC1=C(C#C/C(C)=C\CO)C(=O)CC(C)(C)[C@@]1(O)/C=C/C(C)=C\C(=O)O] |
| 1090 | 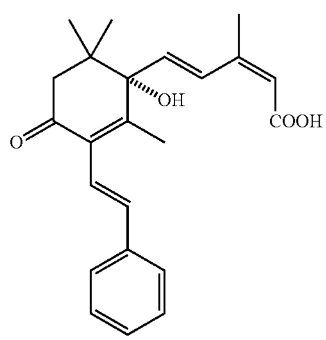 [SMILES: CC1=C(/C=C/c2ccccc2)C(=O)CC(C)(C)[C@@]1(O)/C=C/C(C)=C\C(=O)O] |
| 1091 | 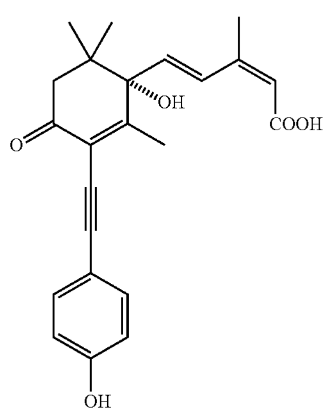 [SMILES: CC1=C(C#Cc2ccc(O)cc2)C(=O)CC(C)(C)[C@@]1(O)/C=C/C(C)=C\C(=O)O] |

| Compound I.D | Structures |
|---|---|
| 1100 | | or a salt, and/or solvate thereof.

14. A method for reducing adverse effects of an ABA response in a plant in need thereof comprising administering an effective amount of one or more compounds of claim 1 or salt and/or solvate thereof to the plant.

15. The method of claim 14, wherein the adverse effects of an ABA response include delayed or inhibited seed germination and/or plant dessication, over-ripening of fruit, slow bud breaking and/or slow plant growth.

16. The method of claim 14, wherein the adverse effects of an ABA response occur under stress conditions.

17. A method for reducing adverse effects of an ABA response in a plant in need thereof comprising administering an effective amount of one or more compounds of the Formula (II) or an enantiomer, salt, and/or solvate thereof, to the plant, (II)

wherein:

n is 0, 1, 2 or 3;

$R^3$ is selected from OH, halo, $C_{1-10}$alkyl, $OC_{1-6}$alkyl, and $O(CH_2)_{0-2}$aryl, the latter 3 groups being optionally substituted with one or more of halo, OH, $NH_2$, $C_{1-6}$alkyl, $C_{2-6}$alkenyl, $C_{2-6}$alkynyl, $OC_{1-16}$alkyl, $OC_{2-6}$alkenyl, or $OC_{2-6}$alkynyl; and $R^4$ is selected from H or $C_{1-10}$alkyl, wherein each alkyl, alkenyl, and alkynyl is optionally fluorosubstituted, and provided the compound of Formula II is not

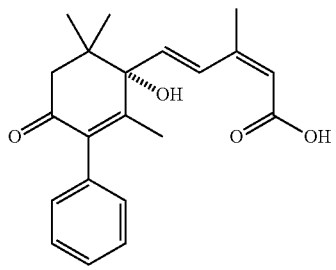 [SMILES: CC1=C(c2ccccc2)C(=O)CC(C)(C)[C@@]1(O)/C=C/C(C)=C\C(=O)O]

18. The method of claim 17, wherein the effective amount of the compound is about 0.1 µM to about 600 µM.

19. The method of claim 14, wherein the plant is canola, lentil, chickpea, *Arabidopsis*, faba bean, soybean, corn, rice, wheat, rye, barley, or fruit plant.

20. The method of claim 14, wherein one or more compounds of claim 1 or salt and/or solvate thereof is administered in combination with other known agents useful for regulating plant development.

21. The method of claim 17, wherein the effective amount of the compound is about 1 µM to about 500 µM.

22. The method of claim 17, wherein the effective amount of the compound is about 5 µM to about 250 µM.

* * * * *